US009512066B2

(12) United States Patent
Wanker et al.

(10) Patent No.: US 9,512,066 B2
(45) Date of Patent: Dec. 6, 2016

(54) ENHANCERS OF PROTEIN DEGRADATION

(75) Inventors: Erich Wanker, Berlin (DE); Thomas Wiglenda, Berlin (DE); Julius Tachu Babila, Berlin (DE); Annett Boddrich, Falkensee (DE); Michael Schmidt, Berlin (DE); Sandra Neuendorf, Hohen Neuendorf (DE); Franziska Schiele, Rottenburg-Kiebingen (DE)

(73) Assignee: MAX-DELBRUCK-CENTRUM FUR MOLEKULARE MEDIZIN, Berlin (DE)

( * ) Notice: Subject to any disclaimer, the term of this patent is extended or adjusted under 35 U.S.C. 154(b) by 0 days.

(21) Appl. No.: 13/391,316

(22) PCT Filed: Aug. 19, 2010

(86) PCT No.: PCT/EP2010/062111
§ 371 (c)(1),
(2), (4) Date: Jul. 27, 2012

(87) PCT Pub. No.: WO2011/020883
PCT Pub. Date: Feb. 24, 2011

(65) Prior Publication Data
US 2012/0282629 A1 Nov. 8, 2012

(30) Foreign Application Priority Data
Aug. 20, 2009 (EP) .................... 09168311

(51) Int. Cl.
C07C 251/86 (2006.01)
C07C 255/24 (2006.01)
C07D 213/77 (2006.01)
C07D 215/38 (2006.01)
C07D 233/88 (2006.01)
C07D 277/82 (2006.01)
C07D 401/12 (2006.01)

(52) U.S. Cl.
CPC .......... *C07C 251/86* (2013.01); *C07C 255/24* (2013.01); *C07D 213/77* (2013.01); *C07D 215/38* (2013.01); *C07D 233/88* (2013.01); *C07D 277/82* (2013.01); *C07D 401/12* (2013.01)

(58) Field of Classification Search
None
See application file for complete search history.

(56) References Cited

U.S. PATENT DOCUMENTS

| 3,809,675 | A | 5/1974 | Hansen |
| 5,561,017 | A | 10/1996 | Nagao et al. |
| 6,613,942 | B1 | 9/2003 | Ling et al. |
| 6,696,442 | B2 | 2/2004 | Wang et al. |
| 2006/0276433 | A1 | 12/2006 | Kawagoe et al. |
| 2009/0093480 | A1 | 4/2009 | Guenthenspberger et al. |

FOREIGN PATENT DOCUMENTS

| EP | 2 119 698 A1 | 11/2009 |
| WO | WO 96/40622 A1 | 12/1996 |
| WO | WO 00/21573 A1 | 4/2000 |
| WO | WO 2004/009602 A1 | 1/2004 |
| WO | WO2004/063196 A1 | 7/2004 |
| WO | WO 2007/112015 A2 | 10/2007 |
| WO | WO 2008/054633 A1 | 5/2008 |
| WO | WO 2009/102782 A2 | 8/2009 |

OTHER PUBLICATIONS

US 6,458,843, 10/2002, Wang et al. (withdrawn)
Gavrin, L. K. et al. Small Molecules That Target Protein Misfolding, J. Med. Chem. 2012, 55, 10823-10843.*
Grammaticakis, P. Comptes Rendus des Seances de I'Academie des Sciences, Serie C: Sciences Chimiques (1969), 269 (2), 137-140.*
Scientific Exchange Inc. chemical library compounds RN-884827-79-6, May 18, 2006.*
Ito et al. In Cancer Science 94(1), 3-8 (2003).*
Christiansen, W.G. Journal of the American Chemical Society. 1926, 48, 1365-9.*
XP002564356, Database Accession No. BRN6534122, Barbera et al., Molecular Crystals and Liquid Crystals, vol. 126, 1985, pp. 259-268.
XP002564357, Database Accession No. BRN7820445, Butora et al., JACS, vol. 119, No. 33, 1997, pp. 7694-7701.
XP002564358, Database Accession No. BRN7821579, Butora et al., JACS, vol. 119, No. 33, 1997, pp. 7694-7701.
XP002564359, Database Accession No. BRN3162328, Martin et al., JACS, vol. 79, 1957, pp. 2533-2540.
XP002564360, Database Accession No. BRN8482217, Asis et al., Farmaco, vol. 54, No. 8, 1999, pp. 517-523.
XP002564361, Database Accession No. BRN943300, Kugatowa et al., Chem. Abstracts., 1960, p. 5506.
XP002564362, Database Accession No. BRN1830841, Paquette et al., JACS, vol. 94, 1972, p. 8124.
XP002564363, Database Accession No. BRN3329810, Hudson et al., Journal of the Chemical Society, 1946, p. 76.
XP002564364, Database Accession No. BRN3485601, Gay et al., Journal of the Chemical Society, 1955, p. 2530.
XP002564365, Database Accession No. BRN8502154, Asis et al., Farmaco, vol. 54, No. 8, 1999, pp. 517-523.
XP002564366, Database Accession No. BRN8553054, Chen et al., Synthetic Communications, vol. 30, No. 13, 2000, pp. 2295-2300.
XP002564369, Database Accession No. BRN7818944, Butora et al., JACS, vol. 119, No. 33, 1997, pp. 7694-7701.
PCT International Search Report for PCT/EP2010/062111 dated Dec. 20, 2010 (5 pages) and PCT Written Opinion dated Dec. 20, 2010 (5 pages).

(Continued)

Primary Examiner — Clinton Brooks
(74) Attorney, Agent, or Firm — Sutherland Asbill & Brennan LLP

(57) ABSTRACT

The present invention relates to compounds suitable for modulating huntingtin protein processing and useful for treating or preventing huntingtin-related disorders. The invention provides pharmaceutical compositions comprising said compounds and methods of syntheses thereof.

11 Claims, 16 Drawing Sheets

(56) References Cited

OTHER PUBLICATIONS

Extended European Search Report for EP Application No. 09168311.0 mailed Feb. 18, 2010.
PCT International Preliminary Report on Patentability for PCT Application No. PCT/EP2010/062111 mailed Feb. 21, 2012.
Cushman et al., "Synthesis and Evaluation of New Protein-Tyrosine Kisane Inhibitors. Part 2. Phenylhydrazones," Bioorganic & Medical Chemistry Letters, 1991, 1(4):215-218.
El-Fotooh et al., "Synthesis and Reactions of 2-Mercaptobenzothiazole Derivatives of Expected Biological Activity. 2," American Chemical Society, 19822, pp. 207-208.
Liakatas et al., "Novel, Highly Nonlinear Optical Molecular Crystals Based on Multidonor-Substituted 4-Nitrophenylhydrazones," Adv. Mater., 1998, 10(10):777-782.

\* cited by examiner

Figure 1

$$R_1\text{-}\underset{R_2}{N}\text{-}NH_2 \quad + \quad O\!\!=\!\!\overset{}{\diagup}\!R_3 \quad \xrightarrow{\text{EtOH, rt}} \quad R_1\text{-}\underset{R_2}{N}\text{-}N\!\!=\!\!\overset{}{\diagup}\!R_3$$

| Hydrazine | Aldehyde | Example |
|---|---|---|
| 68 | 100 | 1 |
| 68 | 104 | 2 |
| 68 | 102 | 3 |
| 70 | 100 | 4 |
| 70 | 102 | 5 |
| 78 x HCl → 78 | 101 | 6 |
| 78 x HCl → 78 | 100 | 7 |
| 78 x HCl → 78 | 103 | 8 |
| 79 | 100 | 9 |
| 79 | 101 | 10 |
| 79 | 102 | 11 |
| 81 | 100 | 12 |
| 81 | 105 | 13 |
| 73 | 100 | 14 |
| 71 | 100 | 15 |
| 74 x HCl | 100 | 16 |
| 72 | 100 | 17 |
| 69 | 100 | 18 |
| 76 | 100 | 19 |
| 76 | 101 | 20 |
| 83 x HCl → 83 | 101 | 21 |
| 83 x HCl → 83 | 100 | 22 |
| 77 | 100 | 23 |
| 77 | 102 | 24 |
| 82 | 102 | 25 |
| 82 | 100 | 26 |
| 82 | 101 | 27 |
| 75 | 101 | 28 |
| 75 | 100 | 29 |
| 75 | 102 | 30 |
| 80 x HCl → 80 | 102 | 31 |
| 80 x HCl → 80 | 101 | 32 |
| 80 x HCl → 80 | 100 | 33 |
| 84 | 100 | 34 |
| 85 | 100 | 35 |
| 86 | 100 | 36 |
| 70 | 106 | 37 |
| 68 | 106 | 38 |
| 85 | 106 | 39 |
| 70 | 107 | 40 |
| 68 | 107 | 41 |
| 85 | 107 | 42 |
| 87 | 100 | 43 |
| 87 | 108 | 44 |
| 87 | 106 | 45 |
| 89 | 100 | 46 |
| 89 | 101 | 47 |
| 89 | 108 | 48 |
| 90 | 101 | 49 |
| 91 | 101 | 50 |
| 92 | 108 | 51 |
| 88 | 102 | 52 |
| 93 | 101 | 53 |
| 94 | 101 | 54 |
| 95 | 101 | 55 |
| 96 | 101 | 56 |
| 97 | 102 | 57 |
| 98 | 100 | 66 |
| 99 | 100 | 67 |

Figure 2

| Hydrazine: $R_1\text{-}N(R_2)\text{-}NH_2$ | | | Aldehyde: $O=R_3$ | |
|---|---|---|---|---|
| Entry | $R_1$ | $R_2$ | Entry | $R_3$ |
| 68 | 3,5-dichloro-4-(trifluoromethyl)phenyl | H | 100 | 3,4-dihydroxyphenyl |
| 69 | 3-chloro-4-(trifluoromethyl)phenyl | H | 101 | 3,4,5-trihydroxyphenyl |
| 70 | 4-(trifluoromethyl)phenyl | H | 102 | 3,5-dihydroxyphenyl |
| 71 | 3-chloro-5-(trifluoromethyl)phenyl | H | 103 | 2,3-dihydroxyphenyl |
| 72 | 2,4-dichlorophenyl | H | 104 | 3,4-dimethoxyphenyl |
| 73 | 2,5-dichlorophenyl | H | 105 | 2-hydroxyphenyl |
| 74 | 4-chlorophenyl | H | 106 | 3,5-dihydroxy-4-hydroxyphenyl |
| 75 | 4-cyano-2-chlorophenyl | H | 107 | 4-hydroxyphenyl |
| 76 | 4-iodophenyl | H | 108 | 2,3-dihydroxy-4-hydroxyphenyl |
| 77 | pentafluorophenyl | H | | |
| 78 | 3,4-difluorophenyl | H | | |
| 79 | 3,5-difluorophenyl | H | | |
| 80 | 4-nitrophenyl | H | | |
| 81 | phenyl | H | | |
| 82 | phenyl | Me | | |
| 83 | phenyl | phenyl | | |
| 84 | cyclohexyl | = $R_1$ | | |
| 85 | benzothiazolyl | H | | |

Figure 2 (continued)

| Hydrazine: | $R_1\text{-}N(R_2)\text{-}NH_2$ | | Aldehyde: | $O=R_3$ |
|---|---|---|---|---|
| Entry | R₁ | R₂ | Entry | R₃ |
| 86 | (cyanoethyl group) | H | | |
| 87 | (CF₃, NO₂-substituted phenyl) | Me | | |
| 88 | (HOOC-phenyl) | H | | |
| 89 | (quinoline) | H | | |
| 90 | (SH-triazine-pyridine) | H | | |
| 91 | (Cl-pyridine) | H | | |
| 92 | (morpholine-methyl) | = R₁ | | |
| 93 | (N-methylpiperazine-ethyl) | = R₁ | | |
| 94 | (Cl-pyridazine) | H | | |
| 95 | (indazole) | H | | |
| 96 | (imidazole-NH) | H | | |
| 97 | (F-benzyl) | Me | | |
| 98 | (NC-phenyl-piperidine-carbonyl) | H | | |
| 99 | (phenyl-ketone) | H | | |

A)

B)

SEQUENCE LISTING

```
<160> NUMBER OF SEQ ID NOS: 1

<210> SEQ ID NO 1
<211> LENGTH: 3144
<212> TYPE: PRT
<213> ORGANISM: Homo sapiens
<220> FEATURE:
<221> NAME/KEY: PEPTIDE
<222> LOCATION: (1)..(3144)
<220> FEATURE:
<221> NAME/KEY: PEPTIDE
<222> LOCATION: (1)..(3144)
<223> OTHER INFORMATION: human Huntingtin

<400> SEQUENCE: 1

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
```

-continued

```
                210                 215                 220
Ser Val Gln Glu Thr Leu Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Pro Thr Ile Arg Arg Thr Ala
                260                 265                 270

Ala Gly Ser Ala Val Ser Ile Cys Gln His Ser Arg Arg Thr Gln Tyr
                275                 280                 285

Phe Tyr Ser Trp Leu Leu Asn Val Leu Leu Gly Leu Leu Val Pro Val
                290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Val Lys Asp Thr Ser Leu
                325                 330                 335

Lys Gly Ser Phe Gly Val Thr Arg Lys Glu Met Glu Val Ser Pro Ser
                340                 345                 350

Ala Glu Gln Leu Val Gln Val Tyr Glu Leu Thr Leu His His Thr Gln
                355                 360                 365

His Gln Asp His Asn Val Val Thr Gly Ala Leu Glu Leu Leu Gln Gln
                370                 375                 380

Leu Phe Arg Thr Pro Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Ser Ser
                420                 425                 430

Cys Ser Pro Val Leu Ser Arg Lys Gln Lys Gly Lys Val Leu Leu Gly
                435                 440                 445

Glu Glu Glu Ala Leu Glu Asp Asp Ser Glu Ser Arg Ser Asp Val Ser
450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
                500                 505                 510

Asp Leu Ala Ser Cys Asp Leu Thr Ser Ser Ala Thr Asp Gly Asp Glu
                515                 520                 525

Glu Asp Ile Leu Ser His Ser Ser Gln Val Ser Ala Val Pro Ser
530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
                580                 585                 590

Leu Gly Leu Gln Ile Gly Gln Pro Gln Asp Glu Asp Glu Glu Ala Thr
                595                 600                 605

Gly Ile Leu Pro Asp Glu Ala Ser Glu Ala Phe Arg Asn Ser Ser Met
610                 615                 620

Ala Leu Gln Gln Ala His Leu Leu Lys Asn Met Ser His Cys Arg Gln
625                 630                 635                 640
```

-continued

```
Pro Ser Asp Ser Ser Val Asp Lys Phe Val Leu Arg Asp Glu Ala Thr
            645                 650                 655

Glu Pro Gly Asp Gln Glu Asn Lys Pro Cys Arg Ile Lys Gly Asp Ile
        660                 665                 670

Gly Gln Ser Thr Asp Asp Ser Ala Pro Leu Val His Cys Val Arg
            675                 680                 685

Leu Leu Ser Ala Ser Phe Leu Leu Thr Gly Gly Lys Asn Val Leu Val
        690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
            725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
            755                 760                 765

Ala Thr Ala Ile Leu Cys Gly Thr Leu Ile Cys Ser Ile Leu Ser Arg
        770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
            805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
    850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
            885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
        930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
            965                 970                 975

Phe Ser Val Ser Thr Ile Thr Arg Ile Tyr Arg Gly Tyr Asn Leu Leu
            980                 985                 990

Pro Ser Ile Thr Asp Val Thr Met Glu Asn Asn Leu Ser Arg Val Ile
        995                 1000                1005

Ala Ala Val Ser His Glu Leu Ile Thr Ser Thr Thr Arg Ala Leu
    1010                1015                1020

Thr Phe Gly Cys Cys Glu Ala Leu Cys Leu Leu Ser Thr Ala Phe
    1025                1030                1035

Pro Val Cys Ile Trp Ser Leu Gly Trp His Cys Gly Val Pro Pro
    1040                1045                1050
```

```
Leu Ser Ala Ser Asp Glu Ser Arg Lys Ser Cys Thr Val Gly Met
    1055            1060            1065

Ala Thr Met Ile Leu Thr Leu Leu Ser Ser Ala Trp Phe Pro Leu
    1070            1075            1080

Asp Leu Ser Ala His Gln Asp Ala Leu Ile Leu Ala Gly Asn Leu
    1085            1090            1095

Leu Ala Ala Ser Ala Pro Lys Ser Leu Arg Ser Ser Trp Ala Ser
    1100            1105            1110

Glu Glu Glu Ala Asn Pro Ala Ala Thr Lys Gln Glu Glu Val Trp
    1115            1120            1125

Pro Ala Leu Gly Asp Arg Ala Leu Val Pro Met Val Glu Gln Leu
    1130            1135            1140

Phe Ser His Leu Leu Lys Val Ile Asn Ile Cys Ala His Val Leu
    1145            1150            1155

Asp Asp Val Ala Pro Gly Pro Ala Ile Lys Ala Ala Leu Pro Ser
    1160            1165            1170

Leu Thr Asn Pro Pro Ser Leu Ser Pro Ile Arg Arg Lys Gly Lys
    1175            1180            1185

Glu Lys Glu Pro Gly Glu Gln Ala Ser Val Pro Leu Ser Pro Lys
    1190            1195            1200

Lys Gly Ser Glu Ala Ser Ala Ala Ser Arg Gln Ser Asp Thr Ser
    1205            1210            1215

Gly Pro Val Thr Thr Ser Lys Ser Ser Ser Leu Gly Ser Phe Tyr
    1220            1225            1230

His Leu Pro Ser Tyr Leu Lys Leu His Asp Val Leu Lys Ala Thr
    1235            1240            1245

His Ala Asn Tyr Lys Val Thr Leu Asp Leu Gln Asn Ser Thr Glu
    1250            1255            1260

Lys Phe Gly Gly Phe Leu Arg Ser Ala Leu Asp Val Leu Ser Gln
    1265            1270            1275

Ile Leu Glu Leu Ala Thr Leu Gln Asp Ile Gly Lys Cys Val Glu
    1280            1285            1290

Glu Ile Leu Gly Tyr Leu Lys Ser Cys Phe Ser Arg Glu Pro Met
    1295            1300            1305

Met Ala Thr Val Cys Val Gln Gln Leu Leu Lys Thr Leu Phe Gly
    1310            1315            1320

Thr Asn Leu Ala Ser Gln Phe Asp Gly Leu Ser Ser Asn Pro Ser
    1325            1330            1335

Lys Ser Gln Gly Arg Ala Gln Arg Leu Gly Ser Ser Ser Val Arg
    1340            1345            1350

Pro Gly Leu Tyr His Tyr Cys Phe Met Ala Pro Tyr Thr His Phe
    1355            1360            1365

Thr Gln Ala Leu Ala Asp Ala Ser Leu Arg Asn Met Val Gln Ala
    1370            1375            1380

Glu Gln Glu Asn Asp Thr Ser Gly Trp Phe Asp Val Leu Gln Lys
    1385            1390            1395

Val Ser Thr Gln Leu Lys Thr Asn Leu Thr Ser Val Thr Lys Asn
    1400            1405            1410

Arg Ala Asp Lys Asn Ala Ile His Asn His Ile Arg Leu Phe Glu
    1415            1420            1425

Pro Leu Val Ile Lys Ala Leu Lys Gln Tyr Thr Thr Thr Thr Cys
    1430            1435            1440

Val Gln Leu Gln Lys Gln Val Leu Asp Leu Leu Ala Gln Leu Val
```

```
            1445                1450                1455
Gln Leu Arg Val Asn Tyr Cys Leu Leu Asp Ser Asp Gln Val Phe
        1460                1465                1470
Ile Gly Phe Val Leu Lys Gln Phe Glu Tyr Ile Glu Val Gly Gln
        1475                1480                1485
Phe Arg Glu Ser Glu Ala Ile Ile Pro Asn Ile Phe Phe Phe Leu
        1490                1495                1500
Val Leu Leu Ser Tyr Glu Arg Tyr His Ser Lys Gln Ile Ile Gly
        1505                1510                1515
Ile Pro Lys Ile Ile Gln Leu Cys Asp Gly Ile Met Ala Ser Gly
        1520                1525                1530
Arg Lys Ala Val Thr His Ala Ile Pro Ala Leu Gln Pro Ile Val
        1535                1540                1545
His Asp Leu Phe Val Leu Arg Gly Thr Asn Lys Ala Asp Ala Gly
        1550                1555                1560
Lys Glu Leu Glu Thr Gln Lys Glu Val Val Ser Met Leu Leu
        1565                1570                1575
Arg Leu Ile Gln Tyr His Gln Val Leu Glu Met Phe Ile Leu Val
        1580                1585                1590
Leu Gln Gln Cys His Lys Glu Asn Glu Asp Lys Trp Lys Arg Leu
        1595                1600                1605
Ser Arg Gln Ile Ala Asp Ile Ile Leu Pro Met Leu Ala Lys Gln
        1610                1615                1620
Gln Met His Ile Asp Ser His Glu Ala Leu Gly Val Leu Asn Thr
        1625                1630                1635
Leu Phe Glu Ile Leu Ala Pro Ser Ser Leu Arg Pro Val Asp Met
        1640                1645                1650
Leu Leu Arg Ser Met Phe Val Thr Pro Asn Thr Met Ala Ser Val
        1655                1660                1665
Ser Thr Val Gln Leu Trp Ile Ser Gly Ile Leu Ala Ile Leu Arg
        1670                1675                1680
Val Leu Ile Ser Gln Ser Thr Glu Asp Ile Val Leu Ser Arg Ile
        1685                1690                1695
Gln Glu Leu Ser Phe Ser Pro Tyr Leu Ile Ser Cys Thr Val Ile
        1700                1705                1710
Asn Arg Leu Arg Asp Gly Asp Ser Thr Ser Thr Leu Glu Glu His
        1715                1720                1725
Ser Glu Gly Lys Gln Ile Lys Asn Leu Pro Glu Glu Thr Phe Ser
        1730                1735                1740
Arg Phe Leu Leu Gln Leu Val Gly Ile Leu Leu Glu Asp Ile Val
        1745                1750                1755
Thr Lys Gln Leu Lys Val Glu Met Ser Glu Gln Gln His Thr Phe
        1760                1765                1770
Tyr Cys Gln Glu Leu Gly Thr Leu Leu Met Cys Leu Ile His Ile
        1775                1780                1785
Phe Lys Ser Gly Met Phe Arg Arg Ile Thr Ala Ala Ala Thr Arg
        1790                1795                1800
Leu Phe Arg Ser Asp Gly Cys Gly Gly Ser Phe Tyr Thr Leu Asp
        1805                1810                1815
Ser Leu Asn Leu Arg Ala Arg Ser Met Ile Thr Thr His Pro Ala
        1820                1825                1830
Leu Val Leu Leu Trp Cys Gln Ile Leu Leu Leu Val Asn His Thr
        1835                1840                1845
```

```
Asp Tyr Arg Trp Trp Ala Glu Val Gln Gln Thr Pro Lys Arg His
1850                1855                1860

Ser Leu Ser Ser Thr Lys Leu Leu Ser Pro Gln Met Ser Gly Glu
1865                1870                1875

Glu Glu Asp Ser Asp Leu Ala Ala Lys Leu Gly Met Cys Asn Arg
1880                1885                1890

Glu Ile Val Arg Arg Gly Ala Leu Ile Leu Phe Cys Asp Tyr Val
1895                1900                1905

Cys Gln Asn Leu His Asp Ser Glu His Leu Thr Trp Leu Ile Val
1910                1915                1920

Asn His Ile Gln Asp Leu Ile Ser Leu Ser His Glu Pro Pro Val
1925                1930                1935

Gln Asp Phe Ile Ser Ala Val His Arg Asn Ser Ala Ala Ser Gly
1940                1945                1950

Leu Phe Ile Gln Ala Ile Gln Ser Arg Cys Glu Asn Leu Ser Thr
1955                1960                1965

Pro Thr Met Leu Lys Lys Thr Leu Gln Cys Leu Glu Gly Ile His
1970                1975                1980

Leu Ser Gln Ser Gly Ala Val Leu Thr Leu Tyr Val Asp Arg Leu
1985                1990                1995

Leu Cys Thr Pro Phe Arg Val Leu Ala Arg Met Val Asp Ile Leu
2000                2005                2010

Ala Cys Arg Arg Val Glu Met Leu Leu Ala Ala Asn Leu Gln Ser
2015                2020                2025

Ser Met Ala Gln Leu Pro Met Glu Glu Leu Asn Arg Ile Gln Glu
2030                2035                2040

Tyr Leu Gln Ser Ser Gly Leu Ala Gln Arg His Gln Arg Leu Tyr
2045                2050                2055

Ser Leu Leu Asp Arg Phe Arg Leu Ser Thr Met Gln Asp Ser Leu
2060                2065                2070

Ser Pro Ser Pro Pro Val Ser Ser His Pro Leu Asp Gly Asp Gly
2075                2080                2085

His Val Ser Leu Glu Thr Val Ser Pro Asp Lys Asp Trp Tyr Val
2090                2095                2100

His Leu Val Lys Ser Gln Cys Trp Thr Arg Ser Asp Ser Ala Leu
2105                2110                2115

Leu Glu Gly Ala Glu Leu Val Asn Arg Ile Pro Ala Glu Asp Met
2120                2125                2130

Asn Ala Phe Met Met Asn Ser Glu Phe Asn Leu Ser Leu Leu Ala
2135                2140                2145

Pro Cys Leu Ser Leu Gly Met Ser Glu Ile Ser Gly Gly Gln Lys
2150                2155                2160

Ser Ala Leu Phe Glu Ala Arg Glu Val Thr Leu Ala Arg Val
2165                2170                2175

Ser Gly Thr Val Gln Gln Leu Pro Ala Val His His Val Phe Gln
2180                2185                2190

Pro Glu Leu Pro Ala Glu Pro Ala Ala Tyr Trp Ser Lys Leu Asn
2195                2200                2205

Asp Leu Phe Gly Asp Ala Ala Leu Tyr Gln Ser Leu Pro Thr Leu
2210                2215                2220

Ala Arg Ala Leu Ala Gln Tyr Leu Val Val Val Ser Lys Leu Pro
2225                2230                2235
```

-continued

| | | | | | | | | | | | |
|---|---|---|---|---|---|---|---|---|---|---|---|
|Ser|His|Leu|His|Leu|Pro|Pro|Glu|Lys|Glu|Lys|Asp|Ile|Val|Lys|
| 2240| | | |2245| | | | |2250| | | | | |

Phe Val Val Ala Thr Leu Glu Ala Leu Ser Trp His Leu Ile His
2255                2260                2265

Glu Gln Ile Pro Leu Ser Leu Asp Leu Gln Ala Gly Leu Asp Cys
2270                2275                2280

Cys Cys Leu Ala Leu Gln Leu Pro Gly Leu Trp Ser Val Val Ser
2285                2290                2295

Ser Thr Glu Phe Val Thr His Ala Cys Ser Leu Ile Tyr Cys Val
2300                2305                2310

His Phe Ile Leu Glu Ala Val Ala Val Gln Pro Gly Glu Gln Leu
2315                2320                2325

Leu Ser Pro Glu Arg Arg Thr Asn Thr Pro Lys Ala Ile Ser Glu
2330                2335                2340

Glu Glu Glu Glu Val Asp Pro Asn Thr Gln Asn Pro Lys Tyr Ile
2345                2350                2355

Thr Ala Ala Cys Glu Met Val Ala Glu Met Val Glu Ser Leu Gln
2360                2365                2370

Ser Val Leu Ala Leu Gly His Lys Arg Asn Ser Gly Val Pro Ala
2375                2380                2385

Phe Leu Thr Pro Leu Leu Arg Asn Ile Ile Ile Ser Leu Ala Arg
2390                2395                2400

Leu Pro Leu Val Asn Ser Tyr Thr Arg Val Pro Pro Leu Val Trp
2405                2410                2415

Lys Leu Gly Trp Ser Pro Lys Pro Gly Gly Asp Phe Gly Thr Ala
2420                2425                2430

Phe Pro Glu Ile Pro Val Glu Phe Leu Gln Glu Lys Glu Val Phe
2435                2440                2445

Lys Glu Phe Ile Tyr Arg Ile Asn Thr Leu Gly Trp Thr Ser Arg
2450                2455                2460

Thr Gln Phe Glu Glu Thr Trp Ala Thr Leu Leu Gly Val Leu Val
2465                2470                2475

Thr Gln Pro Leu Val Met Glu Gln Glu Glu Ser Pro Pro Glu Glu
2480                2485                2490

Asp Thr Glu Arg Thr Gln Ile Asn Val Leu Ala Val Gln Ala Ile
2495                2500                2505

Thr Ser Leu Val Leu Ser Ala Met Thr Val Pro Val Ala Gly Asn
2510                2515                2520

Pro Ala Val Ser Cys Leu Glu Gln Gln Pro Arg Asn Lys Pro Leu
2525                2530                2535

Lys Ala Leu Asp Thr Arg Phe Gly Arg Lys Leu Ser Ile Ile Arg
2540                2545                2550

Gly Ile Val Glu Gln Glu Ile Gln Ala Met Val Ser Lys Arg Glu
2555                2560                2565

Asn Ile Ala Thr His His Leu Tyr Gln Ala Trp Asp Pro Val Pro
2570                2575                2580

Ser Leu Ser Pro Ala Thr Thr Gly Ala Leu Ile Ser His Glu Lys
2585                2590                2595

Leu Leu Leu Gln Ile Asn Pro Glu Arg Glu Leu Gly Ser Met Ser
2600                2605                2610

Tyr Lys Leu Gly Gln Val Ser Ile His Ser Val Trp Leu Gly Asn
2615                2620                2625

Ser Ile Thr Pro Leu Arg Glu Glu Glu Trp Asp Glu Glu Glu Glu

-continued

|  |  |  | 2630 |  |  |  | 2635 |  |  |  | 2640 |  |  |  |
| --- | --- | --- | --- | --- | --- | --- | --- | --- | --- | --- | --- | --- | --- | --- |

Glu Glu Ala Asp Ala Pro Ala Pro Ser Ser Pro Pro Thr Ser Pro
    2645            2650            2655

Val Asn Ser Arg Lys His Arg Ala Gly Val Asp Ile His Ser Cys
    2660            2665            2670

Ser Gln Phe Leu Leu Glu Leu Tyr Ser Arg Trp Ile Leu Pro Ser
    2675            2680            2685

Ser Ser Ala Arg Arg Thr Pro Ala Ile Leu Ile Ser Glu Val Val
    2690            2695            2700

Arg Ser Leu Leu Val Val Ser Asp Leu Phe Thr Glu Arg Asn Gln
    2705            2710            2715

Phe Glu Leu Met Tyr Val Thr Leu Thr Glu Leu Arg Arg Val His
    2720            2725            2730

Pro Ser Glu Asp Glu Ile Leu Ala Gln Tyr Leu Val Pro Ala Thr
    2735            2740            2745

Cys Lys Ala Ala Ala Val Leu Gly Met Asp Lys Ala Val Ala Glu
    2750            2755            2760

Pro Val Ser Arg Leu Leu Glu Ser Thr Leu Arg Ser Ser His Leu
    2765            2770            2775

Pro Ser Arg Val Gly Ala Leu His Gly Val Leu Tyr Val Leu Glu
    2780            2785            2790

Cys Asp Leu Leu Asp Asp Thr Ala Lys Gln Leu Ile Pro Val Ile
    2795            2800            2805

Ser Asp Tyr Leu Leu Ser Asn Leu Lys Gly Ile Ala His Cys Val
    2810            2815            2820

Asn Ile His Ser Gln Gln His Val Leu Val Met Cys Ala Thr Ala
    2825            2830            2835

Phe Tyr Leu Ile Glu Asn Tyr Pro Leu Asp Val Gly Pro Glu Phe
    2840            2845            2850

Ser Ala Ser Ile Ile Gln Met Cys Gly Val Met Leu Ser Gly Ser
    2855            2860            2865

Glu Glu Ser Thr Pro Ser Ile Ile Tyr His Cys Ala Leu Arg Gly
    2870            2875            2880

Leu Glu Arg Leu Leu Leu Ser Glu Gln Leu Ser Arg Leu Asp Ala
    2885            2890            2895

Glu Ser Leu Val Lys Leu Ser Val Asp Arg Val Asn Val His Ser
    2900            2905            2910

Pro His Arg Ala Met Ala Ala Leu Gly Leu Met Leu Thr Cys Met
    2915            2920            2925

Tyr Thr Gly Lys Glu Lys Val Ser Pro Gly Arg Thr Ser Asp Pro
    2930            2935            2940

Asn Pro Ala Ala Pro Asp Ser Glu Ser Val Ile Val Ala Met Glu
    2945            2950            2955

Arg Val Ser Val Leu Phe Asp Arg Ile Arg Lys Gly Phe Pro Cys
    2960            2965            2970

Glu Ala Arg Val Val Ala Arg Ile Leu Pro Gln Phe Leu Asp Asp
    2975            2980            2985

Phe Phe Pro Pro Gln Asp Ile Met Asn Lys Val Ile Gly Glu Phe
    2990            2995            3000

Leu Ser Asn Gln Gln Pro Tyr Pro Gln Phe Met Ala Thr Val Val
    3005            3010            3015

Tyr Lys Val Phe Gln Thr Leu His Ser Thr Gly Gln Ser Ser Met
    3020            3025            3030

```
Val Arg Asp Trp Val Met Leu Ser Leu Ser Asn Phe Thr Gln Arg
    3035            3040            3045
Ala Pro Val Ala Met Ala Thr Trp Ser Leu Ser Cys Phe Phe Val
    3050            3055            3060
Ser Ala Ser Thr Ser Pro Trp Val Ala Ala Ile Leu Pro His Val
    3065            3070            3075
Ile Ser Arg Met Gly Lys Leu Glu Gln Val Asp Val Asn Leu Phe
    3080            3085            3090
Cys Leu Val Ala Thr Asp Phe Tyr Arg His Gln Ile Glu Glu Glu
    3095            3100            3105
Leu Asp Arg Arg Ala Phe Gln Ser Val Leu Glu Val Val Ala Ala
    3110            3115            3120
Pro Gly Ser Pro Tyr His Arg Leu Leu Thr Cys Leu Arg Asn Val
    3125            3130            3135
His Lys Val Thr Thr Cys
    3140
```

ENHANCERS OF PROTEIN DEGRADATION

CROSS REFERENCE TO RELATED APPLICATIONS

This application claims the priority benefit of PCT/EP2010/062111 filed on Aug. 19, 2010 and European Application No. 09168311.0 filed on Aug. 20, 2009. The contents of these applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Feb. 16, 2012, is named 45459PWO.ST25.txt and is 28,060 bytes in size.

The present invention relates to hydrazone compounds effective in inhibiting protein misfolding, accumulation of misfolded proteins and inducing degradation of misfolded proteins and aggregates thereof. Further, the compounds of the present invention are suitable for treating or preventing conditions associated with the occurrence of protein misfolding and aggregate formation. The invention provides compositions comprising a hydrazone compound in a stabilized form and methods of producing thereof.

Protein metabolism comprises a complex interaction of a plurality of strongly regulated intracellular processes. After synthesis of gene encoded proteins on ribonucleoprotein complexes, the newly synthesized polypeptide chain is processed, i.e. subjected to various posttranslational modifications including folding of the polypeptide chain into the destined three dimensional conformation resulting in a functional protein molecule. It is a prerequisite for the viability of any cell that besides the anabolism also the protein catabolism is strongly regulated. Dysfunctions in the post-translational protein processing may result in changing the steady state level of one or more protein species effecting the physiology of the cell. Proteins which are not properly folded or misfolded, respectively, are subjected to refolding and if refolding does not lead to a correct conformation to degradation. However, some misfolded and/or abundantly expressed proteins tend to form aggregates by accumulating with each other and/or with other (macro)molecules within compartments of the cell or extracellular, but within multicellular organisms. Reasons therefor are amongst others mutations in protein encoding genes and/or an imbalance of protein synthesis and degradation.

A number of mutations is known in the art leading to mutated proteins which have a considerably tendency to be misfolded and/or form protein aggregates. Following translation of the mutated protein encoding gene locus the synthesized polypeptide chain will be misfolded into a conformation allowing on the one hand to circumvent or escape the protein degradation machinery of the cell or organism, respectively, and on the other hand to accumulate with each other and/or other protein species. Aggregate formation may result in damaging organelles and finally in cell death and tissue degeneration. If the affected tissue is one which is hardly regenerative (as for example nerve tissue), occurrence of protein misfolding and aggregate formation will result in the death of the organism.

Fatal diseases in mammals, associated with and/or caused by protein misfolding and formation of intracellular protein aggregates are known in the art and accompanied mostly with successive loss of brain functions due to degeneration of affected nerve cells and tissue. Such prominent diseases are for example Alzheimer's disease, Parkinson's disease and Prion diseases as bovine spongiform encephalopathy (BSE), Scrapie and Creutzfeldt-Jakob disease.

Likewise, other diseases such as Chorea Huntington or Spinocerebellar ataxia are caused by expression of a protein species which undergoes pathological misfolding and accumulation, wherein misfolding is due to the presence of a polyglutamine stretch or an expanded polyglutamine stretch, respectively, within the primary structure of said protein species.

Chorea Huntington, also called Huntington's disease (HD) is a progressive neurodegenerative disorder characterized by motor disturbance, cognitive loss and psychiatric manifestations. First symptoms arise in the fourth to fifth decade of life and gradually becomes more severe over the course of approximately 15 years until death. HD has been shown to be an autosomal dominant hereditary disorder caused by expression of a pathogenic variant of the protein huntingtin (htt). Compared to wild-type (wt) htt, toxic htt exhibit an abnormally extended polyglutamine stretch at its N-terminal end resulting from expression of a mutated htt (mhtt) encoding gene, the open reading frame of which has an expansion of more than 35 repeats of the triplet CAG. Inter alia, deleterious effects of HD are generated due to aggregation of mhtt with itself and/or with other proteins within the nucleus and cytoplasm of neuronal cells resulting in degradation of nerve tissue.

Although htt is ubiquitously expressed throughout the whole body, HD pathology predominantly concerns the central nervous system (CNS). Therefore, the current therapeutics for HD have been targeted at preventing neuronal damage or treating symptoms of neuronal damage. Most of the agents used for HD therapy are well-known psychopharmaceuticals and neuroepileptics designed to alleviate diverse psychological symptoms (e.g. depression, epilepsy) and motor dysfunctions (e.g. hyperkinesis, dance-like movements).

Another approach for HD therapy is focussed on the htt protein itself. Appropriate therapeutically effective agents therefore act on the stage of preventing mhtt aggregation by enhancing protein-folding activity and proteolysis performance of mhtt expressing cells. Such agents modulate htt conformations or influence enzymes involved in post-translational protein modification and processing. One example therefor is geldenamycin which elevates the expression of heat shock proteins (Hsps). Hsps are members of the chaperone protein family involved in refolding of several aberrantly folded proteins. Therefore, geldenamycin may limit the accumulation of mhtt aggregates. However, compounds from which have been shown to possess some degree of efficacy in treating HD symptoms via alteration of the protein folding or degradation machinery of the cell are chemically unrelated and partially harmful for other physiological processes. Moreover, known agents acting on the stage of the primary mediator of HD itself are not suitable for an efficient HD therapy when used as the only active ingredient. Further, gene therapy based on RNA interference (RNAi) directed against the mhtt encoding gene or application of antibodies specific for mhtt are discussed. However, due to the ubiquitary occurrence of mhtt throughout the whole body and the relatively late occurrence of HD specific symptoms, it seems to be difficult to establish an effective and durable gene targeting therapy without undesired germline manipulation. An effective antibody therapy in turn requires the selective supply of anti-mhtt antibodies to affected nerve tissue and overcoming the blood/brain barrier.

In summary it can be held that despite the progress made in Huntington research, an efficient or primal therapy could not be found, and thus a healing of this disease has not been possible. By means of medicaments which are available today, the symptoms of this disease can merely be alleviated. Therefore, there is a need for a medicament which can efficiently stop the progress of HD.

Surprisingly, it was found out by the present inventors that hydrazone compounds of formula I or a physiologically acceptable salt, hydrate, solvate, tautomer, stereoisomer, metabolite or prodrug thereof, as defined below, are useful for modulating, e.g. reducing the level of misfolded proteins, proteins which tend to be misfolded and proteins forming toxic aggregates. Especially they are useful for reducing the intracellular amount of misfolded proteins which are abundantly present in a cell, e.g. due to accumulation and/or overexpression. Further, the compounds as described therein are useful for inhibiting or preventing pathological accumulation of proteins, protein misfolding and/or degrading aggregates mainly comprising misfolded proteins. In particular the hydrazone compounds of formula I as described herein are useful for htt protein processing in prokaryotic or eukaryotic cells expressing htt or toxic variants thereof and especially in mhtt expressing mammalian cells.

For a better understanding and unless otherwise specified various terms used in the description and in the claims are defined as follows:

"htt" or "wt htt" refers to huntingtin or wild-type huntingtin protein having an amino acid sequence of SEQ ID NO:1 and homologs thereof comprising a sequence having at least 70%, preferably 70-80%, more preferably 80-90% and 90-95%, and most preferably >95% identity with SEQ ID NO:1 over the whole length of SEQ ID NO:1, as long as they do not possess a poly-Q-stretch of more than 35, i.e. an amino acid sequence of more than 35 contiguous glutamine residues. Further, "htt" or "wthtt" may refer to a portion of a htt as defined above, wherein said portion is encoded by one or more exons of a htt encoding gene, preferably by exon 1 of a htt encoding gene, e.g. the human htt encoding gene, provided that said portion comprises a polyglutamine stretch of up to 35, i.e. an amino acid sequence of up to 35 contiguous glutamine residues.

"mhtt" refers to a mutated variant of htt, wherein said mutated variant has compared to wild-type htt a sequence portion on the primary structure of 27 or more, e.g. more than 35 contiguous glutamine residues and is characterized by its tendency to misfolding and the ability to form toxic aggregates with each other and/or with wild-type htt or diverse other proteins under physiological conditions. Mhtt can exhibit up to 180 or more contiguous glutamine residues and can be further modified, for example, by post-translational modifications.

Htt or mhtt as well as homologues thereof as described herein, further can be a part of a chimeric protein. Such chimeric constructs are also comprised by the terms "htt" or "mhtt" as long as they show physiological characteristics comparable to huntingtin or toxic variants thereof.

"Alkyl" refers to straight or branched chain unsubstituted hydrocarbon groups of 1 to 16 carbon atoms, preferably of 1 to 8 carbon atoms, more preferably 1-4 carbon atoms.

"Alkenyl" refers to a straight or branched hydrocarbon group containing at least one double bond, having from 2 to 16 carbon atoms, preferably 2 to 8 carbon atoms and more preferably 2 to 4 carbon atoms.

"Alkynyl" refers to a straight or branched hydrocarbon group containing at least one triple bond, optionally further containing at least one double bond, having from 2 to 14 carbon atoms, preferably 2 to 8 carbon atoms.

"Aryl" refers to monocyclic, bicyclic or tricyclic, preferably monocyclic, aromatic hydrocarbon groups having 6 to 14 carbon atoms in the ring portion, such as phenyl, naphthyl, biphenyl and diphenyl groups. Preferably, aryl is phenyl.

"Heteroalkyl", "heteroalkenyl" and "heteroalkynyl" refer to an alkyl, alkenyl or alkynyl group, respectively, as described herein, wherein at least one carbon atom of the alkyl, alkenyl or alkynyl portion is replaced a heteroatom, e.g. selected from N, O and S. A preferred heteroalkyl is propanenitrile.

"Heteroaryl" refers to a 5-14 membered fully or partially aromatic ring group containing one to five heteroatoms selected from the group consisting of nitrogen (N), oxygen (O) and sulfur (S). For purposes of this invention, the heteroaryl may be a monocyclic, bicyclic, tricyclic or tetracyclic ring system, which may include fused or bridged ring systems; and the nitrogen, carbon or sulfur atoms in the heteroaryl may be optionally oxidized; the nitrogen atom may be optionally quaternized. Preferably, heteroaryl is selected from indol and benzothiazol.

"Cycloalkyl" refers to saturated cyclic hydrocarbon ring systems, preferably containing 3 to 14 carbons.

"Cycloalkenyl" refers to a cyclic hydrocarbon chain group, containing at least one double bond, having from 3 to 14 carbon atoms.

"Cycloalkynyl" refers to a cyclic hydrocarbon chain group, containing at least one triple bond, having from 3 to 14 carbon atoms.

"Cycloheteroalkyl", "cycloheteroalkenyl" and "cycloheteroalkynyl" refer to cycloalkyl, cycloalkenyl or cycloalkynyl groups, respectively, as described herein, wherein at least one carbon atom of the cycloalkyl, cycloalkenyl or cycloalkynyl portion, respectively, is replaced by a heteroatom, e.g. selected from N, O and S.

"Prodrug" refers to a compound that may be converted under physiological conditions or by solvolysis to a biologically active compound of the invention. Thus, the term "prodrug" refers to a metabolic precursor of a compound of the invention that is pharmaceutically acceptable. The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention.

"Halogen" refers to fluorine, chlorine, bromine and iodine. Preferred are fluorine and chlorine.

"Proteids" refer to conjugated proteins composed of proteinogenic and/or non-proteinogenic amino acids and a non-protein portion like carbohydrates, lipids or nucleic acids. Preferred proteids used within the context of the invention are glyco-, lipo- and nucleo-proteins.

The present inventions provides in a first aspect a compound of formula I

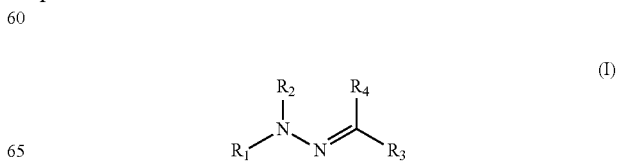

or a physiologically acceptable salt, hydrate, solvate, tautomer, stereoisomer, metabolite or prodrug thereof, and a composition comprising at least one compound of formula I or a physiologically acceptable salt, hydrate, solvate, tautomer, stereoisomer, metabolite or prodrug thereof,
wherein
at least one of $R_1$ and $R_2$ is selected from, preferably both of $R_1$ and $R_2$ are independently selected from
(i) H,
(ii) CN, or
(iii) an acyclic radical selected from $C_{1-16}$ alkyl, $C_{2-16}$ alkenyl, $C_{2-16}$ alkynyl, wherein each acyclic radical is optionally mono- or poly-substituted with halo, —CN, —$NO_2$, =$NR_5$, —$N(R_5)_2$, —$N(R_5)_3{}^+$—$NR_5COR_5$, —$S(O)_nR_5$, $S(O)_nN(R_5)_2$, with n=0-3, —$OR_5$, $OCOR_5$, —$CON(R_5)_2$, —$COOR_5$, —$COR_5$, and/or a $C_{3-14}$ carbocyclic or heterocyclic moiety which may be substituted with halo, $C_nH_{2n}R_5$, with n=0-8, $OR_5$, CN, or
(iv) a $C_{3-14}$ carbocyclic or heterocyclic radical selected from mono- or bicyclic saturated, unsaturated and/or aromatic radicals which may contain up to 5 heteroatoms, e.g. N, S, or O, wherein each cyclic radical is optionally mono- or poly-substituted with $R_5$, halo, —CN, —$NO_2$, =$NR_5$, —$N(R_5)_2$, —$N(R_5)_3{}^+$, —$NR_5COR_5$, —$S(O)_nR_5$, $S(O)_nN(R_5)_2$, with n=0-3, —$OR_5$, $OCOR_5$, —$CON(R_5)_2$, —$COOR_5$, —$COR_5$, and/or a $C_{3-14}$ carbocyclic or heterocyclic moiety which may be substituted with halo, $C_nH_{2n}R_5$, with n=0-8, $OR_5$, CN, or
(v) N, $R_1$ and $R_2$ form together a heterocyclic radical selected from mono- or bicyclic, saturated and/or aromatic radicals which may contain up to 5 heteroatoms, e.g. N, S, or O, wherein each heterocyclic radical is optionally mono- or poly-substituted with $R_5$, halo, —CN, —$NO_2$, =$NR_5$, —$N(R_5)_2$, —$N(R_5)_3{}^+$, —$NR_5COR_5$, —$S(O)_nR_5$, $S(O)_nN(R_5)_2$, with n=0-3, —$OR_5$, $OCOR_5$, —$CON(R_5)_2$, —$COOR_5$, —$COR_5$, and/or a $C_{3-14}$ carbocyclic or heterocyclic moiety which may be substituted with halo, $C_nH_{2n}R_5$, with n=0-8, $OR_5$, CN,
(vi) —$S(O)_nR_5$, —$S(O)_nN(R_5)_2$, with n=0-3, —$OR_5$, —$OCOR_5$, —$COR_5$, —$CON(R_5)_2$, —$COOR_5$, —$COC_nH_{2n}COR_5$ with n=0-4, —$OCOC_nH_{2n}COOR_5$ with n=0-4, —$(CH_2O)_nR_5$ with n=0-7, —$(CO)_nR_5$ with n=1-3, —CO—NHN=$R_5$, —CO—NHNHR$_5$, —CO—NHNHR$_5$, —CONHCOR$_5$, —CH=NNHR$_5$, —CH=NN=$R_5$, —$C_nH_{2n}R_5$ with n=0-8.

In one embodiment of the invention $R_1$ and/or $R_2$ is not $CONH_2$. In another aspect of the invention $R_1$ and/or $R_2$ is not pyrazolopyrimidine or substituted pyrazolopyrimidine. In another aspect of the invention $R_1$ and/or $R_2$ is not —$COR_5$.

In another aspect of the invention $R_1$ and/or $R_2$ is not —$CONH_2$ and/or pyrazolopyrimidine or substituted pyrazolopyrimidine and/or —$COR_5$.

At least one of $R_3$ and $R_4$ is a $C_{3-14}$ carbocyclic or heterocyclic radical selected from mono- or bicyclic saturated, unsaturated and/or aromatic radicals which may contain up to 5 heteroatoms, e.g. N, S, or O, wherein each cyclic radical is mono- or poly-substituted and preferably poly-substituted, e.g. 2- or 3 times substituted with —OH, —$OR_6$, and/or —$OCOR_6$, and one of $R_3$ and $R_4$ may be H or $CH_3$, wherein H is preferred.

In one embodiment at least one of $R_3$ and $R_4$ is a $C_{3-14}$ carbocyclic or heterocyclic radical selected from mono- or bicyclic saturated, unsaturated and/or aromatic radicals, which may contain up to five heteroatoms, e.g. N, S, or O, wherein each cyclic radical is 2- or 3-times substituted with —OH, —$OR_6$, and/or —$OCOR_6$.

Preferably, the other one of $R_3$ and $R_4$ may be H or $CH_3$, wherein H is preferred. The term "2- or 3-times substituted" means that the cyclic radical contains only 2 or only 3 above defined substituents (and no further substitutions).

$R_5$ is selected from
(i) H,
(ii) CN,
(iii) an acyclic radical selected from $C_{1-16}$ alkyl, $C_{2-16}$ alkenyl, $C_{2-16}$ alkynyl, wherein each acyclic radical is optionally mono- or poly-substituted with halo, —CN, —$NO_2$, =$NR_7$, —$N(R_7)_2$, —$N(R_7)_3{}^+$—$NR_5COR_7$, —$S(O)_nR_7$, $S(O)_nN(R_7)_2$, with n=0-3, —$OR_7$, $OCOR_7$, —$CON(R_7)_2$, —$COOR_7$, —$COR_7$, and/or a $C_{3-14}$ carbocyclic or heterocyclic moiety which may be substituted with halo, $C_nH_{2n}R_7$, with n=0-8, $OR_7$, CN, or
(iv) a $C_{3-14}$ carbocyclic or heterocyclic radical selected from mono- or bicyclic saturated, unsaturated and/or aromatic radicals which may contain up to 5 heteroatoms, e.g. N, S, or O, wherein each cyclic radical is optionally mono- or poly-substituted with $R_7$, halo, —CN, —$NO_2$, =$NR_7$, —$N(R_7)_2$, —$N(R_7)_3{}^+$, —$NR_7COR_7$, —$S(O)_nR_7$, $S(O)_nN(R_7)_2$, with n=0-3, —$OR_7$, $OCOR_7$, —$CON(R_7)_2$, —$COOR_7$, —$COR_7$, and/or a $C_{3-14}$ carbocyclic or heterocyclic moiety which may be substituted with halo, $C_nH_{2n}R_7$, with n=0-8, $OR_7$, CN, $R_6$ is selected from $C_{1-4}$ alkyl which may be optionally halogenated.

In one embodiment $R_6$ is selected from unsaturated $C_{1-4}$-alkyl.

$R_7$ is selected from an acyclic radical selected from $C_{1-16}$ alkyl, $C_{2-16}$ alkenyl, $C_{2-16}$ alkynyl, $C_{3-14}$ carbocyclic or heterocyclic radical selected from mono- or bicyclic saturated, unsaturated and/or aromatic radicals which may contain up to 5 heteroatoms, e. g. N, S, or O, wherein each acyclic and or cyclic radical is optionally mono- or poly-substituted with H, halo, —$NO_2$, —$NH_2$, —CN, —OH, —COOH, —COH, —$OCH_3$, —$OC_2H_5$, —$OC_3H_7$, —$COCH_3$, —$COC_2H_5$, —$OCOCH_3$, —$OCOC_2H_5$, $C_{1-3}F_{1-3}$ (haloalkyl), $C_{1-6}$ alkyl, $C_{2-8}$ alkenyl, $C_{2-8}$ alkynyl, —$C_6H_5SO_3{}^-$, —$SO_3{}^-$, —$C_5H_5NCH_3{}^-$, —$C_5H_5N^+O^-$, —$N(CH_3)_2{}^+$ and/or —$N(C_2H_5)_2{}^+$.

Preferably, one of $R_1$ and $R_2$ is a carbocyclic radical, i.e. an aryl, cycloalkyl, cycloalkenyl or cycloalkynyl radical, wherein at least one carbon atom may be replaced by a heteroatom, e.g. N, O or S.

In another embodiment, at least one of $R_1$ and $R_2$ is selected from aryl, preferably phenyl, or heterocyclyl, preferably benzothiazolyl, piperidinyl, pyrazolyl, pyridinyl, morpholinyl, piperazinyl, pyridazinyl, phthalazinyl, dihydroimidazolyl, quinolinyl, more preferably benzothiazolyl, quinolinyl, pyridinyl, phthalazinyl, dihydroimidazolyl, unsubstituted or mono- or polysubstituted with halo, e.g. Br, I, F and/or Cl, CN, $C_{1-3}$(halo)alkyl, particularly $CF_3$, $COOR_5$ and/or $NO_2$.

In another embodiment of the invention, N, $R_1$ and $R_2$ together form a heterocyclic radical selected from a monocyclic, saturated and/or aromatic radicals, which may contain up to five heteroatoms, particularly O, N, or S, more particularly O and/or N, wherein each heterocyclic radical is unsubstituted or mono- or fully substituted with $R_5$, —$S(O)_nR_5$ with n=0-3, a $C_{3-14}$ carbocyclic or heterocyclic moiety, preferably pyridinyl, which may be substituted with halo or $C_nH_{2n}R_5$ with n=0-8.

In one embodiment, preferably N, $R_1$ and $R_2$ together form a piperidinyl, pyrazolyl, morpholinyl or piperazinyl moiety.

In another embodiment, at least one of $R_1$ and $R_2$ is an acyclic radical selected from $C_{1-16}$-alkyl, wherein each acyclic radical is optionally mono- or polysubstituted with halo, CN, and/or a $C_{3-14}$ carbocyclic or heterocyclic moiety, preferably phenyl, which may be substituted with halo, $C_nH_{2n}R_5$, with n=0-8, $OR_5$, or CN.

In another embodiment, at least one of $R_1$ and $R_2$ is —$COR_5$.

More preferably, $R_1$ and $R_2$ is selected from aryl, e.g. phenyl, or heteroaryl, e.g. benzothiazolyl, unsubstituted or mono- or poly-substituted with halo, e.g. Br, I, F and/or Cl, CN, $C_{1-3}$ (halo)alkyl, e.g. $CF_3$ and/or $NO_2$.

In another embodiment, one of $R_1$ and $R_2$ is selected from phenyl or benzothiazolyl unsubstituted or substituted with
(i) $CF_3$
(ii) $CF_3$ and at least one Cl,
(iii) at least one of F, Br, Cl and/or —I
(iv) —CN and at least one of F or Cl,
(v) $NO_2$ and optionally $CF_3$, or
(vi) COOH.

Most preferably, one of $R_1$ and $R_2$ is selected from phenyl or benzothiazolyl unsubstituted or substituted with (i) —$CF_3$, (ii) —$CF_3$ and at least one —Cl, (iii) at least one of —F, —Br, —Cl, and/or —I, (iv) —CN and at least one —F or —Cl. In this context, it is further preferred that the other one of $R_1$ and $R_2$ is H, $C_{1-3}$ alkyl, e.g. methyl or aryl, e.g. phenyl.

In one embodiment, the other one of $R_1$ and $R_2$ is H, or $C_{1-3}$-alkyl, unsubstituted, mono- or polysubstituted with halo, —CN, —$NO_2$, =$NR_5$, —$N(R_5)_2$, —$N(R_5)_3^+$—$NR_5COR_5$, —$S(O)_nR_5$, $S(O)_nN(R_5)_2$, with n=0-3, —$OR_5$, $OCOR_5$, —$CON(R_5)_2$, —$COOR_5$, —$COR_5$, and/or a $C_{3-14}$ carbocyclic or heterocyclic moiety which may be substituted with halo, $C_nH_{2n}R_5$, with n=0-8, $OR_5$, CN; or aryl, particularly phenyl, optionally mono- or polysubstituted with $R_5$, halo, —CN, —$NO_2$, =$NR_5$, —$N(R_5)_2$, —$N(R_5)_3^+$, —$NR_5COR_5$, —$S(O)_nR_5$, $S(O)_nN(R_5)_2$, with n=0-3, —$OR_5$, $OCOR_5$, —$CON(R_5)_2$, —$COOR_5$, —$COR_5$, and/or a $C_{3-14}$ carbocyclic or heterocyclic moiety which may be substituted with halo, $C_nH_{2n}R_5$, with n=0-8, $OR_5$ or CN.

In another embodiment, the other one of $R_1$ and $R_2$ is H, or $C_{1-3}$-alkyl or phenyl.

In another embodiment, the other one of $R_1$ and $R_2$ is H, or $C_{1-3}$-alkyl.

In another embodiment, the other one of $R_1$ and $R_2$ is H or $CH_3$.

In another embodiment, the other one of $R_1$ and $R_2$ is H or phenyl.

It is preferred that at least one of $R_3$ and $R_4$ is selected from aryl, particularly phenyl, mono- or polysubstituted, particularly 2- or 3-times substituted with —OH and/or —$OR_6$.

It is preferred that at least one of $R_3$ and $R_4$ is selected from aryl, e.g. phenyl mono- or poly-substituted and preferably poly-substituted, e.g. 2- or 3 times substituted with OH. Especially preferred at least one of $R_3$ and $R_4$ is phenyl disubstituted or trisubstituted with OH.

In one embodiment, the other one of $R_3$ and $R_4$ is H or $CH_3$, wherein H is preferred.

In another embodiment, the other one of $R^3$ and $R^4$ is $CH_3$.

Further preferred are compounds of formula I, wherein one of $R_1$ and $R_2$ is phenyl substituted with $CF_3$ and/or with 1-5 halogen residues selected from Cl and/or F and the other one of $R_1$ and $R_2$ is H, $CH_3$ or phenyl, and wherein one of $R_3$ and $R_4$ is phenyl substituted with 1, 2 or 3 OH groups and the other one of $R_3$ and $R_4$ is H.

In another embodiment compounds of formula (I) are preferred, wherein one of $R_1$ and $R_2$ is phenyl substituted with $CF_3$ and/or with 1-5 halogen residues selected from Cl and/or F and the other one of $R_1$ and $R_2$ is H, $CH_3$ or phenyl, and wherein one of $R_3$ and $R_4$ is phenyl substituted with two or three OH and/or $OR_6$ groups, and the other one of $R_3$ and $R_4$ is H.

In another embodiment compounds of formula (I) are preferred, wherein one of $R_1$ and $R_2$ is phenyl substituted with $CF_3$ and/or with 1-5 halogen residues selected from Cl and/or F and the other one of $R_1$ and $R_2$ is H, $CH_3$ or phenyl, and wherein one of $R_3$ and $R_4$ is phenyl substituted with 2 or 3 OH groups and the other one of $R_3$ and $R_4$ is H.

In one embodiment, preferred are compounds selected from
1-(2,6-Dichloro-4-(trifluoromethyl)phenyl)-2-(2,4-dimethoxybenzylidene) hydrazine,
5-((2-(4-Fluorophenyl)hydrazono)methyl)benzene-1,2,4-triol,
4-((2-(4-Fluoro-phenyl)hydrazono)methyl)benzene-1,3-diol,
4-((2-(2,4-Difluorophenyl)hydrazono)methyl)benzene-1,3-diol,
5-((2-(2,4-Difluorophenyl)hydrazono)methyl)benzene-1,2,4-triol,
4-((2-(2,4-Difluorophenyl)hydrazono)methyl)benzene-1,2-diol,
4-((2-Phenylhydrazono)methyl)benzene-1,3-diol,
2-((2-Phenyl-hydrazono)methyl)phenol,
4-((2-(2-Chloro-4-(trifluoromethyl)phenyl)hydrazono)methyl)benzene-1,3-diol,
4-((2-(4-Iodophenyl)hydrazono)methyl)benzene-1,3-diol,
5-((2-(4-Iodophenyl)hydrazono)methyl)benzene-1,2,4-triol,
4-((2,2-Diphenylhydrazono)methyl)benzene-1,3-diol,
4-((2-Methyl-2-phenylhydrazono)methyl)benzene-1,3-diol,
5-((2-Methyl-2-phenylhydrazono)methyl)benzene-1,2,4-triol,
5-((2-Methyl-2-phenylhydrazono)methyl)benzene-1,2,4-triol,
4-((2-(4-Nitrophenyl)hydrazono)methyl)benzene-1,2-diol,
5-((2-(4-Nitrophenyl)hydrazono)methyl)benzene-1,2,4-triol,
4-((2-(4-Nitrophenyl)hydrazono)methyl)benzene-1,3-diol,
4-((Piperidin-1-ylimino)methyl)benzene-1,3-diol,
3-(2-(2,4-Dihydroxybenzylidene)hydrazinyl)propanenitrile
2-((2-Phenylhydrazono)methyl)phenol
4-((2-(4-(Trifluoromethyl)phenyl)hydrazono)methyl)phenol
4-((2-(2,6-Dichloro-4-(trifluoromethyl)phenyl)hydrazono)methyl)phenol
4-((2-(Benzo[d]thiazol-2-yl)hydrazono)methyl)phenol
1-(2,4-Dimethoxyphenyl)-2-(4-(trifluoromethyl)benzylidene)hydrazine
2-(2-(Pyridin-2-ylmethylene)hydrazinyl)quinoline
N'-(1-(2,4-Dihydroxyphenyl)ethylidene)-2-hydroxybenzohydrazide
2-Chloro-N'-(1-(2,4-dihydroxyphenyl)ethylidene)-4-nitrobenzohydrazide
N'-(1-(2,4-Dihydroxyphenyl)ethylidene)-3-iodobenzohydrazide
Most preferred are compounds
4-((2-(2,6-Dichloro-4-(trifluoromethyl)phenyl)hydrazono)methyl)benzene-1,3-diol,
1-(2,6-Dichloro-4-(trifluoromethyl)phenyl)-2-(2,4-dimethoxybenzylidene)hydrazine,
4-((2-(2,6-Dichloro-4-(trifluoromethyl)phenyl)hydrazono)methyl)benzene-1,2-diol, 4-((2-(4-(Trifluoromethyl)phenyl)hydrazono)methyl)benzene-1,3-diol,
4-((2-(4-(Trifluoromethyl)phenyl)hydrazono)methyl)benzene-1,2-diol,
5-((2-(4-Fluorophenyl)hydrazono)methyl)benzene-1,2,4-triol,
4-((2-(4-Fluorophenyl)hydrazono)methyl)benzene-1,3-diol,
3-((2-(4-Fluorophenyl)hydrazono)methyl)benzene-1,2-diol,
4-((2-(2,4-Difluorophenyl)hydrazono)methyl)benzene-1,3-diol,
5-((2-(2,4-Difluorophenyl)hydrazono)methyl)benzene-1,2,4-triol,
4-((2-(2,4-Difluorophenyl)hydrazono)methyl)benzene-1,2-diol,
4-((2-Phenylhydrazono)methyl)benzene-1,3-diol,
2-((2-Phenylhydrazono)methyl)phenol,
4-((2-(2,5-Dichlorophenyl)hydrazono)methyl)benzene-1,3-diol,
4-((2-(2-Chloro-5-(trifluoromethyl)phenyl)hydrazono)methyl)benzene-1,3-diol,
4-((2-(2-Chloro-phenyl)hydrazono)methyl)benzene-1,3-diol,
4-((2-(2,4-Dichlorophenyl)hydrazono)methyl)benzene-1,3-diol,
4-((2-(2-Chloro-4-(trifluoromethyl)phenyl)hydrazono)methyl)benzene-1,3-diol,
4-((2-(4-Iodophenyl)hydrazono)methyl)benzene-1,3-diol,
5-((2-(4-Iodophenyl)hydrazono)methyl)benzene-1,2,4-triol,
5-((2,2-Diphenylhydrazono)methyl)benzene-1,2,4-triol,
4-((2,2-Diphenylhydrazono)methyl)benzene-1,3-diol,
4-((2-(Perfluorophenyl)hydrazono)methyl)benzene-1,3-diol,
4-((2-(Perfluorophenyl)hydrazono)methyl)benzene-1,2-diol,
4-((2-Methyl-2-phenylhydrazono)methyl)benzene-1,2-diol,
4-((2-Methyl-2-phenylhydrazono)methyl)benzene-1,3-diol,
5-((2-Methyl-2-phenylhydrazono)methyl)benzene-1,2,4-triol,
3-Chloro-4-(2-(2,4,5-trihydroxybenzylidene)hydrazinyl)benzonitrile,
3-Chloro-4-(2-(2,4-dihydroxybenzylidene)hydrazinyl)benzonitrile,
3-Chloro-4-(2-(3,4-dihydroxybenzylidene)hydrazinyl)benzonitrile,
4-((2-(4-Nitrophenyl)hydrazono)methyl)benzene-1,2-diol,
5-((2-(4-Nitrophenyl)hydrazono)methyl)benzene-1,2,4-triol,
4-((2-(4-Nitrophenyl)hydrazono)methyl)benzene-1,3-diol,
4-((Piperidin-1-ylimino)methyl)benzene-1,3-diol,
4-((2-(Benzo[d]thiazol-2-yl)hydrazono)methyl)benzene-1,3-diol,
3-(2-(2,4-Dihydroxybenzylidene)hydrazinyl)propanenitrile,
2-((2-(4-(Trifluoromethyl)phenyl)hydrazono)methyl)benzene-1,3,5-triol
2-((2-(2,6-Dichloro-4-(trifluoromethyl)phenyl)hydrazono)methyl)benzene-1,3,5-triol
2-((2-(Benzo[d]thiazol-2-yl)hydrazono)methyl)benzene-1,3,5-triol
4-((2-Methyl-2-(2-nitro-4-(trifluoromethyl)phenyl)hydrazono)methyl)benzene-1,3-diol
4-((2-Methyl-2-(2-nitro-4-(trifluoromethyl)phenyl)hydrazono)methyl)benzene-1,2,3-triol
2-((2-Methyl-2-(2-nitro-4-(trifluoromethyl)phenyl)hydrazono)methyl)benzene-1,3,5-triol
4-((2-(Quinolin-2-yl)hydrazono)methyl)benzene-1,3-diol
5-((2-(Quinolin-2-yl)hydrazono)methyl)benzene-1,2,4-triol
4-((2-(Quinolin-2-yl)hydrazono)methyl)benzene-1,2,3-triol
5-((3-Mercapto-5-(pyridin-4-yl)-4H-1,2,4-triazol-4-ylimino)methyl)benzene-1,2,4-triol
5-((2-(5-Chloro-3-iodopyridin-2-yl)hydrazono)methyl)benzene-1,2,4-triol
4-((Morpholinoimino)methyl)benzene-1,2,3-triol
4-(2-(3,4-Dihydroxybenzylidene)hydrazinyl)benzoic acid
5-((4-Methylpiperazin-1-ylimino)methyl)benzene-1,2,4-triol
5-((2-(6-Chloropyridazin-3-yl)hydrazono)methyl)benzene-1,2,4-triol
5-((2-(Phthalazin-1-yl)hydrazono)methyl)benzene-1,2,4-triol
5-((2-(4,5-Dihydro-1H-imidazol-2-yl)hydrazono)methyl)benzene-1,2,4-triol
4-((2-Benzyl-2-methylhydrazono)methyl)benzene-1,2-diol
4-((2-(5-(4-Methoxyphenylamino)pyridin-2-yl)hydrazono)methyl)benzene-1,3-diol
4-((2-(4-(4-Methoxyphenylamino)phenyl)hydrazono)methyl)benzene-1,3-diol
4-((2-(4-(4-Methoxybenzyl)thiazol-2-yl)hydrazono)methyl)benzene-1,3-diol
N'-(1-(2,4-Dihydroxyphenyl)ethylidene)-2-hydroxybenzohydrazide
2-Chloro-N'-(1-(2,4-dihydroxyphenyl)ethylidene)-4-nitrobenzohydrazide
N'-(1-(2,4-Dihydroxyphenyl)ethylidene)-3-iodobenzohydrazide.
1-(4-Cyanophenyl)-N'-(2,4-dihydroxybenzylidene)piperidine-4-carbohydrazide
N'-(2,4-Dihydroxybenzylidene)-2-phenylacetohydrazide.

In a preferred embodiment, within a compound of formula I, the hydrogen of at least one —NH and/or =CH group, e.g. at least one —CH group of an aromatic radical as defined above, may be replaced by deuterium atoms. Preferably, the average degree of deuterization (number of deuterium atoms/(number of deuterium+hydrogen atoms)× 100) in the molecule is at least 50-100%, preferably 60-100%, more preferably 70-100%, more preferably 80-100%, more preferably 95-100%, and most preferably 96-99%.

Further, it is preferred that a compound of formula I as defined above is present in isomeric pure form, wherein "isomeric pure" means that a preparation of the compound comprises more than 90%, preferably more than 95%, more preferably more than 98% and most preferably more than 99% of one defined isomer of said compound compared to the total amount of said compound.

In one embodiment a compound of formula I as described herein is present as a salt. Preferred is a salt which is soluble in an aqueous solution.

Therefore, the salt may be in the form of a metal salt. The metal may be selected from a transition metal, preferably from the group consisting of Fe, V, Mo, Ni, Cu, Co, Zn. The oxidation state of the metal may be −2, −1, 0, +1, +2, +3, +4, +5 or +6 depending on the metal used. Mostly preferred is Fe in the oxidation state +2 and/or +3,
Ni, Cu, Co, Zn in the oxidation state +2,
Mo in the oxidation state +4 and/or +6,
V in the oxidation state +5.

The present invention further provides a composition comprising at least one compound of formula I as described above, wherein in a preferred embodiment at least one of said compounds is present in an isomeric pure form.

In general, hydrazones of present formula I are synthesized by reacting an appropriate hydrazine of formula II

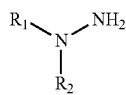

with an aldehyde of formula III

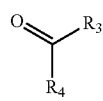

wherein $R_1$-$R_4$ are as defined above, at a temperature of between 10-100° C., preferably 20-80° C. The molar ratio of aldehyde and hydrazine is from 1:10 to 10:1, preferred is a substantially 1:1 (equimolar) ratio. The reaction is carried out in an organic solvent, preferably alkanol. Especially preferred is absolute ethanol.

A few hydrazones are known to be instable in aqueous solutions. Thus, hydrazones in aqueous solution are in equilibrium with hydrazine and aldehyd, the equilibrium being shifted towards hydrazine and aldehyde. It was therefore another object of the present invention to stabilize hydrazones in aqueous solutions and to provide aqueous compositions comprising at least one hydrazone compound of formula I as described above, wherein the hydrazone is stabilized, i.e. protected from decomposition.

Surprisingly, it was found by the present inventors that an addition of a stabilizing agent selected from amino acids, peptides, polypeptides, proteins, proteids and/or transition metal ions to an aqueous solution of a compound of formula I, does dramatically increase the stability of the hydrazone compound. Therefore, the present invention provides a method of stabilizing a compound of formula I within an aqueous solution comprising adding to the solution a stabilizer selected from amino acids, peptides, polypeptides, proteins, proteids or transition metal ions or combinations thereof. Suitable amino acids, peptides and polypeptides are for example naturally occurring proteinogenic and/or non-proteinogenic amino acids or (poly-)peptides, respectively, which optionally can be modified. Preferred are the water-soluble proteinogenic amino acids. Suitable (poly-)peptides are naturally occurring water-soluble peptides having a sequence length of 2-100 amino acids, each of which can be further modified. Preferred stabilizing agents are naturally occurring proteins, preferably globular proteins, each of which can be further modified. Especially preferred is a serum albumin, e.g. bovine serum albumin (BSA). Preferred transition metal ions are Fe, Cu, Zn, Ni, Mo, Co. In one embodiment, stabilizers are used in sub-equimolar ratios compared to hydrazone, i.e. in a molar ratio between stabilizer and hydrazone of <1:1. Suitable molar ratios of stabilizing agent to hydrazone are 0.001:1, preferably 0.01:1. Mostly preferred, the molar ratio of stabilizing agent to hydrazone is 0.1:1.

The invention further provides a composition comprising at least one hydrazone compound of formula I as described above, wherein the hydrazone is stabilized. In this context, "stabilized" preferably means that the content of hydrazone within a composition is decreased over a period of 24 hours after formulating said composition, e.g. by dissolving hydrazone, by less than 20%, preferably less than 10%, and more preferably less than 5%.

In other words, a stabilized composition according to the invention is one, in which after a time period of 24 hours after its formulation, e.g. by dissolving hydrazone, at least 80%, preferably at least 90%, and more preferably at least 95% of hydrazone is present, given that the content of hydrazone dissolved at time point 0 hours is set to 100%.

As mentioned above, the compounds and compositions according to the invention can be used according to another aspect of the invention for
(i) modulating the processing, e.g. mediating, activating or enhancing degradation of proteins which are misfolded, tend to be misfolded and/or form toxic aggregates,
(ii) preventing misfolding of proteins,
(iii) inhibiting accumulation of misfolded proteins, and/or
(iv) decomposing cytotoxic aggregates, e.g. formed by or mainly comprising misfolded proteins.

One group of targets for the compounds of formula I as described herein comprises protein species which are characterized by the presence of a poly-Q stretch, i.e. an amino acid sequence of more than 15, preferably more than 20, 27, more preferably more than 35 and most preferably more than 50 contiguous glutamine residues within their primary structures, and by misfolding of said poly-Q-stretch. Exemplary proteins having a poly-Q-stretch which may be subjected to misfolding are Androgen receptor, Ataxin-1, Ataxin-2, Ataxin-3, CACNA1A, Ataxin-7, TATA-binding protein, Atrophin-1 and htt. A preferred target protein is a mutated variant of a wildtype form of a protein listed above, wherein compared to the wildtype form the mutated variant has an expanded poly-Q-stretch and wherein said mutated variant is subjected to misfolding due to the expansion of the poly-Q-stretch. An example of a preferred target protein is htt or a toxic variant of htt like mhtt.

Therefore, according to a further aspect of the invention, the compounds of formula I as described herein can be used for mediating, activating or enhancing degradation of a protein having a poly-Q-stretch as defined above, e.g. aberrant htt or mhtt, and/or decomposition of aggregates formed by or mainly comprising a protein species having a poly-Q-stretch, e.g. mhtt, when applied to cells expressing said protein species.

Without being limited to a specific mode of action it was found out by the present inventors that hydrazone compounds of formula I are able to interact or directly interact, respectively, with pathologically misfolded protein molecules or protein molecules having a tendency to be misfolded leading to conformational changes of said protein molecules allowing them to undergo degradation or preventing them from misfolding. Moreover, it was surprisingly found that the hydrazone compounds of formula I as described herein do not influence formation of proteinaceous structures as for example tubulin polymerization necessary for cell viability (i.e. they are non-toxic) when applied in concentrations effecting degradation of misfolded proteins and aggregates thereof or prevention of protein misfolding. In other words, the hydrazone compounds according to the present invention are selective for misfolded proteins, proteins having a tendency to be subjected to misfolding and aggregates thereof.

According to the invention, the compounds of formula I as described herein or a composition comprising at least one compound of formula I as the active ingredient can be used as a medicament for treating, alleviating and/or preventing conditions associated with and/or caused by protein misfolding and/or accumulation of (misfolded) proteins. Non-limiting examples of conditions or diseases within the context of the invention are Huntington's disease (HD), spinobulbar muscular atrophy (Kennedy disease), dentato-rubral-pallidoluysian atrophy (Haw River syndrome), spinocerebellar ataxia type 1, spinocerebellar ataxia type 2, spinocerebellar ataxia type 3 (Machado-Joseph disease), spinocerebellar ataxia type 6, spinocerebellar ataxia type 7, spinocerebellar ataxia type 17, Alzheimer's disease, Parkinson's disease, primary systemic amyloidosis, secondary systemic amyloidosis, senile systemic amyloidosis, familial amyloid polyneuropathy 1, hereditary cerebral amyloid angiopathy, hemodialysis-related amyloidosis, familial amyloid polyneuropathy Ill, Finnish hereditary systemic amyloidosis, type 2 diabetes, medullary carcinoma of thyroid, atrial amyloidosis, hereditary non-neuropathic systemic amyloidosis, injection-localized amyloidosis, hereditary renal amyloidosis, amyotrophic lateral sclerosis, schizophrenia, sickle cell anaemia, unstable haemoglobin inclusion body haemolysis, al-antitrypsin deficiency, antithrombin deficiency, thromboembolic disease, Transmissible spongiform encephalopathies (prion diseases): bovine spongiform encephalopathy, kuru, Gerstmann-Straeussler-Scheinker syndrome, fatal familial insomnia, scrapie, Creutzfeldt-Jakob disease, variant Creutzfeldt-Jakob disease.

In one preferred embodiment the compounds of formula I as described herein or a composition comprising at least one compound of formula I can be used as a medicament for treating, alleviating and/or preventing diseases, the causative agent of which is a pathological intracellular amount of a misfolded protein species having a poly-Q-stretch as defined above. More preferably, the condition is caused by cytotoxic accumulation of htt or expression of mhtt. Most preferably, a compound of formula I or a composition as described herein, is for HD therapy and/or preventing symptoms accompanying said disease.

For use as a medicament, the compound according to the invention may be formulated as a pharmaceutical composition with pharmaceutically acceptable diluents and/or carriers known in the art. Optionally, the composition may contain other active ingredients suitable for treating symptoms coinciding with pathological protein misfolding and accumulation. In case of treating HD symptoms, such additional active ingredients may be selected from psychoactive agents as for example antipsychotics, antidepressants and mood stabilizers. The content of the at least one hydrazone compound of formula I as described herein, within the pharmaceutical composition can vary over a broad range. Preferably, the hydrazone concentration per dosage unit is about 0.1 mg-1000 mg or higher. The dosage can be administered all in one administration per day or partially several times per day.

The medicament comprising a compound of formula I as described above can be formulated to be suitable for any known dosage form. Thus, the pharmaceutical formulation according to the invention can be in the form of a solution, syrup, suspension, tablet, powder, capsule, aerosol, suppository, creme, lotion, ointment, gel or patch for topical, transdermal, enteral (e.g. orally, rectally or by feeding tube) or parenteral (e.g. by intravenous, intraarterial, intramuscular, subcutaneous, intrathecal, interperitoneal injection or infusion) application. Preferably, the medicament is formulated as an aqueous solution for parenteral application. More preferably, the medicament comprises at least one stabilizing agent e.g. selected from amino acids, peptides, polypeptides, proteins, proteids and/or transition metal ions for stabilizing a compound of formula I, and optionally further agents suitable for treating HD symptoms as defined above. Further, the pharmaceutical composition is preferably in the form of an aqueous solution comprising at least one compound of formula I as the active ingredient and a serum albumin, e.g. BSA as the stabilizing agent. In one preferred embodiment, the compound of formula I is present in an isomeric pure form.

In a further aspect, the present invention provides a method for modulating protein processing, e.g. degrading misfolded proteins or aggregates thereof and inhibiting protein misfolding or pathological accumulation of proteins comprising administration of a compound of formula I, or a composition comprising at least one of said compounds as described above to a eukaryotic or prokaryotic cell, cell culture, cell tissue or subject containing said proteins or aggregates. The cell or subject may be homozygous or heterozygous for at least one of said proteins, preferably heterozygous. Preferably, the protein is mhtt and the cell, cell culture, cell tissue or subject expresses mhtt. In one embodiment, the cell or subject expresses mhtt as well as htt, i.e. said cell or subject is heterozygous for mhtt.

Especially preferred is a method for modulating mhtt processing, wherein the mhtt protein itself and/or protein aggregates comprising mhtt are degraded or decomposed and wherein said degradation or decomposition is mediated by a compound of formula I as described above.

The method according to the invention can be carried out in vivo as well as in vitro.

In a further aspect, the present invention relates to a method for treating and/or preventing conditions caused by expression of proteins showing a tendency to misfolding and/or aggregate formation, e.g. htt or mhtt, comprising administration of a compound of formula I or a composition comprising said compound as described above to a subject in need thereof. In one embodiment, the conditions to be treated and/or prevented are characteristic for a disease, the causative agent of which is mhtt. Especially, the conditions are characteristic for HD.

Another aspect of the present invention refers to a kit for modulating processing of proteins showing a tendency to misfolding and/or aggregate formation, e.g. htt and/or mhtt. The kit comprises at least one compound of formula I as defined above and optionally means for detecting protein processing, e.g. htt and/or mhtt protein processing.

The invention will be described in further detail by the following Figures and Examples.

DESCRIPTION OF FIGURES

FIG. 1 illustrates the general synthesis of arylated and alkylated hydrazones comprised by formula I (product examples 1-67) from various hydrazines (68-99) and aldehydes (100-108) and the combination of the used educts.

FIG. 2 illustrates the structures of the hydrazine (68-99) and aldehyde (100-108) used to synthesize hydrazones according to the invention (product examples 1-67).

EXAMPLE 1

Synthesis of Hydrazones

The synthesis of alkyl/aryl and bisaryl hydrazones was carried out in ethanol at ambient temperature under dry conditions as described in FIG. 1. An equimolar ratio of aldehyde and hydrazine was used for the hydrazones in hydrazines preparation. 32 hydrazones and 9 aldehydes were condensed in selected combinations to 59 hydrazones (FIG. 2). The reaction times differ between 16 to 24 hours. In some cases the precipitated products were directly separated from the reaction mixture by filtration. The rest of the compounds were separated per filtration after varied treatments with different organic solvents. Based on the hydrazine consumption, yields from 10% to 97% were achieved (see experimental). For the vast majority of compounds, purities (RP-HPLC) from >96% were confirmed. In five cases (example 12, 14, 32, 56, 57) a purity from 64-80% was ascertained. In three cases (example 12, 14, 32) a purity from 66-80% was ascertained. All compounds were characterized by 1H- and 13C-MNR and GC-MS measurements (see experimental).

EXAMPLE 2

Stability of Hydrazones

Figure 3:
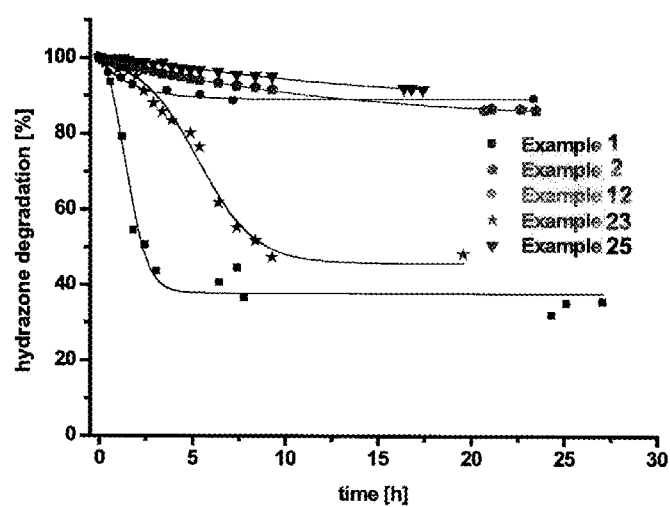
FIG. 3 illustrates the stability of hydrazone compounds according to the invention (product examples 1, 2, 12, 23 and 25) in a concentration of 20 μM in an aqueous ammonium acetate solution (10 mM).

The stability of hydrazones was estimated in a 10 mM ammonium acetate solution at room temperature (FIG. 3). Freshly prepared 10 mM methanol solutions of product examples 1, 2, 12, 23 and 25 were diluted in a 10 mM ammonium acetate solution to a final concentration of 20 µM. These solutions were analyzed via RP-HPLC over a sample period of 24 h. The injection volume was 20 µL, the sample was stored at room temperature. The hydrazone peak was exploited for the determination of the hydrazone concentration. Depending on the substitution pattern, strong distinctions were observed. For all analyzed compounds an equilibration was detectable. Through the allowance of organic solvents and proteins, or transition metal ions in subequimolar ratios, the stability of the labile compounds dramatically increased. The level of the establishment of equilibrium for such instable compounds was raised to a level, where only small traces from the hydrazines and aldehydes were detectable.

Figure 4:
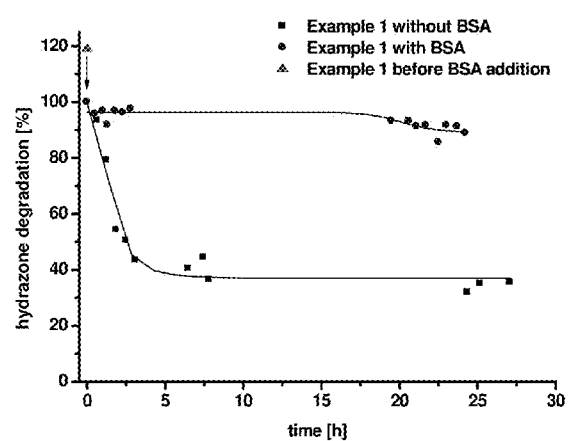
FIG. 4 illustrates the stability of a hydrazone compound according to the invention (product example 1) in the presence of BSA in a submolar ratio.

FIG. 4 illustrates the difference in the hydrazone hydrolysis with and without the addition of BSA of product example 1. A freshly prepared 10 mM methanol solution of product example 1 was diluted with an ammonium acetate (10 mM) BSA (5 µM) solution to a final concentration of 20 µM. The free soluble hydrazone was analyzed via RP-HPLC over a sample period of 24 h. The injection volume was 20 µL, the sample was stored at room temperature. The hydrazone peak was exploited for the determination of the hydrazone concentration. After the addition of BSA approximately 17% of the available hydrazone was directly associated to the protein. Afterwards, the free hydrazone concentration was almost constant, between 96% and 91%, over the sample period.

EXAMPLE 3

Hydrazones 3.1 General Synthetic Methods

All chemicals were purchased from commercial suppliers and used without further purification. The reaction was monitored by thin-layer chromatography on silica gel 60 $F_{254}$ coated aluminium sheets (Merck KGaA). All filtration was performed using a Büchner funnel with filter circles MN 615 and MN 640 (Macherey-Nagel). NMR spectra were recorded on Bruker Avance 300 MHz spectrometer. Chemical shifts are reported in parts per million downfield from the internal standard Tetramethylsilane (0.0 ppm) for $^1$H-NMR and $^{13}$C-NMR spectra. All samples were measured in $d_6$-DMSO. The high performance liquid chromatography (HPLC) measurements were carried out on an Agilent System from the 1200 Series including binary pump, auto sampler and diode array detector. A Chromolith RP-18 SpeedRod column (50 mm×4.6 mm) was used for the analytical reverse phase HPLC analysis (Merck KGaA, model 1.51450.0001). For the evaluation of the syn-anti isomerism an Ascentis RP-Amide column (100 mm×3.0 mm, 3 µm particle size, Supelco, model 565312-U) and a Astec Cyclobond I 2000 DNP column (250 mm×4.6 mm, 5 µm particle size, Supelco, model 25042AST) was used. Solvent A was 10 mM ammonium acetate solution and solvent B was acetonitrile. The following running conditions were used: a) B: 70%, 0-10 min, flow 0.7 mL/min; b) B: 40% (0 min)→60% (8 min)→100% (10 min), flow 1.0 mL/min; c) B: 50% (0 min)→70% (8 min)→100% (10 min), flow 1.0 mL/min; d) B: 40% (0 min)→70% (8 min)→100% (10 min), flow 0.8 mL/min; e) B: 40%, 0-10 min, flow 1.0 mL/min; f) B: 40%, 0-10 min, flow 0.65 mL/min; g) B: 50% (0-8 min)→100% (10 min), flow 0.5 mL/min; h) B: 50%, 0-10 min, flow 1.0 mL/min; i) B: 20% (0 min)→60% (8 min)→100% (10 min), flow 0.5 mL/min; j) B: 30% (0 min)→50% (8 min)→100% (10 min), flow 1.0 mL/min; k) B: 30% (0 min)→70% (8 min)→100% (10 min), flow 1.0 mL/min; l) B: 40% (0 min)→70% (8 min)→100% (10 min), flow 1.0 mL/min; m) B: 50% (0 min)→70% (8 min)→100% (10 min), flow 1.2 mL/min; n) B: 5% (0 min)→40% (8 min)→100% (10 min), flow 0.9 mL/min; o) B: 25% (0 min)→50% (8 min)→100% (10 min), flow 1.0 mL/min; p) B: 0% (0 min)→10% (8 min)→100% (10 min), flow 1.0 mL/min. All runs were performed at 43° C. All mass spectrometry data were collected at IntraServ GmbH & Co. Knapsack KG and ChiroBlock GmbH. The Uv-vis spectra were recorded with a SPECORD 250 spectrometer from Analytik Jena AG. All spectra were collected in water containing 2% Acetonitril.

3.2 General Synthesis of Hydrazones

An equimolar ratio of aldehyde and hydrazine was stirred for 24-48 h in absolute ethanol under dry conditions at ambient temperature. The product was dried at 75° C. for 15-24 h.

3.3 Hydrazine Preparation

Hydrazines, which are only available as hydrochloride, were stirred in a saturated aqueous $NaHCO_3$ solution for 1 h. The free hydrazine was extracted twice with ethyl acetate, the organic layers were combined, dried with $Na_2SO_4$ and the solvent evaporated. The resulting oil was dried under reduced pressure at 50° C. for 2 h.

3.4 Purification

Method 1

The solid product was separated with a Büchner funnel and washed with cool ethanol.

Method 2

The reaction was quenched with the 5-7-fold volume of cyclohexane. The organic solvents were removed under reduced pressure. The product starts to precipitate at the sixth of the starting volume. The distillation was stopped and the batch stored at 15° C. for 1 h. The product was separated with a Büchner funnel and washed with cyclohexane.

Method 3

Ethanol was removed under reduced pressure. The crude product was resolved in diethyl ether (1 part) and diluted with 4-6 parts of cyclohexane. The vast majority of diethyl ether and parts of cyclohexane were removed under reduced pressure, until the product starts to precipitate. The distillation was stopped and the batch stored at 15° C. for 1 h. The product was separated with a Büchner funnel and washed with cyclohexane.

Method 4

Ethanol was removed under reduced pressure. The crude product was resolved in ethyl acetate. The organic phase was washed twice with water. The organic layer was dried with $Na_2SO_4$ and the solvent removed.

Method 5

Solid impurities were separated with a Büchner funnel. The filtrate was diluted with n-hexane. The product starts to crystallized after a few minutes. The batch was stored at room temperature for 1 h; the product was separated with a Büchner funnel and washed with n-hexane.

Method 6

Ethanol was removed under reduced pressure. The crude product was resolved in diethyl ether (1 part) and diluted with 4-6 parts of cyclohexane. The vast majority of diethyl ether and parts of cyclohexane was removed under reduced pressure, until the product starts to refine as oil. The distillation was stopped and the batch stored at room temperature for 1 h. The oil phase was separated, washed twice with cyclohexane and dried under reduced pressure at 50° C. for 2 h. The oil starts to crystallize after several hours at room temperature.

Method 7

The reaction solution was poured on crushed ice. The precipitated product was separated with a Büchner funnel and washed with a mixture of ethanol and water (1:4).

Method 8

Ethanol was removed under reduced pressure. The crude product was resolved in diethyl ether (1 part) and diluted with 10 parts of n-hexane. The solution was treated in an ultrasonic bath. The product precipitated rapidly. It was separated with a Büchner funnel and washed with n-hexane.

Method 9

The reaction solution was diluted with a mixture of methanol and water (1:2). The product was extracted once with ethyl acetate, the organic layer was washed twice with water and dried with $Na_2SO_4$. The solvent was removed under reduced pressure.

Method 10

Ethanol was removed under reduced pressure. The crude product was resolved in ethyl acetate (1 part) and diluted with 10 parts of cyclohexane. The organic solvents were removed under reduced pressure. The product starts to precipitate at the fourth to sixth of the starting volume. The distillation was stopped and the batch stored at 20° C. for 1 h. The product was separated with a Büchner funnel and washed with cyclohexane.

Method 11

Ethanol was removed under reduced pressure. The product starts to precipitate at the sixth of the starting volume. The distillation was stopped and the batch stored at 5° C. for 1 h. The product was separated with a Büchner funnel and washed with a mixture of cyclohexane and diethyl ether (6:4).

3.5 Product Examples 1-67

EXAMPLE 1

4-((2-(2,6-Dichloro-4-(trifluoromethyl)phenyl)hydrazono)methyl)benzene-1,3-diol (2,6-Dichloro-4-(trifluoromethyl)phenyl)hydrazine (200 mg, 0.8 mmol), 2,4-Dihydroxybenzaldehyde (113 mg, 0.8 mmol);

Purification: Method 3; Yield: 265 mg, 89%; $C_{14}H_9Cl_2F_3N_2O_2$, M=365.13 g/mol $^1$H-NMR (300 MHz, $d_6$-DMSO) ppm: 6.29 (d, 1H, J=1.5 Hz), 6.33 (dd, 1H, J=1.9 Hz, J=8.5 Hz), 7.25 (d, 1H, J=8.4 Hz), 7.81 (s, 2H), 8.41 (s, 1H), 9.75 (s, 2H), 10.42 (s, 1H); $^{13}$C-NMR (75 MHz, $d_6$-DMSO) ppm: 102.98, 108.14, 111.58, 122.49 (q, $J_{C-F}$=33.7 Hz), 123.53 (d, $J_{C-F}$=271.9 Hz), 123.57, 127.18 (q, $J_{C-F}$=3.8 Hz), 130.66, 141.551, 145.27, 158.72, 160.36; GC-MS 364 m/z [M−H]$^+$; Purity: 98.9% (324 nm, $t_r$=3.89 min, Method: c)

EXAMPLE 2

1-(2,6-Dichloro-4-(trifluoromethyl)phenyl)-2-(2,4-dimethoxybenzylidene)hydrazine (2,6-Dichloro-4-(trifluoromethyl)phenyl)hydrazine (200 mg, 0.8 mmol), 2,4-Dimethoxybenzaldehyde (136 mg, 0.8 mmol);

Purification: Method 1; Yield: 197 mg, 61%; $C_{16}H_{13}Cl_2F_3N_2O_2$, M=393.19 g/mol $^1$H-NMR (300 MHz, $d_6$-DMSO) ppm: 3.80 (s, 3H), 3.85 (s, 3H), 6.59 (dd, 1H, J=2.6 Hz, J=11.2 Hz), 6.1 (d, 1H, J=3.0 Hz), 7.72 (d, 1H, J=8.5 Hz), 7.77 (s, 2H), 8.50 (s, 1H), 9.88 (s, 1H); $^{13}$C-NMR (75 MHz, $d_6$-DMSO) ppm: 55.28, 55.62, 98.16, 106.27, 115.89, 121.39 (q, $J_{C-F}$=33.7 Hz), 122.96, 123.05 (d, $J_{C-F}$=271.7 Hz), 125.89, 126.51 (q, $J_{C-F}$=3.7 Hz), 137.98, 141.49, 158.18, 161.51; GC-MS 392 m/z [M−H]$^+$; Purity: 92.0% (372 nm, $t_r$=4.68 min, Method: a)

EXAMPLE 3

4-((2-(2,6-Dichloro-4-(trifluoromethyl)phenyl)hydrazono)methyl)benzene-1,2-diol (2,6-Dichloro-4-(trifluoromethyl)phenyl)hydrazine (300 mg, 1.2 mmol), 3,4-Dihydroxybenzaldehyde (169 mg, 1.2 mmol);
Purification: Method 3; Yield: 322 mg, 72%; $C_{14}H_9Cl_2F_3N_2O_2$, M=365.13 g/mol
$^1$H-NMR (300 MHz, $d_6$-DMSO) ppm: 6.76 (d, 1H, J=8.1 Hz), 6.87 (dd, 1H, J=1.7 Hz, J=8.1 Hz), 7.15 (d, 1H, J=1.7 Hz), 7.79 (s, 2H), 8.10 (s, 1H), 9.13 (s, 1H), 9.22 (s, 1H), 9.69 (s, 1H); $^{13}$C-NMR (75 MHz, $d_6$-DMSO) ppm: 112.19, 115.48, 119.18, 121.32 (q, $J_{C-F}$=33.4 Hz), 122.82, 123.06 (d, $J_{C-F}$=271.8 Hz), 126.40, 126.53 (q, $J_{C-F}$=3.7 Hz), 141.43, 143.09, 145.53, 146.98; GC-MS 364 m/z[M–H]$^+$; Purity: 98.5% (326 nm, $t_r$=3.08 min, Method: c)

EXAMPLE 4

4-((2-(4-(Trifluoromethyl)phenyl)hydrazono)methyl)benzene-1,3-diol (4-(Trifluoromethyl)phenyl)hydrazine (200 mg, 1.1 mmol), 2,4-Dihydroxybenzaldehyde (156 mg, 1.1 mmol);
Purification: Method 2; Yield: 269 g, 80%; $C_{14}H_{11}F_3N_2O_2$, M=296.24 g/mol
$^1$H-NMR (300 MHz, $d_6$-DMSO) ppm: 6.33-6.36 (m, 2H), 7.05 (d, 2H, J=8.5 Hz), 7.41 (d, 1H, J=9.1 Hz), 7.54 (d, 2H, J=8.6 Hz), 8.15 (s, 1H), 9.72 (s, 1H), 10.38 (s, 1H), 10.57 (s, 1H); $^{13}$C-NMR (75 MHz, $d_6$-DMSO) ppm: 102.50, 107.69, 111.05, 111.95, 117.96 (q, $J_{C-F}$=31.9 Hz), 125.05 (d, $J_{C-F}$=270.3 Hz), 125.54 (q, $J_{C-F}$=3.5 Hz), 128.78, 140.23, 148.03, 157.57, 159.51; GC-MS 296 m/z [M]$^+$; Purity: 100.0% (342 nm, $t_r$=2.89 min, Method: d)

EXAMPLE 5

4-((2-(4-(Trifluoromethyl)phenyl)hydrazono)methyl)benzene-1,2-diol (4-(Trifluoromethyl)phenyl)hydrazine (1.2 g, 6.8 mmol), 3,4-Dihydroxybenzaldehyde (940 mg, 6.8 mmol); Purification: Method 6 or 8;
Yield: 1.789 g, 89%; $C_{14}H_{11}F_3N_2O_2$, M=296.24 g/mol
$^1$H-NMR (300 MHz, $d_6$-DMSO) ppm: 6.76 (d, 1H, J=8.1 Hz), 6.90 (dd, 1H, J=1.8 Hz, J=8.2 Hz), 7.12 (d, 2H, J=8.5 Hz), 7.19 (d, 1H, J=1.8 Hz), 7.52 (d, 2H, J=8.6 Hz), 7.79 (s, 1H), 9.10 (s, 1H), 9.20 (s, 1H), 10.49 (s, 1H);
$^{13}$C-NMR (75 MHz, $d_6$-DMSO) ppm: 111.16, 112.10, 115.51, 117.60 (q, $J_{C-F}$=31.86 Hz) 118.94, 125.05 (d, $J_{C-F}$=270.2 Hz) 126.35 (q, $J_{C-F}$=3.5 Hz), 126.67, 139.86, 145.54, 146.63, 148.49; GC-MS 296 m/z[M]$^+$; Purity: 99.8% (344 nm, $t_r$=3.67 min, Method: h)

EXAMPLE 6

5-((2-(4-Fluorophenyl)hydrazono)methyl)benzene-1,2,4-triol (4-Fluorophenyl)hydrazine (236 mg, 1.9 mmol), 2,4,5-Trihydroxybenzaldehyde (288 mg, 1.9 mmol); Purification: Method 2; Yield: 402 mg, 82%; $C_{13}H_{11}FN_2O_3$, M=262.24 g/mol
$^1$H-NMR (300 MHz, $d_6$-DMSO) ppm: 6.30 (s, 1H), 6.88 (t, 3H, J=6.8 Hz), 7.05 (t, 2H, J=8.8 Hz), 7.97 (s, 1H), 8.38 (s, 1H), 9.20 (s, 1H), 9.81 (s, 1H), 9.98 (s, 1H); $^{13}$C-NMR (75 MHz, $d_6$-DMSO) ppm: 103.35, 111.03, 112.29 (d, $J_{C-F}$=7.5 Hz), 113.12, 115.57 (d, J=22.3 Hz), 138.30, 141.96 (d, $J_{C-F}$=1.7 Hz), 147.12, 149.59, 153.48 (d, $J_{C-F}$=233.5 Hz); GC-MS 262 m/z [M]$^+$; Purity: 100.0% (350 nm, $t_r$=2.69 min, Method: f)

EXAMPLE 7

4-((2-(4-Fluorophenyl)hydrazono)methyl)benzene-1,3-diol (4-Fluorophenyl)hydrazine (202 mg, 1.6 mmol), 2,4-Dihydroxybenzaldehyde (221 mg, 1.6 mmol); Purification: Method 1; Yield: 35 mg, 89%; $C_{13}H_{11}FN_2O_2$, M=246.24 g/mol
$^1$H-NMR (300 MHz, $d_6$-DMSO) ppm: 6.28-632 (m, 2H), 6.88 (t, 2H, J=6.6 Hz), 7.06 (t, 2H, J=8.8), 7.28 (d, 1H, J=10.9 Hz), 8.03 (s, 1H), 9.64 (s, 1H), 10.05 (s, 1H), 10.60 (s, 1H); $^{13}$C-NMR (75 MHz, $d_6$-DMSO) ppm: 102.42, 107.42, 111.95, 112.40 (d, $J_{C-F}$=8.2 Hz), 115.65 (d, $J_{C-F}$=22.4 Hz), 128.92, 139.09, 141.78 ($J_{C-F}$=1.7 Hz), 155.62 ($J_{C-F}$=233.7 Hz), 157.36, 158.92; GC-MS 246 m/z [M]$^+$; Purity: 97.7% (338 nm, $t_r$=1.49 min, Method: c)

EXAMPLE 8

3-((2-(4-Fluorophenyl)hydrazono)methyl)benzene-1,2-diol (4-Fluorophenyl)hydrazine (267 mg, 2.1 mmol), 2,3-Dihydroxybenzaldehyde (292 mg, 2.1 mmol); Purification: Method 2; Yield: 218 mg, 42%; $C_{13}H_{11}FN_2O_2$, M=246.24 g/mol
$^1$H-NMR (300 MHz, $d_6$-DMSO) ppm: 6.70 (t, 1H, J=7.7 Hz), 6.76 (dd, 1H, J=7.8 Hz, J=1.7 Hz), 7.03-6.91 (m, 3H), 7.11 (t, 2H, J=8.9 Hz), 8.12 (s, 1H), 9.18 (s, 1H), 10.06 (s, 1H), 10.35 (s, 1H); $^{13}$C-NMR (75 MHz, $d_6$-DMSO) ppm: 112.64 (d, $J_{C-F}$=7.6 Hz), 115.38, 115.73 (d, $J_{C-F}$=22.2 Hz), 117.85, 119.10. 120.66, 138.05, 141.42 (d, $J_{C-F}$=1.8 Hz), 144.09, 145.29, 155.86 (d, $J_{C-F}$=234.32 Hz); GC-MS 246 m/z [M]$^+$; Purity: 100.0% (310 nm), 100.0% (342 nm, $t_r$=2.64 min, Method: e)

EXAMPLE 9

4-((2-(2,4-Difluorophenyl)hydrazono)methyl)benzene-1,3-diol (2,4-Difluorophenyl)hydrazine (300 mg, 2.1 mmol), 2,4-Dihydroxybenzaldehyde (287 mg, 2.1 mmol); Purification: Method 2; Yield: 526 mg, 96%; $C_{13}H_{10}F_2N_2O_2$, M=264.23 g/mol
$^1$H-NMR (300 MHz, $d_6$-DMSO) ppm: 6.31 (s, 1H), 6.33 (br d, 1H, J=7.5 Hz), 7.00 (br t, 1H, J=8.6 Hz), 7.16-7.26 (m, 2H), 7.32 (d, 1H, J=8.4 Hz), 8.27 (s, 1H), 9.67 (s, 1H), 9.92 (s, 1H), 10.94 (s, 1H); $^{13}$C-NMR (75 MHz, $d_6$-DMSO) ppm: 102.39, 103.84 (dd, J=22.3 Hz, J=27.2 Hz), 107.47, 111.31 (dd, $J_{C-F}$=3.3 Hz, $J_{C-F}$=21.8 Hz) 111.89, 113.25 (dd, $J_{C-F}$=4.7 Hz, $J_{C-F}$=9.0 Hz) 128.90, 130.36 (dd, $J_{C-F}$=2.9 Hz, $J_{C-F}$=10.1 Hz) 141.35, 148.36 (dd, $J_{C-F}$=12.0 Hz, $J_{C-F}$=242.7 Hz), 154.38 (dd, $J_{C-F}$=10.9 Hz, $J_{C-F}$=236.7 Hz), 157.48, 159.22; GC-MS 264 m/z [M]$^+$; Purity: 98.0% (336 nm, $t_r$=1.70 min, Method: c)

EXAMPLE 10

5-((2-(2,4-Difluorophenyl)hydrazono)methyl)benzene-1,2,4-triol (2,4-Difluorophenyl)hydrazine (365 mg, 2.5 mmol), 2,4,5-Trihydroxybenzaldehyde (390 mg, 2.5 mmol); Purification: Method 8; Yield: 693 mg, 97%; $C_{13}H_{10}F_2N_2O_3$, M=280.23 g/mol $^1$H-NMR (300 MHz, $d_6$-DMSO) ppm: 6.38 (s, 1H), 6.93 (s, 1H), 7.01 (br t, 1H, J=8.7 Hz), 7.15-7.26 (m, 3H), 8.24 (s, 1H) 8.44 (s, 1H), 9.27 (s, 1H), 9.76 (s, 1H), 9.82 (s, 1H); $^{13}$C-NMR (75 MHz, $d_6$-DMSO) ppm: 103.40, 103.80 (dd, $J_{C-F}$=22.3 Hz, $J_{C-F}$=26.9 Hz), 110.96, 111.27 (dd, $J_{C-F}$=3.3 Hz, $J_{C-F}$=21.7 Hz), 113.10, 113.18 (dd, $J_{C-F}$=4.6 Hz, $J_{C-F}$=8.8 Hz) 130.57 (dd, $J_{C-F}$=2.8 Hz, $J_{C-F}$=10.1 Hz) 138.39, 140.84, 147.58, 148.31 (dd, $J_{C-F}$=11.5 Hz, $J_{C-F}$=243.2 Hz), 149.86, 154.30 (dd, $J_{C-F}$=10.9 Hz, $J_{C-F}$=236.5 Hz); GC-MS 280 m/z [M]$^+$; Purity: 100.0% (348 nm, $t_r$=1.31 min, Method: c)

EXAMPLE 11

4-((2-(2,4-Difluorophenyl)hydrazono)methyl)benzene-1,2-diol (2,4-Difluorophenyl)hydrazine (300 mg, 2.1 mmol), 3,4-Dihydroxybenzaldehyde (287 mg, 2.1 mmol); Purification: Method 8; Yield: 326 mg, 59%; $C_{13}H_{10}F_2N_2O_2$, M=264.23 g/mol $^1$H-NMR (300 MHz, $d_6$-DMSO) ppm: 6.75 (d, 1H, J=8.1 Hz), 6.86 (dd, 1H, J=1.8 Hz, J=8.1 Hz), 6.99 (br t, 1H, J=8.7 Hz), 7.13-7.21 (m, 1H), 7.15 (d, 1H, J=1.9 Hz), 7.41 (td, 1H, J=1.9 Hz, J=9.3 Hz), 7.95 (s, 1H), 9.06 (s, 1H), 9.16 (s, 1H), 9.83 (s, 1H); $^{13}$C-NMR (75 MHz, $d_6$-DMSO) ppm: 103.61 (dd, $J_{C-F}$=22.3 Hz, $J_{C-F}$=26.9 Hz), 111.18 (dd, $J_{C-F}$=3.6 Hz, $J_{C-F}$=21.6 Hz), 112.05, 113.59 (dd, $J_{C-F}$=4.7 Hz, $J_{C-F}$=8.9 Hz), 115.50, 118.62, 126.93, 130.79 (dd, $J_{C-F}$=2.8 Hz, $J_{C-F}$=10.0 Hz), 140.38, 145.49, 146.40, 148.11 (dd, $J_{C-F}$=12.0 Hz, $J_{C-F}$=242.2 Hz), 154.19 (dd, $J_{C-F}$=10.9 Hz, $J_{C-F}$=236.2 Hz); GC-MS 264 m/z[M]$^+$; Purity: 98.2% (338 nm, $t_r$=1.44 min, Method: c)

EXAMPLE 12

4-((2-Phenylhydrazono)methyl)benzene-1,3-diol

Phenylhydrazine (200 mg, 1.8 mmol), 2,4-Dihydroxybenzaldehyde (255 mg, 1.8 mmol);
Purification: Method 3; Yield: 221 mg, 52%; $C_{13}H_{12}N_2O_2$, M=228.25 g/mol $^1$H-NMR (300 MHz, $d_6$-DMSO) ppm: 6.30 (s, 1H), 6.32 (dd, 1H, J=2.1, J=8.9 Hz), 6.73 (t, 1H, J=7.3 Hz), 6.89 (d, 2H, J=8.0 Hz), 7.17-7.30 (m, 3H), 8.04 (s, 1H), 9.65 (s, 1H), 10.10 (s, 1H), 10.73 (s, 1H); $^{13}$C-NMR (75 MHz, $d_6$-DMSO) ppm: 102.43, 107.39, 111.37, 111.88, 118.43, 129.09, 129.15, 139.22, 144.93, 157.46, 158.90; GC-MS 228 m/z [M]$^+$; Purity: 79.8% (340 nm, $t_r$=2.46 min, Method: b)

EXAMPLE 13

2-((2-Phenylhydrazono)methyl)phenol

Phenylhydrazine (250 mg, 2.3 mmol), 2-Hydroxybenzaldehyde (282 mg, 2.3 mmol);
Purification: Method 1; Yield: 203 mg, 41%; $C_{13}H_{12}N_2O$, M=212.25 g/mol $^1$H-NMR (300 MHz, $d_6$-DMSO) ppm: 6.79 (t, 1H, J=7.3 Hz), 6.89 (t, 2H, J=7.7 Hz), 6.98 (d, 2H, J=8.0 Hz), 7.18 (t, 1H, J=7.4 Hz), 7.26 (t, 2H, J=7.8 Hz), 7.55 (d, 1H, J=7.8 Hz), 8.16 (s, 1H) 10.40 (s, 1H), 10.54 (s, 1H); $^{13}$C-HMR (75 MHz, $d_6$-DMSO) ppm: 111.66, 115.83, 118.91, 119.30, 120.38, 127.29, 129.10, 129.20, 137.31, 144.67, 155.61; GC-MS 212 m/z [M]$^+$; Purity: 97.1% (342 nm, $t_r$=2.81 min, Method: c)

EXAMPLE 14

4-((2-(2,5-Dichlorophenyl)hydrazono)methyl)benzene-1,3-diol (2,5-Dichlorophenyl)hydrazine (500 mg, 2.8 mmol), 2,4-Dihydroxybenzaldehyde (390 mg, 2.8 mmol);
Purification: Method 10; Yield: 533 mg, 63%; $C_{13}H_{10}Cl_2N_2O_2$, M=297.14 g/mol $^1$H-NMR (300 MHz, $d_6$-DMSO) ppm: 6.32 (s, 1H), 6.34 (d, 1H, J=7.2 Hz), 6.78 (d, 1H, J=2.4, J=8.4), 7.27 (d, 1H, J=2.4 Hz), 7.34 (d, 1H, J=8.4 Hz), 7.44 (d, 1H, J=9.0 Hz), 8.49 (s, 1H) 9.72 (s, 1H), 9.87 (s, 1H), 10.22 (s, 1H); $^{13}$C-NMR (75 MHz, $d_6$-DMSO) ppm: 102.38, 107.70, 112.02, 112.11, 114.47, 118.15, 128.42, 130.66, 132.66, 142.29, 142.45, 157.57, 159.69; GC-MS 296 m/z [M–H]$^+$; Purity: 66.0% (338 nm, $t_r$=3.70 min, Method: d)

EXAMPLE 15

4-((2-(2-Chloro-5-(trifluoromethyl)phenyl)hydrazono)methyl)benzene-1,3-diol (2-Chloro-5-(trifluoromethyl)phenyl)hydrazine (250 mg, 1.2 mmol), 2,4-Dihydroxybenzaldehyde (163 mg, 1.2 mmol);
Purification: Method 10; Yield: 360 mg, 92%; $C_{14}H_{10}ClF_3N_2O_2$, M=330.69 g/mol $^1$H-NMR (300 MHz, $d_6$-DMSO) ppm: 6.34 (s, 1H), 6.35 (d, 1H, J=7.4 Hz), 7.06 (d, 1H, J=8.4), 7.45 (d, 1H, J=8.7 Hz), 7.53 (s, 1H), 7.56 (d, 1H, J=9.0 Hz), 8.54 (s, 1H) 9.74 (s, 1H), 10.04 (s, 1H), 10.21 (s, 1H); $^{13}$C-NMR (75 MHz, $d_6$-DMSO) ppm: 102.49, 107.83, 108.80 (q, $J_{C-F}$=4.0 Hz), 112.07, 114.79 (q, $J_{C-F}$=3.61 Hz), 119.64, 124.03 (d, $J_{C-F}$=272.4 Hz), 128.42, 128.87 (q, $J_{C-F}$=31.8 Hz), 130.41, 142.09, 142.65, 157.71, 159.87; GC-MS 330 m/z [M]$^+$; Purity: 97.5% (338 nm, $t_r$=3.31 min, Method: c)

EXAMPLE 16

4-((2-(2-Chlorophenyl)hydrazono)methyl)benzene-1,3-diol (2-Chlorophenyl)hydrazine hydrochloride (500 mg, 2.8 mmol), 2,4-Dihydroxybenzaldehyde (386 mg, 2.8 mmol);
Purification: Method 10; Yield: 638 mg, 69%; $C_{13}H_{11}ClN_2O_2$, M=262.69 g/mol $^1$H-NMR (300 MHz, $d_6$-DMSO) ppm: 6.30-6.38 (m, 2H), 6.73-6.82 (m, 1H), 7.22-7.29 (m, 2H), 7.29-7.36 (m, 2H), 8.44 (s, 1H), 9.68 (d, 1H), 10.51 (br s, 2H); $^{13}$C-NMR (75 MHz, $d_6$-DMSO) ppm: 102.46, 107.60, 111.77, 116.10, 119.17, 128.04, 129.02, 129.34, 141.17, 142.43, 157, 71, 159.54; GC-MS 262 m/z [M]$^+$; Purity: 100.0% (338 nm, $t_r$=2.71 min, Method: d)

EXAMPLE 17

4-((2-(2,4-Dichlorophenyl)hydrazono)methyl)benzene-1,3-diol (2,4-Dichlorophenyl)hydrazine (200 mg, 1.1 mmol), 2,4-Dihydroxybenzaldehyde (129 mg, 0.9 mmol);
Purification: Method 3; Yield: 86 mg, 26%; $C_{13}H_{10}C_2N_2O_2$, M=297.14 g/mol ¹H-NMR (300 MHz, d₆-DMSO) ppm: 6.32-6.34 (m, 2H), 7.30 (s, 2H), 7.38 (d, 2H, J=9.1), 7.44 (s, 1H), 8.46 (s, 1H), 9.79 (s, 1H) 10.31 (br s, 2H); ¹³C-NMR (75 MHz, d₆-DMSO) ppm: 102.41, 107.61, 111.91, 113.99, 116.43, 121.50, 127.99, 128.51, 128.58, 140.49, 142.22, 157.59, 159.60; GC-MS 296 m/z [M–H]⁺; Purity: 98.2% (336 nm, $t_r$=1.70 min, Method: c)

EXAMPLE 18

4-((2-(2-Chloro-4-(trifluoromethyl)phenyl)hydrazono)methyl)benzene-1,3-diol (2-Chloro-4-(trifluoromethyl)phenyl)hydrazine (250 mg, 1.2 mmol), 2,4-Dihydroxybenzaldehyde (163 mg, 1.2 mmol);
Purification: Method 3; Yield: 314 mg, 80%; $C_{14}H_{10}ClF_3N_2O_2$, M=330.69 g/mol
¹H-NMR (300 MHz, d₆-DMSO) ppm: 6.34-6.37 (m, 2H), 7.47 (d, 2H, J=9.0), 7.59 (dd, 1H, J=1.8 Hz, J=8.1 Hz), 7.69 (d, 1H, J=1.8 Hz), 8.58 (s, 1H) 9.77 (s, 1H), 10.14 (s, 1H), 10.23 (s, 1H); ¹³C-NMR (75 MHz, d₆-DMSO) ppm: 102.44, 107.77, 111.95, 112.61, 115.53, 118.51 (q, $J_{C-F}$=32.8 Hz), 124.15 (d, $J_{C-F}$=270.8 Hz), 125.28 (q, $J_{C-F}$=3.6 Hz), 126.42 (q, $J_{C-F}$=3.8 Hz), 128.57, 143.21, 144.28, 157.78, 159.93; GC-MS 330 m/z [M]⁺; Purity: 98.4% (342 nm, $t_r$=3.57 min, Method: c)

EXAMPLE 19

4-((2-(4-Iodophenyl)hydrazono)methyl)benzene-1,3-diol (4-Iodophenyl)hydrazine (200 mg, 0.9 mmol), 2,4-Dihydroxybenzaldehyde (118 mg, 0.9 mmol);
Purification: Method 3; Yield: 264 mg, 87%; $C_{13}H_{11}IN_2O_2$, M=354.14 g/mol
¹H-NMR (300 MHz, d₆-DMSO) ppm: 6.31 (s, 1H), 6.33 (d, 1H, J=7.4 Hz), 6.77 (d, 2H, J=8.6 Hz), 7.34 (d, 1H, J=8.7 Hz), 7.51 (d, 2H, J=8.6 Hz), 8.06 (s, 1H), 9.68 (s, 1H), 10.24 (s, 1H), 10.49 (s, 1H); ¹³C-NMR (75 MHz, d₆-DMSO) ppm: 79.29, 102.34, 107.44, 111.91, 113.86, 128.69, 137.41, 139.19, 144.74, 157.31, 159.06; GC-MS 354 m/z [M]⁺; Purity: 96.7% (346 nm, $t_r$=2.39 min, Method: c)

EXAMPLE 20

5-((2-(4-Iodophenyl)hydrazono)methyl)benzene-1,2,4-triol (4-Iodophenyl)hydrazine (300 mg, 1.3 mmol), 2,4,5-Trihydroxybenzaldehyde (198 mg, 1.3 mmol);
Purification: Method 3; Yield: 430 mg, 91%; $C_{13}H_{11}IN_2O_3$, M=370.14 g/mol
¹H-NMR (300 MHz, d₆-DMSO) ppm: 6.31 (s, 1H), 6.75 (d, 2H, J=8.7 Hz), 6.92 (s, 1H), 7.49 (d, 2H, J=8.7 Hz), 7.99 (s, 1H), 8.40 (s, 1H), 9.22 (s, 1H), 9.69 (s, 1H), 10.15 (s, 1H); ¹³C-NMR (75 MHz, d₆-DMSO) ppm: 79.02, 103.34, 110.99, 112.86, 113.83, 137.36, 138.34, 138.59, 144.90, 147.38, 149.65; GC-MS 370 m/z [M]⁺; Purity: 96.1% (352 nm, $t_r$=1.72 min, Method: c)

EXAMPLE 21

5-((2,2-Diphenylhydrazono)methyl)benzene-1,2,4-triol 1,1-Diphenylhydrazine (520 mg, 2.8 mmol), 2,4,5-Trihydroxybenzaldehyde (539 mg, 2.8 mmol);
Purification: Method 5; Yield: 491 mg, 53%; $C_{19}H_{16}N_2O_3$, M=320.34 g/mol
¹H-NMR (300 MHz, d₆-DMSO) ppm: 6.28 (s, 1H), 7.01 (s, 1H) 7.09 (d, 4H, J=7.8 Hz), 7.19 (t, 2H, J=7.3 Hz), 7.34 (s, 1H), 7.45 (t, 4H, J=7.8 Hz), 8.40 (s, 1H), 9.18 (s, 1H), 9.46 (s, 1H); ¹³C-NMR (75 MHz, d₆-DMSO) ppm: 103.31, 111.40, 112.42, 121.85, 124.09, 129.88, 135.91, 143.35, 147.46, 149.45; GC-MS 320 m/z [M]⁺; Purity: 96.2% (354 nm, $t_r$=2.48 min, Method: i)

EXAMPLE 22

4-((2,2-Diphenylhydrazono)methyl)benzene-1,3-diol 1,1-Diphenylhydrazine (337 mg, 1.8 mmol), 2,4-Dihydroxybenzaldehyde (230 mg, 1.7 mmol);
Purification: Method 9; Yield: 501 mg, 90%; $C_{19}H_{16}N_2O_2$, M=304.34 g/mol
¹H-NMR (300 MHz, d₆-DMSO) ppm: 6.28-6.30 (m, 2H), 7.10 (d, 4H, J=7.8 Hz), 7.20 (t, 2H, J=7.3 Hz), 7.35 (d, 1H, J=9.1 Hz), 7.39 (s, 1H) 7.45 (t, 4H, J=7.8 Hz), 9.64 (s, 1H), 10.39 (s, 1H); ¹³C-NMR (75 MHz, d₆-DMSO) ppm: 102.35, 107.52, 112.16, 121.92, 124.30, 128.77, 129.96, 137.16, 143.15, 157.27, 159.21; GC-MS 304 m/z [M]⁺; Purity: 97.6% (344 nm, $t_r$=3.85 min, Method: c)

EXAMPLE 23

4-((2-(Perfluorophenyl)hydrazono)methyl)benzene-1,3-diol (Perfluorophenyl)hydrazine (200 mg, 1. mmol), 2,4-Dihydroxybenzaldehyde (139 mg, 1.0 mmol);
Purification: Method 11; Yield: 254 mg, 79%; $C_{13}H_7F_5N_2O_2$, M=318.20 g/mol
¹H-NMR (300 MHz, d₆-DMSO) ppm: 6.30 (d, 1H, J=1.8 Hz), 6.34 (dd, 1H, J=2.0 Hz, J=8.4 Hz), 7.23 (d, 1H, J=8.4 Hz), 8.27 (s, 1H), 9.81 (s, 1H), 10.18 (s, 1H), 10.56 (s, 1H); ¹³C-NMR (75 MHz, d₆-DMSO) ppm: 102.41, 107.45, 110.81, 121.12 (t, $J_{C-F}$=10.9 Hz), 131.44 (d,), 134.41-139.83 (m, $J_{C-F}$=13.4 Hz), 144.72, 158.09, 159.67; GC-MS 318 m/z[M]⁺; Purity: 99.8% (322 nm, $t_r$=2.22 min, Method: c)

EXAMPLE 24

4-((2-(Perfluorophenyl)hydrazono)methyl)benzene-1,2-diol (Perfluorophenyl)hydrazine (300 mg, 1.5 mmol), 3,4-Dihydroxybenzaldehyde (209 mg, 1.5 mmol);
Purification: Method 3; Yield: 447 mg, 93%; $C_{13}H_7F_5N_2O_2$, M=318.20 g/mol
¹H-NMR (300 MHz, d₆-DMSO) ppm: 6.74 (d, 1H, J=8.1 Hz), 6.82 (dd, 1H, J=1.8 Hz, J=8.1 Hz), 7.10 (d, 1H, J=1.7 Hz), 7.96 (s, 1H), 9.11 (s, 1H), 9.20 (s, 1H), 9.95 (s, 1H); ¹³C-NMR (75 MHz, d₆-DMSO) ppm: 112.03, 115.47, 119.15, 121.78 (t, $J_{C-F}$=11.7 Hz), 126.23, 131.48-131.84 (m), 134.70-136.32 (m), 138.54-139.55 (m), 143.14, 145.55, 146.92; GC-MS 318 m/z [M]⁺;
Purity: 96.0% (318 nm, $t_r$=1.72 min, Method: c)

EXAMPLE 25

4-((2-Methyl-2-phenylhydrazono)methyl)benzene-1,2-diol

1-Methyl-1-phenylhydrazine (289 μL, 2.5 mmol), 3,4-Dihydroxybenzaldehyde (339 mg, 2.5 mmol);
Purification: Method 3; Yield: 226 mg, 38%; $C_{14}H_{14}N_2O_2$, M=242.27 g/mol ¹H-NMR (300 MHz, d₆-DMSO) ppm: 3.35 (s, 3H), 6.74 (d, 1H, J=8.1 Hz), 6.83 (t, 1H, J=7.0 Hz), 6.92 (dd, 1H, J=1.8 Hz, J=8.1 Hz), 7.21 (d, 1H, J=1.8 Hz), 7.27 (t, 2H, J=7.9 Hz), 7.35 (d, 2H, J=8.1 Hz), 7.54 (s, 1H), 9.02 (br s, 2H); ¹³C-NMR (75 MHz, d₆-DMSO) ppm: 32.49, 112.01, 114.12, 115.47, 118.59, 119.26, 128.20, 128.80, 133.31, 145.43, 145.76, 147.65; GC-MS 242 m/z [M]⁺; Purity: 97.3% (340 nm, $t_r$=1.54 min, Method: c)

EXAMPLE 26

4-((2-Methyl-2-phenylhydrazono)methyl)benzene-1,3-diol

1-Methyl-1-phenylhydrazine (289 μL, 2.5 mmol), 2,4-Dihydroxybenzaldehyde (339 mg, 2.5 mmol);
Purification: Method 3; Yield: 382 mg, 64%; $C_{14}H_{14}N_2O_2$, M=242.27 g/mol
¹H-NMR (300 MHz, d₆-DMSO) ppm: 3.38 (s, 3H), 6.30 (d, 1H, J=2.2 Hz), 6.34 (dd, 1H, J=8.3.0 Hz, J=2.3 Hz), 6.89 (t, 1H, J=7.2 Hz), 7.21 (d, 2H, J=8.0 Hz), 7.27-7.37 (m, 3H), 7.88 (s, 1H), 9.62 (s, 1H), 10.98 (s, 1H); ¹³C-NMR (75 MHz, d₆-DMSO) ppm: 32.94, 102.44, 107.34, 112.47, 114.31, 120.03, 129.12, 129.58, 135.96, 147.20, 157.30, 158.73; GC-MS 242 m/z [M]⁺; Purity: 98.8% (336 nm, $t_r$=1.85 min, Method: c)

EXAMPLE 27

5-((2-Methyl-2-phenylhydrazono)methyl)benzene-1,2,4-triol

1-Methyl-1-phenylhydrazine (289 μL, 2.5 mmol), 2,4,5-Trihydroxybenzaldehyde (378 mg, 2.5 mmol);
Purification: Method 3; Yield: 295 mg, 47%; $C_{14}H_{14}N_2O_3$, M=258.27 g/mol
¹H-NMR (300 MHz, d₆-DMSO) ppm: 3.36 (s, 3H), 6.31 (s, 1H), 6.87 (t, 1H, J=7.1 Hz), 6.96 (s, 1H), 7.22 (d, 2H, J=7.9 Hz), 7.30 (t, 2H, J=7.9 Hz), 7.79 (s, 1H), 8.40 (s, 1H), 9.16 (s, 1H), 10.15 (s, 1H); ¹³C-NMR (75 MHz, d₆-DMSO) ppm: 32.83, 103.33, 111.57, 113.83, 114.14, 119.72, 129.02, 134.93, 138.20, 146.92, 147.31, 149.51; GC-MS 258 m/z [M]⁺; Purity: 98.4% (348 nm, $t_r$=1.34 min, Method: c)

EXAMPLE 28

3-Chloro-4-(2-(2,4,5-trihydroxybenzylidene)hydrazinyl)benzonitrile

3-Chloro-4-hydrazinylbenzonitrile (250 mg, 1.5 mmol), 2,4,5-Trihydroxybenzaldehyde (230 mg, 1.5 mmol);
Purification: Method 1; Yield: 301 mg, 66%; $C_{14}H_{10}ClN_3O_3$, M=303.70 g/mol
¹H-NMR (300 MHz, d₆-DMSO) ppm: 6.34 (s, 1H), 7.07 (s, 1H), 7.42 (d, 1H, J=8.7 Hz), 7.66 (dd, 1H, J=1.5 Hz, J=8.7 Hz), 7.83 (d, 1H, J=1.6 Hz), 8.49 (s, 1H), 8.56 (s, 1H), 9.36 (s, 1H), 9.45 (s, 1H), 10.25 (s, 1H); ¹³C-NMR (75 MHz, d₆-DMSO) ppm: 99.13, 103.40, 110.88, 112.18, 112.61, 115.35, 118.85, 132.36, 132.93, 138.65, 143.25, 144.87, 148.61, 150.40; GC-MS 303 m/z [M]⁺; Purity: 100.0% (362 nm, $t_r$=1.23 min, Method: c)

EXAMPLE 29

3-Chloro-4-(2-(2,4-dihydroxybenzylidene)hydrazinyl)benzonitrile

3-Chloro-4-hydrazinylbenzonitrile (250 mg, 1.5 mmol), 2,4-Dihydroxybenzaldehyde (206 mg, 1.5 mmol);
Purification: Method 1; Yield: 258 mg, 60%; $C_{14}H_{10}ClN_3O_2$, M=287.70 g/mol
¹H-NMR (300 MHz, d₆-DMSO) ppm: 6.32-6.35 (m, 2H), 7.43 (d, 1H, J=8.7 Hz), 7.50 (d, 1H, J=9.1 Hz), 7.64 (dd, 1H, J=1.4 Hz, J=8.7 Hz), 7.84 (d, 1H, J=1.5 Hz), 8.60 (s, 1H), 9.78 (s, 1H), 10.15 (s, 1H), 10.29 (s, 1H); ¹³C-NMR (75 MHz, d₆-DMSO) ppm: 99.37, 102.42, 107.83, 111.89, 112.70, 115.46, 118.81, 128.45, 132.37, 132.94, 143.72, 144.75, 157.86, 160.11; GC-MS 287 m/z [M]⁺; Purity: 98.7% (354 nm, $t_r$=1.58 min, Method: c)

EXAMPLE 30

3-Chloro-4-(2-(3,4-dihydroxybenzylidene)hydrazinyl)benzonitrile

3-Chloro-4-hydrazinylbenzonitrile (250 mg, 1.5 mmol), 3,4-Dihydroxybenzaldehyde (206 mg, 1.5 mmol);
Purification: Method 1; Yield: 200 mg, 47%; $C_{14}H_{10}ClN_3O_2$, M=287.70 g/mol
¹H-NMR (300 MHz, d₆-DMSO) ppm: 6.78 (d, 1H J=8.1 Hz), 6.93 (dd, 1H, J=1.8 Hz, J=8.1 Hz), 7.20 (d, 1H, J=1.7 Hz), 7.55 (d, 1H, J=8.7 Hz), 7.67 (dd, 1H, J=1.7 Hz, J=8.7 Hz), 7.85 (d, 1H, J=1.7 Hz), 8.26 (s, 1H), 9.15 (s, 1H), 9.33 (s, 1H), 10.24 (s, 1H); ¹³C-NMR (75 MHz, d₆-DMSO) ppm: 99.12, 103.39, 110.87, 112.15, 112.60, 115.34, 118.84, 132.36, 132.93, 138.65, 143.23, 144.87, 148.61, 150.39; GC-MS 287 m/z [M]⁺; Purity: 99.1% (354 nm, $t_r$=1.37 min, Method: c)

EXAMPLE 31

4-((2-(4-Nitrophenyl)hydrazono)methyl)benzene-1,2-diol (4-Nitrophenyl)hydrazine+H₂O (500 mg, 70%, 2.3 mmol), 4,5-Dihydroxybenzaldehyde (316 mg, 2.3 mmol);
Purification: Method 7; Yield: 381 mg, 61%; $C_{13}H_{11}N_3O_4$, M=273.24 g/mol
¹H-NMR (300 MHz, d₆-DMSO) ppm: 6.77 (d, 1H, J=8.1 Hz), 6.95 (dd, 1H, J=1.8 Hz, J=8.1 Hz), 7.09 (d, 2H, J=8.8 Hz), 7.21 (d, 1H, J=1.8 Hz), 7.89 (s, 1H), 8.12 (d, 2H, J=9.2 Hz), 9.24 (br s, 2H), 11.07 (s, 1H); ¹³C-NMR (75 MHz, d₆-DMSO) ppm: 110.69, 112.37, 115.52, 119.61, 126.02, 126.14, 137.65, 142.76, 145.58, 150.68; GC-MS 273 m/z [M]⁺; Purity: 98.8% (426 nm, $t_r$=1.19 min, Method: c)

EXAMPLE 32

5-((2-(4-Nitrophenyl)hydrazono)methyl)benzene-1,2,4-triol (4-Nitrophenyl)hydrazine+H₂O (500 mg, 70%, 2.3 mmol), 2,4,5-Trihydroxybenzaldehyde (352 mg, 2.3 mmol);
Purification: Method 1; Yield: 497 mg, 75%; $C_{13}H_{11}N_3O_5$, M=289.24 g/mol
¹H-NMR (300 MHz, d₆-DMSO) ppm: 6.35 (s, 1H), 7.01 (d, 2H, J=9.2 Hz), 7.09 (s, 1H), 8.12 (d, 2H, J=9.2 Hz), 8.21 (s, 1H), 8.51 (s, 1H), 9.38 (s, 1H), 9.47 (s, 1H), 11.06 (s, 1H); ¹³C-NMR (75 MHz, d₆-DMSO) ppm: 103.38, 110.41, 110.80, 111.96, 126.25, 137.44, 138.69, 141.18, 148.60, 150.25, 150.42; GC-MS 289 m/z [M]⁺; Purity: 76.5% (428 nm, $t_r$=1.13 min, Method: c)

EXAMPLE 33

4-((2-(4-Nitrophenyl)hydrazono)methyl)benzene-1,3-diol (4-Nitrophenyl)hydrazine+H₂O (500 mg, 70%, 2.3 mmol), 4,5-Dihydroxybenzaldehyde (316 mg, 2.3 mmol);
Purification: Method 1; Yield: 598 mg, 96%; $C_{13}H_{11}N_3O_4$, M=273.24 g/mol ¹H-NMR (300 MHz, d₆-DMSO) ppm: 6.33-6.36 (m, 2H), 7.03 (d, 2H, J=9.1 Hz), 7.51 (d, 1H, J=9.1 Hz), 8.12 (d, 2H, J=9.2 Hz), 8.25 (s, 1H), 9.79 (s, 1H), 10.18 (s, 1H), 11.11 (s, 1H); ¹³C-NMR (75 MHz, d₆-DMSO) ppm: 102.38, 107.84, 110.52, 111.80, 126.22, 128.23, 137.63, 141.58, 150.31, 157.68, 160.04; GC-MS 273 m/z [M]⁺; Purity: 98.1% (420 nm, $t_r$=1.34 min, Method: c)

EXAMPLE 34

4-((Piperidin-1-ylimino)methyl)benzene-1,3-diol

Piperidin-1-amine (300 mg, 3.0 mmol), 2,4-Dihydroxybenzaldehyde (414 mg, 3.0 mmol);
Purification: Method 1; Yield: 462 mg, 70%; $C_{12}H_{16}N_2O_2$, M=220.27 g/mol
¹H-NMR (300 MHz, d₆-DMSO) ppm: 1.39-1.52 (m, 2H), 1.59-1.72 (m, 4H), 2.96-3.03 (m, 4H), 6.21 (d, 1H, J=2.2 Hz), 6.28 (dd, 1H, J=2.3 Hz, J=8.3 Hz), 7.11 (d, 1H, J=8.4 Hz), 7.83 (s, 1H), 9.62 (s, 1H), 11.80 (s, 1H); ¹³C-NMR (75 MHz, d₆-DMSO) ppm: 23.35, 24.34, 51.91, 102.30, 106.78, 111.68, 130.52, 140.57, 158.48, 158.60; GC-MS 220 m/z [M]⁺; Purity: 97.% (290 nm), 99.2%, (308 nm, $t_r$=1.56 min, Method: c)

EXAMPLE 35

4-((2-(Benzo[d]thiazol-2-yl)hydrazono)methyl)benzene-1,3-diol

2-Hydrazinylbenzo[d]thiazole (300 mg, 1.8 mmol), 2,4-Dihydroxybenzaldehyde (251 mg, 1.8 mmol);
Purification: Method 1; Yield: 290 mg, 56%; $C_{14}H_{11}N_3O_2S$, M=285.32 g/mol
¹H-NMR (300 MHz, d₆-DMSO) ppm: 6.34 (s, 1H), 6.36 (dd, 1H, J=2.1 Hz, J=9.8 Hz), 7.07 (t, 1H, J=8.1 Hz), 7.23-7.31 (m, 2H), 7.39 (d, 1H, J=8.2 Hz), 7.71 (d, 1H, J=7.7 Hz), 8.34 (s, 1H), 9.89 (s, 1H), 10.59 (s, 1H), 11.95 (s, 1H); ¹³C-NMR (75 MHz, d₆-DMSO) ppm: 102.34, 107.74, 111.19, 121.18, 121.75, 126.10, 160.22; GC-MS 285 m/z [M]⁺; Purity: 100.0% (332 nm, $t_r$=1.30 min, Method: c)

EXAMPLE 36

3-(2-(2,4-Dihydroxybenzylidene)hydrazinyl)propanenitrile

3-Hydrazinylpropanenitrile (300 mg, 3.5 mmol), 2,4-Dihydroxybenzaldehyde (251 mg, 3.5 mmol);
Purification: Method 1; Yield: 75 mg, 10%; $C_{10}H_{11}N_3O_2$, M=205.21 g/mol
¹H-NMR (300 MHz, d₆-DMSO) ppm: 2.69 (t, 2H, J=6.4 Hz), 3.28-3.33 (m, 2H), 6.23 (d, 1H, J=2.1 Hz), 6.27 (dd, 1H, J=2.2 Hz, J=8.3 Hz), 7.08 (d, 1H, J=8.3 Hz), 7.86 (d, 1H, J=8.3 Hz), 10.11 (br s, 1H) 11.02 (br s, 1H); ¹³C-NMR (75 MHz, d₆-DMSO) ppm: 17.04, 44.61, 102.29, 106.91, 111.50, 119.52, 129.59, 141.67, 157.93, 158.64; GC-MS 205 m/z [M]⁺; Purity: 93.4% (290 nm), 91.5% (306 nm, $t_r$=3.47 min; Methode: i)

EXAMPLE 37

2-((2-(4-(Trifluoromethyl)phenyl)hydrazono)methyl)benzene-1,3,5-triol (2,6-Dichloro-4-(Trifluoromethyl)phenyl)hydrazine (500 mg, 2.8 mmol), 2,4,6-Trihydroxybenzaldehyde (437 mg, 2.8 mmol);
Purification: Method 10; Yield: 640 mg, 72%; $C_{14}H_{11}F_3N_2O_3$, M=312.24 g/mol
¹H-NMR (300 MHz, d₆-DMSO) ppm: 5.86 (s, 2H), 6.92 (d, 2H, J=8.5 Hz), 7.55 (d, 2H, J=8.6 Hz), 8.41 (s, 1H), 9.68 (s, 1H), 10.59 (s, 1H), 10.62 (s, 2H); ¹³C-NMR (75 MHz, d₆-DMSO) ppm: 94.29, 99.29, 110.66, 117.95 (q, $J_{C-F}$=31.92 Hz), 124.87 (d, $J_{C-F}$=264.9 Hz), 126.65 (q, $J_{C-F}$=3.8 Hz), 140.34, 147.39, 158.34, 160.28; GC-MS 312 m/z[M–H]⁺; Purity: 100.0% (350 nm, $t_r$=1.89 min, Method: c)

EXAMPLE 38

2-((2-(2,6-Dichloro-4-(trifluoromethyl)phenyl)hydrazono) methyl)benzene-1,3,5-triol (2,6-Dichloro-4-(trifluoromethyl)phenyl)hydrazine (500 mg, 2.0 mmol), 2,4,6-Trihydroxybenzaldehyde (314 mg, 2.0 mmol);
Purification: Method 10; Yield: 700 mg, 90%; $C_{14}H_9Cl_2F_3N_2O_3$, M=381.13 g/mol
¹H-NMR (300 MHz, d₆-DMSO) ppm: 5.82 (s, 2H), 7.81 (s, 2H), 8.72 (s, 1H), 9.68 (s, 1H), 9.73 (s, 1H), 10.48 (s, 2H); ¹³C-NMR (75 MHz, d₆-DMSO) ppm: 94.23, 99.07, 121.87 (q, $J_{C-F}$=33.8 Hz), 122.88, 122.96 (d, $J_{C-F}$=271.9 Hz), 126.60 (q, $J_{C-F}$=3.7 Hz), 140.96, 143.54, 158.81, 160.57; ppm: GC-MS 380 m/z[M–H]⁺; Purity: 99.2% (342 nm, $t_r$=3.11 min, Method: c)

EXAMPLE 39

2-((2-(Benzo[d]thiazol-2-yl)hydrazono)methyl)benzene-1,3,5-triol

2-Hydrazinylbenzo[d]thiazole (500 mg, 3.0 mmol), 2,4,6-Trihydroxybenzaldehyde (466 mg, 3.0 mmol);
Purification: Method 3; Yield: 435 mg, 48%; $C_{14}H_{11}N_3O_3S$, M=301.32 g/mol
¹H-NMR (300 MHz, d₆-DMSO) ppm: 5.87 (s, 2H), 7.06 (t, 1H, J=7.9 Hz), 7.27 (pt, 2H, J=6.9 Hz), 7.68 (d, 1H, J=5.9 Hz), 8.56 (s, 1H), 9.80 (s, 1H), 10.65 (bs, 2H), 11.87 (bs, 1H); ¹³C-NMR (75 MHz, d₆-DMSO) ppm: 94.32, 99.23, 121.20, 121.99, 126.32, 159.22, 161.18, 164.06; GC-MS 301 m/z [M]⁺; Purity: 100.0% (354 nm, $t_r$=1.21 min, Method: c)

EXAMPLE 40

4-((2-(4-(Trifluoromethyl)phenyl)hydrazono)methyl)phenol (4-(Trifluoromethyl)phenyl)hydrazine (500 mg, 2.8 mmol), 4-Hydroxybenzaldehyde (347 mg, 2.8 mmol)
Purification: Method 10; Yield: 483 mg, 61%; $C_{14}H_{11}F_3N_2O$, M=280.25 g/mol ¹H-NMR (300 MHz, d₆-DMSO) ppm: 6.81 (d, 2H, J=8.5 Hz), 7.14 (d, 2H, J=8.4 Hz), 7.51 (d, 2H, J=8.9 Hz), 7.52 (d, 2H, J=8.6 Hz), 7.87 (s, 1H), 9.71 (s, 1H), 10.53 (s, 1H); ¹³C-NMR (75 MHz, d₆-DMSO) ppm: 111.22, 115.51, 117.66 (q, $J_{C-F}$=31.8 Hz), 125.02 (d, $J_{C-F}$=270.2 Hz), 126.18, 126.31 (q, $J_{C-F}$=3.7 Hz), 127.55, 139.49, 148.47, 158.13; GC-MS 280 m/z[M]; Purity: 100.0% (344 nm, $t_r$=2.68 min, Method: c)

EXAMPLE 41

4-((2-(2,6-Dichloro-4-(trifluoromethyl)phenyl)hydrazono)methyl)phenol (2,6-Dichloro-4-(trifluoromethyl)phenyl)hydrazine (500 mg, 2.0 mmol), 4-Hydroxybenzaldehyde (249 mg, 2.0 mmol)
Purification: Method 10; Yield: 520 mg, 73%; $C_{14}H_9Cl_2F_3N_2O$, M=349.14 g/mol ¹H-NMR (300 MHz, d₆-DMSO) ppm: 6.81 (d, 2H, J=8.5 Hz), 7.47 (d, 2H, J=8.5 Hz), 7.77 (s, 2H), 8.17 (s, 1H), 9.72 (s, 1H), 9.75 (s, 1H); ¹³C-NMR (75 MHz, d₆-DMSO) ppm: 115.22, 121.44 (q, $J_{C-F}$=33.6 Hz), 122.97, 125.92, 126.52 (q, $J_{C-F}$=3.6 Hz), 126.63 (d, $J_{C-F}$=271.6 Hz), 127.69, 141.42, 142.67, 158.47; GC-MS 348 m/z [M–H]⁺; Purity: 100.0% (334 nm, $t_r$=4.66 min, Method: c)

EXAMPLE 42

4-((2-(Benzo[d]thiazol-2-yl)hydrazono)methyl)phenol

2-Hydrazinylbenzo[d]thiazole (500 mg, 3.0 mmol), 4-Hydroxybenzaldehyde (369 mg, 3.0 mmol) Purification: Method 1; Yield: 620 mg, 76%; C₁₄H₁₁N₃OS, M=269.32 g/mol ¹H-NMR (300 MHz, d₆-DMSO) ppm: 6.83 (d, 2H, J=8.5), 7.08 (t, 1H, J=7.6 Hz), 7.28 (t, 1H, J=7.5 Hz), 7.41 (bs, 1H), 7.53 (d, 2H, J=8.5 Hz), 7.53 (d, 2H, J=8.5 Hz), 7.53 (d, 2H, J=8.5 Hz), 7.74 (d, 1H, J=7.6 Hz), 8.03 (s, 1H), 9.86 (s, 1H), 12.02 (bs, 1H); ¹³C-NMR (75 MHz, d₆-DMSO) ppm: 115.62, 121.20, 121.32, 125.26, 125.75, 128.14, 158.92, 166.69; GC-MS 269 m/z [M]⁺; Purity: 100.0% (338 nm, $t_r$=1.44 min, Method: c)

EXAMPLE 43

4-((2-Methyl-2-(2-nitro-4-(trifluoromethyl)phenyl)hydrazono)methyl)benzene-1,3-diol 1-Methyl-1-(2-nitro-4-(trifluoromethyl)phenyl)hydrazine (400 mg, 1.7 mmol), 2,4-Dihydroxybenzaldehyde (117 mg, 1.7 mmol)

Purification: Method 10; Yield: 479 mg, 79%; C₁₅H₁₂F₃N₃O₄, M=355.27 g/mol

¹H-NMR (300 MHz, d₆-DMSO) ppm: 6.26 (dd, 1H, J=2.2 Hz, J=8.5 Hz), 7.28 (d, 1H, J=8.53 Hz), 7.56 (d, 1H, J=8.9 Hz), 7.85 (dd, 1H, J=1.9 Hz, J=8.9 Hz), 7.91 (s, 1H), 8.06 (d, 1H, J=1.5 Hz), 9.66 (bs, 1H), 9.79 (bs, 1H);

¹³C-NMR (75 MHz, d₆-DMSO) ppm: 33.81, 102.24, 107.64, 112.55, 119.11, 119.56 (q, $J_{C-F}$=33.6 Hz), 122.80 (q, $J_{C-F}$=3.9 Hz); 123.49 (d, $J_{C-F}$=271.23 Hz), 127.06, 128.78 (q, $J_{C-F}$=3.5 Hz), 135.77, 139.63, 143.21, 157.19, 159.70; GC-MS 355 m/z[M]⁺; Purity: 100.0% (338 nm, $t_r$=2.33 min, Method: c)

EXAMPLE 44

4-((2-Methyl-2-(2-nitro-4-(trifluoromethyl)phenyl)hydrazono)methyl)benzene-1,2,3-triol 1-Methyl-1-(2-nitro-4-(trifluoromethyl)phenyl)hydrazine (500 mg, 2.1 mmol), 2,3,4-Trihydroxybenzaldehyde (327 mg, 2.1 mmol)

Purification: Method 1; Yield: 368 mg, 47%; C₁₅H₁₂F₃N₃O₅, M=371.27 g/mol

¹H-NMR (300 MHz, d₆-DMSO) ppm: 3.47 (s, 3H), 6.33 (d, 1H, J=8.6 Hz), 7.58 (d, 1H, J=8.6 Hz), 7.58 (d, 1H, J=8.9 Hz), 7.87 (dd, 1H, J=1.8 Hz, J=8.9 Hz), 7.93 (s, 1H), 8.08 (d, 1H, J=1.3 Hz), 8.41 (s, 1H), 9.06 (s, 1H), 9.40 (s, 1H); ¹³C-NMR (75 MHz, d₆-DMSO) ppm: 34.04, 107.64, 113.29, 116.76, 119.38, 119.72 (d, $J_{C-F}$=33.6 Hz), 122.85 (q, $J_{C-F}$=3.8 Hz), 123.46 (d, $J_{C-F}$=271.1 Hz), 128.86 (q, $J_{C-F}$=3.4 Hz), 132.64, 137.10, 139.65, 143.28, 145.86, 147.47; GC-MS 371 m/z[M]⁺; Purity: 96.9% (334 nm), 92.2 (404 nm, $t_r$=1.61 min, Method: m)

EXAMPLE 45

2-((2-Methyl-2-(2-nitro-4-(trifluoromethyl)phenyl)hydrazono)methyl)benzene-1,3,5-triol 1-Methyl-1-(2-nitro-4-(trifluoromethyl)phenyl)hydrazine (500 mg, 2.1 mmol), 2,4,6-Trihydroxybenzaldehyde (327 mg, 2.1 mmol)

Purification: Method 6; Yield: 160 mg, 20%; C₁₅H₁₂F₃N₃O₅, M=371.27 g/mol

¹H-NMR (300 MHz, d₆-DMSO) ppm: 3.46 (s, 3H), 5.84 (s, 2H), 7.67 (d, 1H, J=8.8 Hz), 7.95 (dd, 1H, J=1.8 Hz, J=8.8 Hz), 8.18 (s, 2H), 9.75 (s, 1H), 10.11 (s, 2H); ¹³C-NMR (75 MHz, d₆-DMSO) ppm: 35.85, 94.29, 99.03, 121.06 (q, $J_{C-F}$=33.5 Hz), 121.50, 123.19 (d, $J_{C-F}$=273.2 Hz), 123.40 (q, $J_{C-F}$=4.0 Hz), 129.62 (q, $J_{C-F}$=3.1 Hz), 139.70, 140.43, 143.87, 158.46, 160.83; GC-MS 371 m/z [M]⁺; Purity: 100.0% (336 nm, $t_r$=1.88 min, Method: c)

EXAMPLE 46

4-((2-(Quinolin-2-yl)hydrazono)methyl)benzene-1,3-diol

2-Hydrazinylquinoline (200 mg, 1.3 mmol), 2,4-Dihydroxybenzaldehyde (174 mg, 1.3 mmol) Purification: Method 1; Yield: 252 mg, 72%; C₁₆H₁₃N₃O₂, M=279.29 g/mol ¹H-NMR (300 MHz, d₆-DMSO) ppm: 6.33-6.36 (m, 2H), 7.24-7.31 (m, 2H), 7.39 (d, 1H, J=9.1 Hz), 7.54-7.61 (m, 2H), 7.75 (d, 1H, J=7.9 Hz), 8.13 (d, 1H, J=9.0 Hz), 8.24 (s, 1H), 9.73 (bs, 1H), 10.75 (bs, 1H), 11.12 (bs, 1H); ¹³C-NMR (75 MHz, d₆-DMSO) ppm: 102.43, 107.47, 109.40, 111.89, 122.30, 123.81, 125.55, 127.68, 128.94, 129.61, 137.77, 140.87, 147.07, 154.75, 157.80, 159.42; GC-MS 279 m/z [M]⁺; Purity: 93.4% (250 nm); 98.6% (326 nm); 100.0% (362 nm, $t_r$=1.40 min, Method: c)

EXAMPLE 47

5-((2-(Quinolin-2-yl)hydrazono)methyl)benzene-1,2,4-triol

2-Hydrazinylquinoline (500 mg, 3.2 mmol), 2,4,5-Trihydroxybenzaldehyde (516 mg, 3.2 mmol) Purification: Method 1; Yield: 704 mg, 76%; C₁₆H₁₃N₃O₃, M=295.29 g/mol ¹H-NMR (300 MHz, d₆-DMSO) ppm: 6.35 (s, 1H), 7.00 (s, 1H), 7.25 (t, 1H, J=6.1 Hz), 7.33 (d, 1H, J=8.7 Hz), 7.53-7.60 (m, 2H), 7.74 (d, 1H, J=7.9 Hz), 8.13 (d, 1H, J=8.8 Hz), 8.21 (s, 1H), 8.48 (bs, 1H), 9.4 (bs, 1H), 9.91 (bs, 1H), 10.97 (bs, 1H); ¹³C-NMR (75 MHz, d₆-DMSO) ppm: 103.38, 109.27, 110.93, 112.92, 122.12, 123.73, 125.49, 127.66, 129.59, 137.68, 138.38, 140.33, 147.11, 147.84, 150.16, 154.93; GC-MS 295 m/z [M]⁺; Purity: 82.9% (374 nm, $t_r$=5.22 min, Method: o)

EXAMPLE 48

4-((2-(Quinolin-2-yl)hydrazono)methyl)benzene-1,2,3-triol

2-Hydrazinylquinoline (500 mg, 3.2 mmol), 2,3,4-Trihydroxybenzaldehyde (516 mg, 3.2 mmol) Purification: Method 1; Yield: 750 mg, 81%; C₁₆H₁₃N₃O₃, M=295.29 g/mol ¹H-NMR (300 MHz, d₆-DMSO) ppm: 6.39 (d, 1H, J=8.4 Hz), 6.85 (d, 1H, J=8.5 Hz), 7.21-7.30 (m, 2H), 7.55-7.60

(m, 2H), 7.75 (d, 1H, J=7.9 Hz), 8.14 (d, 1H, J=9.1 Hz), 8.22 (s, 1H), 9.31 (bs, 2H), 10.77 (bs, 2H); $^{13}$C-NMR (75 MHz, d$_6$-DMSO) ppm: 107.44, 109.43, 112.16, 119.02, 122.30, 123.80, 125.55, 127.68, 129.66, 132.59, 137.79, 142.61, 146.25, 147.04, 147.50, 154.38; GC-MS 295 m/z[M]$^+$; Purity: 85.5% (248 nm), 82.1% (320 nm, t$_r$=4.43 min, Method: l)

EXAMPLE 49

5-((3-Mercapto-5-(pyridin-4-yl)-4H-1,2,4-triazol-4-ylimino)methyl)benzene-1,2,4-triol 4-Amino-5-(pyridin-4-yl)-4H-1,2,4-triazole-3-thiol (350 mg, 1.8 mmol), 2,4,5-Trihydroxybenzaldehyde (279 mg, 1.8 mmol)
Purification: Method 1; Yield: 568 mg, 95%; C$_{14}$H$_{11}$N$_5$O$_3$S, M=329.33 g/mol
$^1$H-NMR (300 MHz, d$_6$-DMSO) ppm: 6.43 (s, 1H), 7.24 (s, 1H), 7.86 (d, 2H, J=6.1 Hz), 8.76 (d, 2H, J=6.0 Hz), 8.83 (s, 1H), 9.53 (s, 1H), 9.77 (s, 1H), 9.98 (s, 1H), 14.30 (s, 1H); $^{13}$C-NMR (75 MHz, d$_6$-DMSO) ppm: 103.16, 108.34, 111.50, 121.60, 132.92, 139.21, 146.16, 150.10, 152.75, 153.84, 162.93, 163.86; GC-MS 178 m/z [C$_5$NH$_4$—C$_2$N$_3$—SH+H]$^+$, 151 m/z [2,3,4-tri-OH—C$_6$H$_3$CN]$^+$; Purity: 87.1% (254 nm, t$_r$=1:05 min, Method: n)

EXAMPLE 50

5-((2-(5-Chloro-3-iodopyridin-2-yl)hydrazono)methyl)benzene-1,2,4-triol

5-Chloro-2-hydrazinyl-3-iodopyridine (250 mg, 0.9 mmol), 2,4,5-Trihydroxybenzaldehyde (143, 0.9 mmol)
Purification: Method 1; Yield: 376 mg, 100%; C$_{12}$H$_9$ClIN$_3$O$_3$, M=405.58 g/mol
$^1$H-NMR (300 MHz, d$_6$-DMSO) ppm: 6.30 (s, 1H), 6.73 (s, 1H), 8.21 (s, 2H), 8.41 (s, 1H), 8.46 (s, 1H), 9.38 (s, 1H), 10.00 (s, 1H), 11.08 (s, 1H); $^{13}$C-NMR (75 MHz, d$_6$-DMSO) ppm: 77.47, 103.41, 109.66, 115.04, 120.46, 138.05, 145.52, 145.78, 146.09, 148.15, 151.37, 151.93; GC-MS 405 m/z [M]$^+$; Purity: 100.0% (368 nm, t$_r$=1.66 min, Method: c)

EXAMPLE 51

4-((Morpholinoimino)methyl)benzene-1,2,3-triol

Morpholin-4-amine (25 μL, 2.5 mmol), 2,3,4-Trihydroxybenzaldehyde (400 mg, 2.5 mmol) Purification: Method 1; Yield: 474 mg, 75%; C$_{11}$H$_{14}$N$_2$O$_4$, M=238.24 g/mol
$^1$H-NMR (300 MHz, d$_6$-DMSO) ppm: 3.02 (pt, 4H), 3.77 (pt, 4H), 6.33 (d, 1H, J=8.4 Hz), 6.66 (d, 1H, J=8.4 Hz), 7.88 (s, 1H), 8.22 (s, 1H), 9.15 (s, 1H), 11.49 (s, 1H); $^{13}$C-NMR (75 MHz, d$_6$-DMSO) ppm: 51.86, 65.35, 106.99, 111.72, 120.21, 132.36, 142.46, 146.55, 147.09; GC-MS 238 m/z [M]; Purity: 99.0% (300 nm, t$_r$=1.04 min, Method: d)

EXAMPLE 52

4-(2-(3,4-Dihydroxybenzylidene)hydrazinyl)benzoic acid

4-Hydrazinylbenzoic acid (500 mg, 3.4 mmol), 3,4-Dihydroxybenzaldehyde (454 mg, 3.4 mmol) Purification: Method 1; Yield: 370 mg, 41%; C$_{14}$H$_{12}$N$_2$O$_4$, M=272.26 g/mol
$^1$H-NMR (300 MHz, d$_6$-DMSO) ppm: 6.75 (d, 1H, J=8.1 Hz), 6.89 (dd, 1H, J=1.6 Hz, J=7.7 Hz), 7.03 (d, 2H, J=8.7 Hz), 7.18 (d, 1H, J=1.6 Hz), 7.78-7.81 (m, 3H), 9.14 (bs, 1H), 10.52 (s, 1H) 12.20 (bs, 1H); $^{13}$C-NMR (75 MHz, d$_6$-DMSO) ppm: 110.67, 112.05, 115.49, 118.94, 119.50, 126.68, 131.09, 139.85, 145.50, 146.60, 149.02, 167.23; GC-MS 272 m/z[M]$^+$; Purity: 100.0% (356 nm, t$_r$=1.95 min, Method: c)

EXAMPLE 53

5-((4-Methylpiperazin-1-ylimino)methyl)benzene-1,2,4-triol

4-Methylpiperazin-1-amine (200 mg, 1.7 mmol), 2,4,5-Trihydroxybenzaldehyde (268 mg, 1.7 mmol) Purification: Method 1; Yield: 330 mg, 76%; C$_{12}$H$_{17}$N$_3$O$_3$, M=251.28 g/mol
$^1$H-NMR (300 MHz, d$_6$-DMSO) ppm: 2.23 (s, 3H), 3.01 (pt, 4H), 3.43 (bs, 4H), 6.24 (s, 1H), 6.07 (s, 1H), 7.75 (s, 1H), 8.37 (bs, 1H), 9.19 (bs, 1H), 10.87 (s, 1H); $^{13}$C-NMR (75 MHz, d$_6$-DMSO) ppm: 45.25, 50.94, 53.59, 103.15, 110.28, 115.28, 137.79, 141.00, 147.08, 150.74; GC-MS 251 m/z [M]$^+$; Purity: 82.0% (294 nm), 100.0% (332 nm, t$_r$=1.05 min, Method: j)

EXAMPLE 54

5-((2-(6-Chloropyridazin-3-yl)hydrazono)methyl)benzene-1,2,4-triol

3-Chloro-6-hydrazinylpyridazine (200 mg, 1.4 mmol), 2,4,5-Trihydroxybenzaldehyde (213 mg, 1.4 mmol)
Purification: Method 1; Yield: 361 mg, 93%; C$_{11}$H$_9$ClN$_4$O$_3$, M=280.67 g/mol
$^1$H-NMR (300 MHz, d$_6$-DMSO) ppm: 6.34 (s, 1H), 7.03 (s, 1H), 7.40 (d, 1H, J=9.4 Hz), 7.65 (d, 1H, J=9.4 Hz), 8.26 (s, 1H), 8.43 (s, 1H), 9.34 (s, 1H), 9.49 (s, 1H), 11.33 (s, 1H); $^{13}$C-NMR (75 MHz, d$_6$-DMSO) ppm: 103.34, 110.84, 112.17, 115.26, 129.68, 138.52, 141.36, 146.52, 148.29, 150.08, 158.26; GC-MS 280 m/z[M]$^+$; Purity: 100.0% (354 nm, t$_r$=1.41 min, Method: k)

EXAMPLE 55

5-((2-(Phthalazin-1-yl)hydrazono)methyl)benzene-1,2,4-triol

1-Hydrazinylphthalazine hydrochloride (300 mg, 1.5 mmol), 2,4,5-Trihydroxybenzaldehyde (235 mg, 1.5 mmol)
Purification: Method 1; Yield: 449 mg, 99%, C$_{15}$H$_{12}$N$_4$O$_3$, M=296.28 g/mol
$^1$H-NMR (300 MHz, d$_6$-DMSO) ppm: 6.54 (s, 1H), 7.71 (s, 1H), 8.06-8.23 (m, 3H), 8.98 (s, 1H), 9.12 (d, 1H, J=7.8 Hz), 9.12 (s, 1H), 9.73 (bs, 1H), 10.13 (bs, 1H), 13.91 (s, 1H), 14.29 (bs, 1H); $^{13}$C-NMR (75 MHz, d$_6$-DMSO) ppm: 102.93, 109.82, 113.32, 118.92, 125.00, 127.53, 128.04, 133.53, 135.52, 138.89, 144.09, 146.69, 150.30, 151.34, 152.68; GC-MS 296 m/z [M]$^+$; Purity: 100.0% (392 nm, t$_r$=1.26 min, Method: l)

EXAMPLE 56

5-((2-(4,5-Dihydro-1H-imidazol-2-yl)hydrazono)methyl)benzene-1,2,4-triol

2-Hydrazinyl-4,5-dihydro-1H-imidazole hydrobromide (300 mg, 1.7 mmol), 2,4,5-Trihydroxybenzaldehyde (255 mg, 1.7 mmol)
Purification: Method 1; Yield: 379 mg, 97%, C$_{10}$H$_{12}$N$_4$O$_3$, M=236.23 g/mol
$^1$H-NMR (300 MHz, d$_6$-DMSO) ppm: 3.69 (s, 4H), 6.39 (s, 1H), 7.18 (s, 1H), 8.28 (s, 1H), 8.33 (s, 1H), 8.46 (bs, 1H), 9.31 (s, 1H), 9.71 (s, 1H), 11.93 (s, 1H); $^{13}$C-NMR (75 MHz, d$_6$-DMSO) ppm: 42.58, 102.99, 109.65, 112.42, 138.67, 145.88, 149.90, 151.03, 157.30; $^{13}$C-NMR (75 MHz, D$_4$-MeOH) ppm: 44.34, 104.14, 110.90, 115.00, 140.09, 150.31, 151.66, 153.55, 159.24; GC-MS 236 m/z [M]$^+$; Purity: 76.6% (346 nm, t$_r$=0.96 min, Method: p)

EXAMPLE 57

4-((2-Benzyl-2-methylhydrazono)methyl)benzene-1,2-diol

1-Benzyl-1-methylhydrazine (100 mg, 0.7 mmol), 3,4-Dihydroxybenzaldehyde (113 mg, 0.7 mmol)
Purification: Method 6; Yield: 30 mg, 16%, C$_{15}$H$_{16}$N$_2$O$_2$, M=256.30 g/mol
$^1$H-NMR (300 MHz, d$_6$-DMSO) ppm: 2.78 (s, 3H), 4.39 (s, 2H), 6.68 (d, 1H, J=7.98 Hz), 6.76 (dd, 1H, J=1.7 Hz, J=8.1 Hz), 7.06 (d, 1H, J=1.7 Hz), 7.14 (s, 1H), 7.23-7.35 (m, 7H); $^{13}$C-NMR (75 MHz, d$_6$-DMSO) ppm: 37.19, 61.57, 111.67, 115.34, 117.79, 126.96, 128.12, 128.25, 128.54, 132.92, 137.77, 145.19, 145.28; Purity: 64.6% (294 nm), 66.0% (298 nm) t$_r$=2.51 min, Method: l)

EXAMPLE 58

4-((2-(5-(4-Methoxyphenylamino)pyridin-2-yl)hydrazono)methyl)benzene-1,3-diol

C$_{19}$H$_{18}$N$_4$O$_3$, M=350.37 g/mol

Synthesis

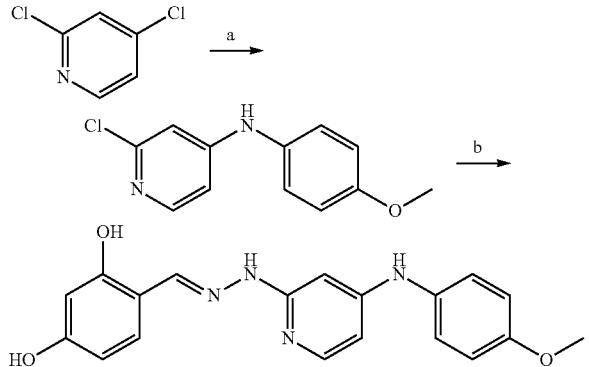

Example 58
a) 2,4-Dichloropyridine (2.0 g, 13.5 mmol) + 1.0 equiv. 4-Methoxyaniline + 2.0 equiv. p-Toluenesulfonic acid, Dioxane, 64 h reflux, aqueous workup, chromatography, yield: 53%, purity: 95%;
b) 1. 2-Chloro-N-(4-methoxyphenyl)pyridin-4-amine (0.5 g, 2.1 mmol) + 193.0 equiv. Hydrazine hydrate (64%), 16 h, 110° C., aqueous workup, 2. + 2.0 equiv. Aldehyde, Ethanol (EtOH), 2 h, 25° C., recrystallization, yield: 54%, purity: 99%

$^1$H-NMR (300 MHz, d$_6$-DMSO) ppm: 3.71 (s, 3H), 6.24 (dd, 1H, J=1.5 Hz, J=5.7 Hz), 6.30-6.35 (m, 3H), 6.84 (d, 2H, J=9.0 Hz), 6.87 (d, 1H, J=9.1 Hz), 7.51 (d, 2H, J=9.0 Hz), 7.80 (d, 1H, J=5.8 Hz), 8.09 (s, 1H), 8.55 (s, 1H), 9.77 (bs, 1H), 10.41 (s, 1H), 10.46 (s, 1H); $^{13}$C-NMR (75 MHz, d$_6$-DMSO) ppm: 55.07, 89.37, 99.78, 102.37, 107.51, 111.69, 113.72, 120.07, 128.90, 135.32, 140.49, 147.50, 151.03, 153.32, 157.23, 157.56, 159.41; ppm; LC-MS 350 m/z [M]$^+$; Purity: 99.3% (344 nm, t$_r$=1.44 min, Method: c)

EXAMPLE 59

4-((2-(4-(4-Methoxyphenylamino)phenyl)hydrazono)methyl)benzene-1,3-diol

C$_{20}$H$_{19}$N$_3$O$_3$, M=349.38 g/mol,

Synthesis

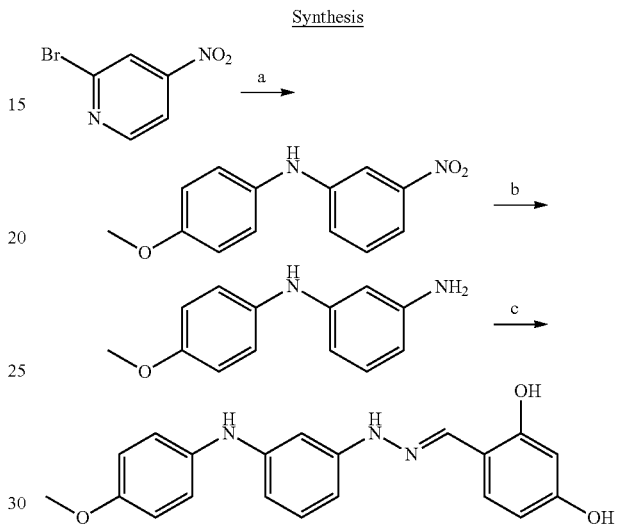

Example 59
a) Nitrobenzene (1.0 g, 4.9 mmol) + 1.2 equiv. 4-Methoxyaniline + 1.4 equiv. NaOtBu + 0.1 equiv. Tris(dibenzylideneacetone)dipalladium(0) + 0.1 equiv. [1,1'-Binaphthalene]-2,2'-diylbis(diphenylphosphine), Toluene, 16 h, 100° C., chromatography, yield: 73%, purity: 95%;
b) N-(4-Methoxyphenyl)-3-nitroaniline (2.0 g, 8.2 mmol) + EtOH, 2 h 25° C., chromatography, yield: 80%, purity: 95%;
c) 1. Aniline (0.8 g, 3.7 mmol) + 1.0 equiv. NaNO$_2$, 6M HCl, 20 min, in 3.0 equiv. SnCl$_2$ x 2H$_2$O, -15° C., 30 min, aqueous workup, 2. + 1.0 equiv. Aldehyde in Dichloromethane (DCM):EtOH (2:1), 16 h, 25° C., chromatography, recrystallization, yield: 19 %, purity: 99%.

$^1$H-NMR (300 MHz, d$_6$-DMSO) ppm: 3.72 (s, 3H), 6.26-6.34 (m, 4H), 6.55 (t, 1H, J=2.0 Hz), 6.87 (d, 2H, J=8.9 Hz), 6.99 (t, 1H, J=8.0 Hz), 7.05 (d, 2H, J=8.9 Hz), 7.21 (d, 1H, J=8.3 Hz), 7.78 (s, 1H), 7.98 (s, 1H), 9.64 (s, 1H), 9.98 (s, 1H), 10.81 (s, 1H); $^{13}$C-NMR (75 MHz, d$_6$-DMSO) ppm: 55.12, 97.80, 102.18, 102.37, 105.85, 107.26, 111.82, 114.34, 120.50, 129.14, 129.65, 136.12, 138.90, 145.70, 146.04, 153.61, 157.43, 158.72; ppm; LC-MS 350 m/z [M+H]$^+$; Purity: 97.4 (248 nm); 100.0% (294 nm); 99.2 (350 nm, t$_r$=2.01 min, Method: c)

EXAMPLE 60

4-((2-(4-(4-Methoxybenzyl)thiazol-2-yl)hydrazono)methyl)benzene-1,3-diol

C$_{18}$H$_{17}$N$_3$O$_3$S, M=355.41 g/mol,

Synthesis

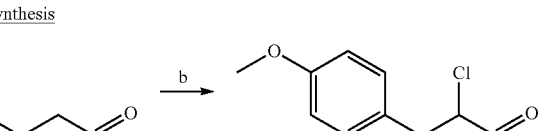

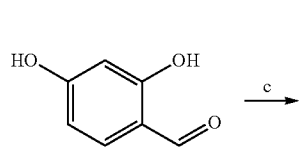
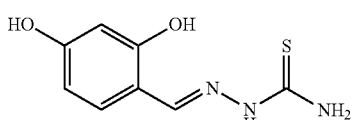
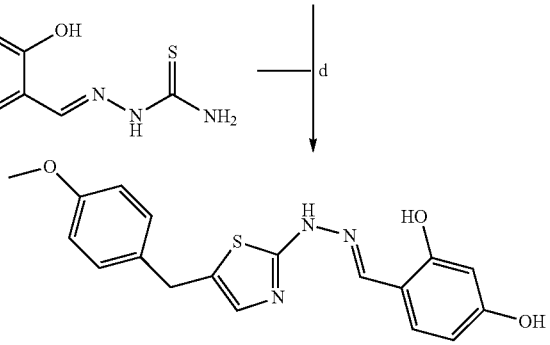

Example 60 a) Propanol (18.5 g, 111.3 mmol) + 1.8 equiv. $P_4O_{10}$ + 2.0 equiv. Dimethyl sulfoxide + 3.5 equiv. Triethylamine, DCM, 1 h at 0° C. to 25° C., aqueous workup yield: 90%, purity: 95%;
b) Aldehyde (2.4 g, 14.6 mmol) + 1.2 equiv. N-Chlorosuccinimide + cat. D-Proline at 0° C. in DCM, stirring for 3 h at 22° C., aqueous workup, chromatography, yield: 87%, purity: 85%;
c) Aldehyde (3.0 g, 21.7 mmol) + 1.0 equiv. Thiosemicarbazide, EtOH, 3 h reflux, recrystallization, yield: 72%, purity: 95%;
d) Hydrazinecarbothioamide (1.5 g, 7.1 mmol) + 1.0 equiv. 2-chloro-propanol, EtOH, 2 h reflux, aqueous workup, chromatography, yield: 17%, purity: 100%.

$^1$H-NMR (300 MHz, $d_6$-DMSO) ppm: 3.73 (s, 3H), 3.86 (s, 2H), 6.28 (d, 1H, J=2.2 Hz), 6.30 (dd, 1H, J=2.3 Hz, J=8.4 Hz), 6.88 (d, 2H, J=8.6 Hz), 6.91 (s, 1H), 7.17 (d, 2H, J=8.6 Hz), 7.26 (d, 1H, J=8.4 Hz), 8.15 (s, 1H), 9.76 (s, 1H), 10.50 (bs, 1H), 11.36 (bs, 1H); $^{13}$C-NMR (75 MHz, $d_6$-DMSO) ppm: 31.74, 54.91, 102.31, 107.58, 111.32, 113.80, 129.20, 129.39, 131.81, 157.78, 158.05, 159.70, 167.34; ppm; LC-MS 355 m/z [M]$^+$; Purity: 87.8% (250 nm); 100.0% (376 nm, $t_r$=6.22 min, Method: c)

EXAMPLE 61

1-(2,4-Dimethoxyphenyl)-2-(4-(trifluoromethyl)benzylidene)hydrazine $C_{16}H_{15}F_3N_2O_2$, M=324.30 g/mol, Synthesis

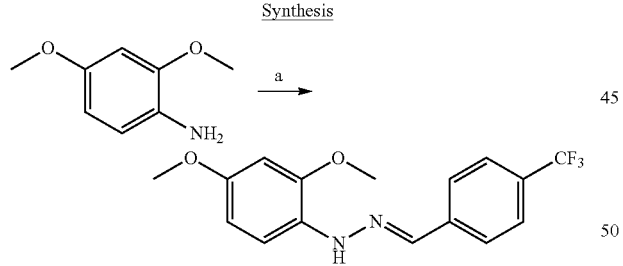

Example 61 a) 1. Aniline (10.0 g, 65.3 mmol) + 1.0 equiv. $NaNO_2$, aq. HCl (6M), 20 min, in 3.0 equiv. $SnCl_2$ x $2H_2O$, -15° C., 30 min, aqueous workup, 2. + 0.6 equiv. Aldehyde in DCM:EtOH (2:1), 1 h, 25° C., chromatography, recrystallization, yield: 17%, purity: 91%.

$^1$H-NMR (300 MHz, $d_6$-DMSO) ppm: 3.72 (s, 3H), 3.84 (s, 3H), 6.51 (dd, 1H, J=2.6 Hz, J=8.22 Hz), 6.61 (d, 1H, J=2.6 Hz), 7.31 (d, 1H, J=8.7 Hz), 7.69 (d, 2H, J=8.4 Hz), 7.77 (d, 2H, J=8.2 Hz), 8.11 (s, 1H), 9.81 (s, 1H);

$^{13}$C-NMR (75 MHz, $d_6$-DMSO) ppm: 55.28, 55.60, 99.20, 104.96, 112.58, 124.32 (d, $J_{C-F}$=271.6 Hz), 125.40 (q, $J_{C-F}$=3.8 Hz), 125.56, 127.05 (q, $J_{C-F}$=31.6 Hz), 127.87, 134.64, 140.18, 146.31, 153.49; LC-MS 323 m/z[M–H]$^+$;

Purity: 91.3% (354 nm, $t_r$=6.22 min, Method: c)

EXAMPLE 62

2-(2-(Pyridin-2-ylmethylene)hydrazinyl)quinoline

Alfa Aesar, Karlsruhe, Germany

EXAMPLE 63

N'-(1-(2,4-Dihydroxyphenyl)ethylidene)-2-hydroxybenzohydrazide

TimTec, Newark, USA

EXAMPLE 64

2-Chloro-N'-(1-(2,4-dihydroxyphenyl)ethylidene)-4-nitrobenzohydrazide

TimTec, Newark, USA

EXAMPLE 65

N'-(1-(2,4-Dihydroxyphenyl)ethylidene)-3-iodobenzohydrazide

TimTec, Newark, USA

EXAMPLE 66

1-(4-Cyanophenyl)-N'-(2,4-dihydroxybenzylidene)piperidine-4-carbohydrazide 1-(4-Cyanophenyl)piperidine-4-carbohydrazide (250 mg, 1.0 mmol), 2,4-Dihydroxybenzaldehyde (141 mg, 1.0 mmol)

Purification: Method 1; Yield: 157 mg, 42%, $C_{20}H_{20}N_4O_3$, M=364.40 g/mol $^1$H-NMR (300 MHz, $d_6$-DMSO) ppm: 1.61-1.71 (m, 2H), 1.82 (pd, 2H), 2.80-3.04 (m, 3H), 3.98 (pd, 2H), 6.28-6.35 (m, 2H), 7.03 (d, 2H, J=9.0 Hz), 7.26 (s, 1H, J=8.4 Hz), 7.56 (d, 2H, J=8.7 Hz), 8.25 (s, 1H), 9.91 (s, 0.8H), 11.02 (s, 0.2H), 11.33 (s, 1H), 11.47 (s, 1H); $^{13}$C-NMR (75 MHz, $d_6$-DMSO) ppm: 18.45, 27.22, 46.14, 97.54, 102.51, 107.50, 110.33, 114.01, 120.00, 131.11, 133.28, 147.77, 152.73, 159.21, 160.45, 169.72; GC-MS 364 m/z [M]$^+$, 184; Purity: 98.6% (298 nm, $t_r$=1.17 min, Method: c)

EXAMPLE 67

N'-(2,4-Dihydroxybenzylidene)-2-phenylacetohydrazide

2-Phenylacetohydrazide (200 mg, 1.3 mmol), 2,4-Dihydroxybenzaldehyde (183 mg, 1.3 mmol)

Purification: Method 1; Yield: 179 mg, 49%, $C_{15}H_{14}N_2O_3$, M=270.28 g/mol $^1$H-NMR (300 MHz, d$_6$-DMSO) ppm: 3.53 (s, 2H), 6.29-6.36 (m, 3H), 7.23-7.32 (m, 5H), 8.28 (s, 1H), 9.92 (bs, 0.8H), 11.15 (0.2H) 11.26 (s, 1H), 11.63 (s, 1H); $^{13}$C-NMR (75 MHz, d$_6$-DMSO) ppm: 40.84, 102.50, 107.53, 110.31, 126.51, 128.22, 128.96, 131.08, 135.48, 147.88, 159.21, 160.52, 165.86; GC-MS 270 m/z [M]$^+$; Purity: 94.6.0% (240 nm); 99.5% (294 nm), 100.0 (322 nm) $t_r$=1.10 min, Method: c)

EXAMPLE 4

Modulation of htt Protein Processing by Compounds of Formula I

4.1 Cultivation of PC12-Htt-Ex1-Q25 and PC12-Htt-Ex1-Q103

Inducible PC12 cells were kept in high glucose D-MEM supplemented with 5% horse serum, 2.5% FCS, 1% glutamine, 100 µg/ml penicillin, and 100 µg/ml streptomycine at 37° C. and 5% CO$_2$. 100 µg/ml zeocine and 50 µg/ml G418 (geneticine) were added to the culture medium, for selection. Cells were grown in 75 cm$^2$ culture flasks coated with collagen up to 90% confluence and split once a week either 1:4 for PC12-Q25 or 1:6 for PC12-Q103.

4.2 Test of Chemical Compounds in Inducible PC12 Cells

Method 1

To test the effect of chemical compounds on htt-processing, PC12-Q103 cells were plated in 96-well tissue culture plates coated with collagen at approximately 2300 cells/well in a total volume of 80 µl. For counting, a Neubauer haemocytometer using a 1:1 dilution of cell suspension and trypan blue was used.

After 24 hours, 10 µl of culture medium containing either 2.5 µM (0.25 µl of a 1 mM solution/well) ponasterone A (dissolved in 100% EtOH) for induction of htt-expression or 0.25 µl 100% ethanol as a negative control were added. One hour later, the substances diluted in DMSO were added in six different concentrations in a total volume of 10 µl culture medium. Control samples were analysed in triplicates, the wells containing the respective substance in four replicates.

Following 72 hours incubation at 37° C., cell morphology and confluency was evaluated and htt-expression and formation of htt-aggregates in PC12-Q103 were examined via GFP-fluorescence using an Olympus IX70 microscope. Afterwards, the medium was removed and 65 µl of lysis buffer (20 mM Hepes pH 7.3, 150 mM NaCl, 2 mM EDTA, 1% Tween-20+1× complete protease inhibitor cocktail [Roche], 10 mM NaF, 0.25 units/µl benzonase) was added to each well. Cell lysis was performed for 30 minutes on ice.

To estimate the effect of the compounds on the processing in PC12-Q103 cells, htt levels were measured. For the detection of htt-aggregates in the lysate, a cellulose acetate membrane and two thin Whatman filter papers were equilibrated in lysis buffer and mounted in a vacuum filtration unit. The membrane was washed once with 100 µl of lysis buffer per well of the filter unit. Then, 100 µl of lysis buffer was pipetted in each well and the total cell lysate was added. The mixture was filtered through the membrane. Finally, the membrane was washed once with 100 µl lysis buffer, taken out of the filter unit and the detection of the GFP signal was performed immediately under blue light with the LAS-3000 photo imager and quantified by using the AIDA software.

Figure 5:
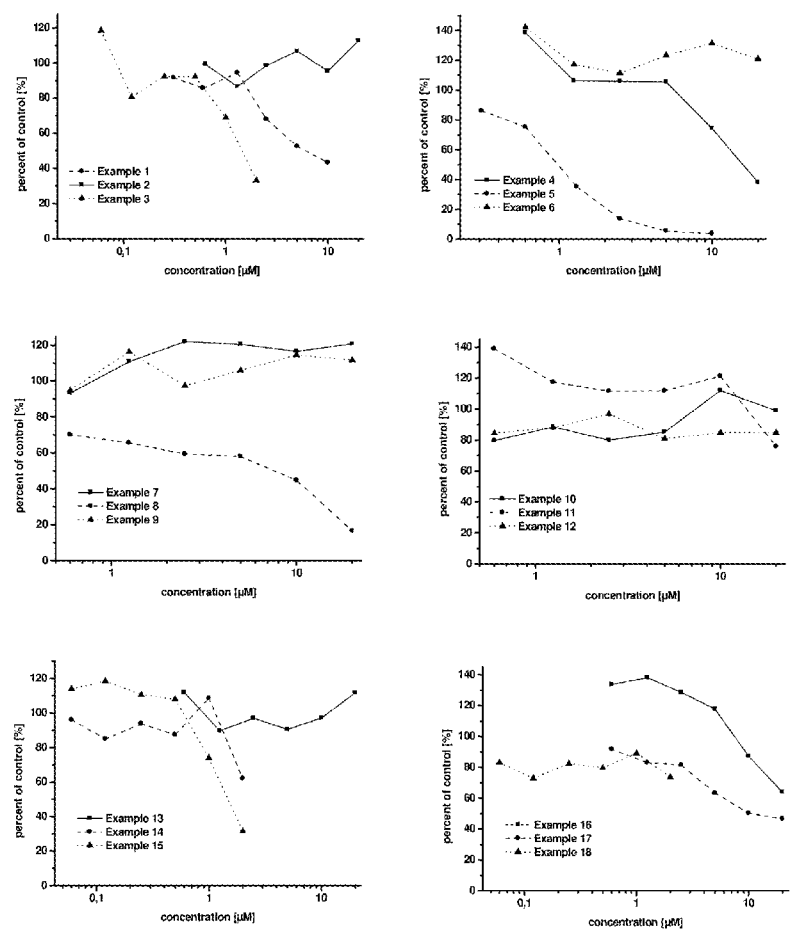
FIGS. 5 and 6 illustrate the amount of HTT-Q103-protein in PC12 cells after incubation with product examples 1-36 and 40-42 in concentration dependence as percent of control DMSO.
Figure 6:
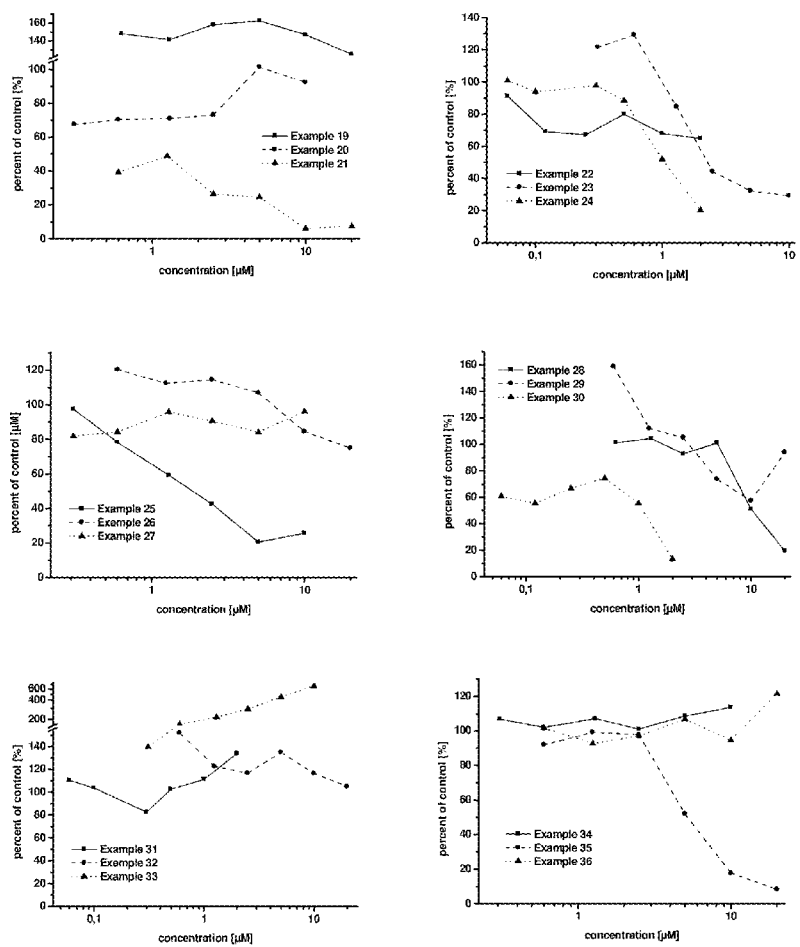
Figure 6:
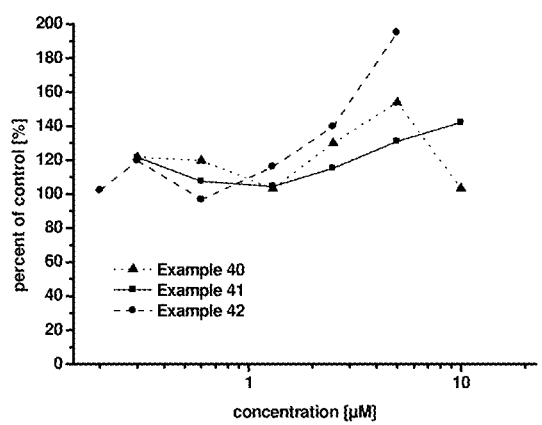

The results are shown in FIGS. 5 and 6. As to the compounds according to the invention not listed in these figures, promising results have been obtained in preliminary tests.

Method 2

The Htt-Q25 and -Q103 protein levels were evaluated in total lysate and in the supernatant and pellet of stably transfected PC12 cells. PC12-Htt-Ex1-Q25 and PC12-Htt-Ex1-Q103 cells were cultured on collagen coated 24-well plates. 24 hours after plating, expression was induced by adding ponasterone A (2.5 µM). Then drugs (5 µM) or DMSO as a control were added. After 48 h, Htt-expression levels were examined. For Htt-expression analysis, cells were washed once with D-PBS and lysed with lysis buffer (20 mM Hepes pH 7.3, 2 mM EDTA, 150 mM NaCl, 1% Tween-20+1× complete protease inhibitor cocktail [Roche], 10 mM NaF, 0.25 units/µl benzonase) for 30 minutes on ice. An aliquot of total cell lysate was ultra centrifuged (30 min, 55.000 rpm, [TLA-55 rotor] 4° C.) to obtain soluble and pellet fractions of each sample. The pellet was then resuspended in lysis buffer. 5-fold SDS sample buffer containing DTT was added to total lysate, supernatant and pellet fractions and heated to 95° C. for 5 minutes. SDS-PAGE was performed in 12.5% polyacrylamide resolving gels and 4% polyacrylamide stacking gels. Gels were transferred onto nitrocellulose membranes, which were then blocked with skim milk (3%) in TBS-Tween-20. Membranes were incubated over night at 4° C. with anti-GAPDHrab antibody (1:1000 in 3% skim milk in TBS-Tween-20), washed three times and subsequently incubated with anti-HD721rab-antibody (1:2000 in 3% skim milk) for 1 h at room temperature. This was followed by incubation with a secondary antibody (anti-rabbit 1:5000 in 3% skim milk in TBS-Tween-20) conjugated to alkaline phosphatase (AP). Membranes were washed and treated for 3 minutes in a 2000-fold dilution of AttoPhos™ reagent in AttoPhos™ buffer. Signals were recorded under blue light in the LAS-3000 photo imager. Evaluation was carried out with AIDA software. The GAPDH concentration was used for normalizing protein levels.

Figure 7:
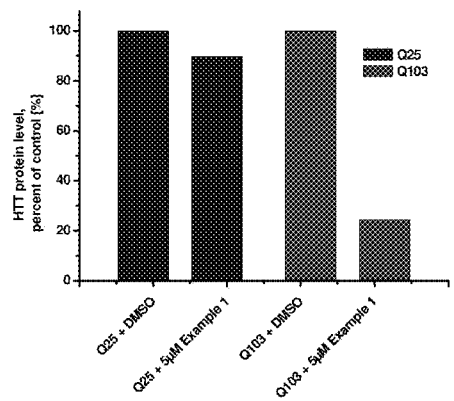
FIG. 7 illustrates the effect of product example 1 on the HTT-Q25 and -Q103 protein levels (A) and of product examples 4, 23, 25, 32, 35 and 36 on the HTT-Q103-protein level (B).
Figure 7:
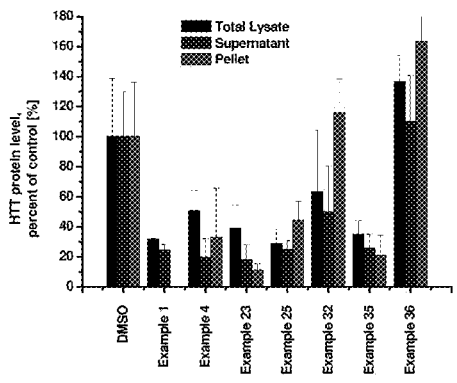

The results are shown in FIG. 7.

Method 3

GST-Htt-Q53-protein stock solution was ultra-centrifugated (40 min, 55.000 rpm [TLA-55 rotor], 4° C.); the supernatant was diluted with H$_2$O to a final concentration of 2 µM. DMSO as a control, or drugs at various concentrations were added to the supernatant of GST-Htt-Q53 protein which was preincubated with PreScission Protease (GE Healthcare, #27-0843-01) in Tris-buffer (A:B=1:1; A:50 mM Tris, 150 mM NaCl, pH=6.8; B:1 mM EDTA, pH=8.0+ 10 mM DTT) and incubated at 30° C. (300 rpm). Samples were taken at 0, 4, 5 and 6 h. The samples were diluted with SDS-buffer (4% SDS, 100 mM DTT) and heated at 98° C. for 5 min. Samples were filtered through a cellulose-acetate membrane which was equilibrated with SDS solution (0.1%). The membrane was washed twice (SDS, 0.1%), blocked with skim milk (3% in PBS) for 30 min and developed with CAG antibody over night at 4° C. and with peroxidase labeled anti rabbit-antibody for 1 h at room temperature. The membrane was washed (2×TBS-0.05% Tween-20, 2×TBS) and luminescence was recorded with Chem Glow.

Figure 10:
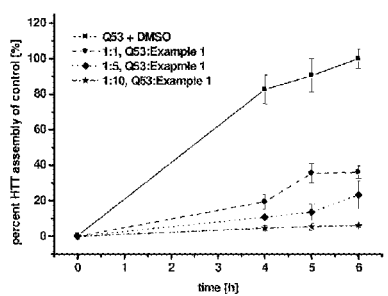
FIG. 10 illustrates the time-dependent change in conformation of the HTT-Q53 protein caused by product examples 1 and 23, detected by the conformational CAG antibody.
Figure 10:
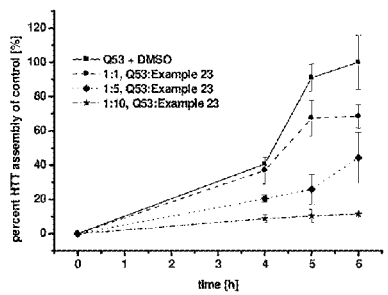

The results are shown in FIG. 10.

EXAMPLE 5

Viability Assay

Method 1

Cell viability was assayed on HepG2 cells. HepG2 cells were cultured in 96-well black culture plates with transparent bottom in RPMI medium (1% L-Glu, 10% FCS). 3 hours after plating, different drug concentrations (0.1 µM-100 µM) or DMSO as control were added. Chlorpromazine hydrochloride (Sigma, # C0982) and cycloheximide (Sigma, # C1988) were used as control substances. Each concentration was run in triplicates. After 48 hours of incubation, Alamar Blue reagent (BIOSOURCE, # DAL1100) was added and plates were incubated for 4 hours at 37° 0. Absorbance was measured in the Tecan-plate reader (Tecan, infinite M200) at 570 nm and 600 nm. Product example 1 was insoluble from a concentration of 50 µM, product example 33 from 30 µM and product example 23 at 100 µM.

Figure 8:
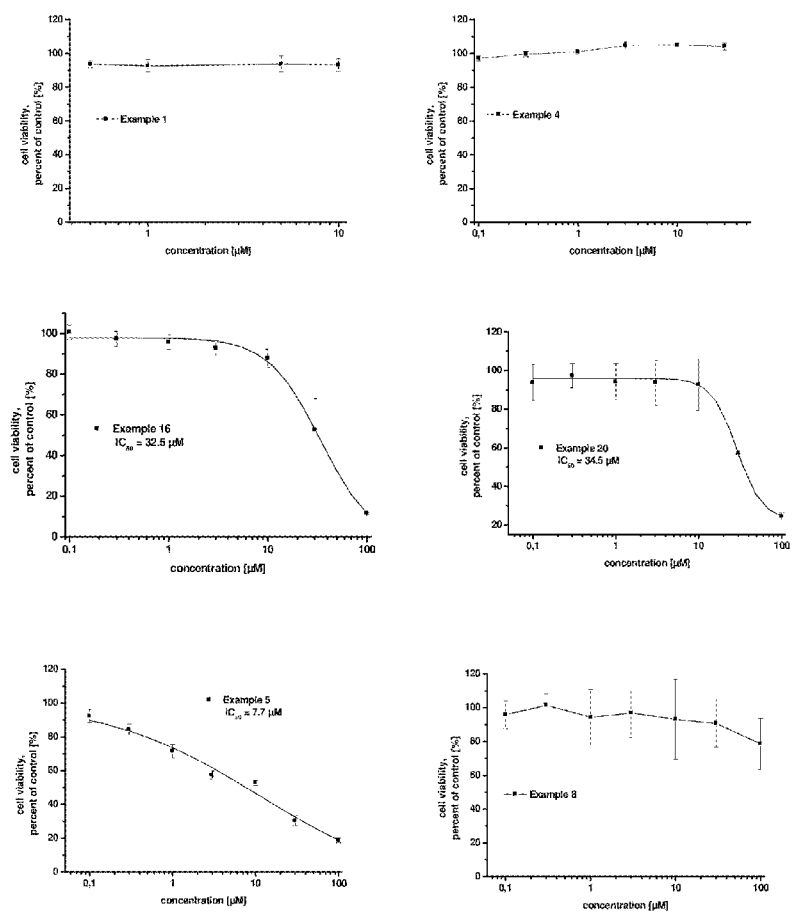
FIGS. 8 and 9 illustrate the influence of product examples 1, 4, 5, 8, 16 and 20, 21, 23, 25, 27, 33, 37-43, 46, 61, 62-66 on the cell viability of HEP-G2 cells in concentration dependence.
Figure 9:
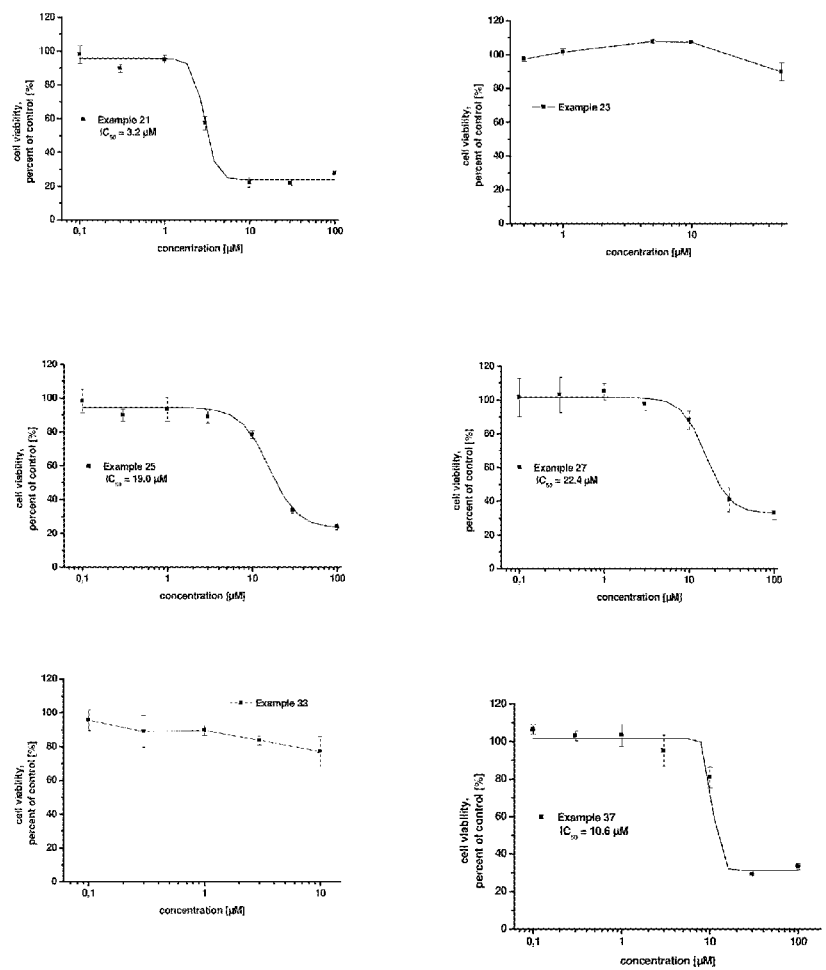
Figure 9:
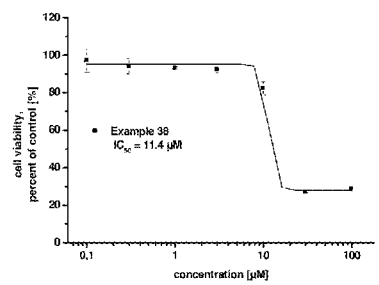
Figure 9:
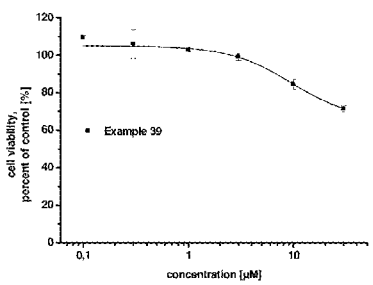
Figure 9:
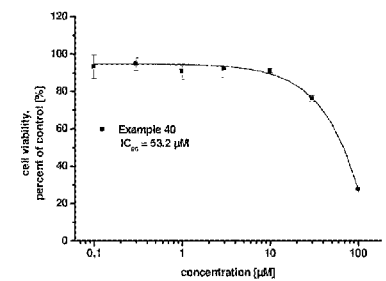
Figure 9:
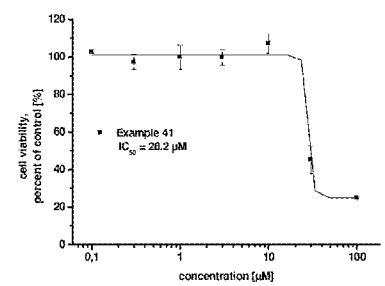
Figure 9:
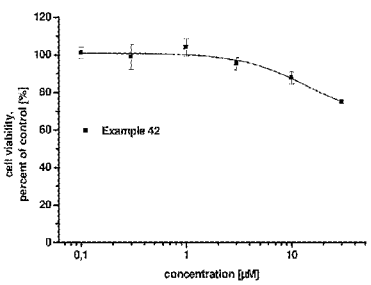
Figure 9:
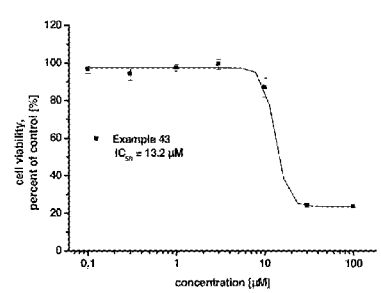
Figure 9:
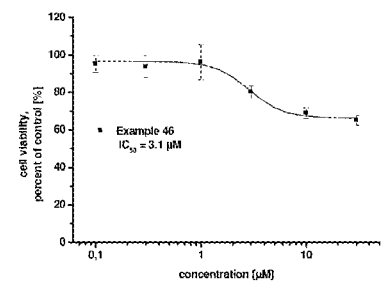
Figure 9:
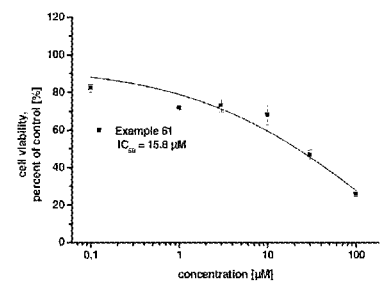
Figure 9:
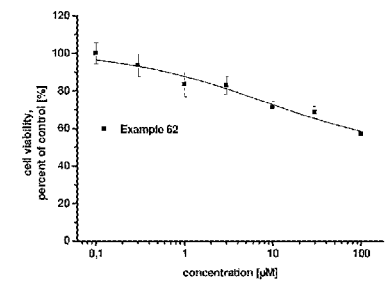
Figure 9:
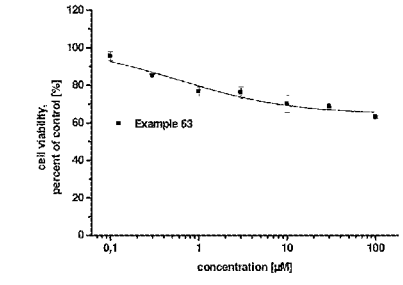
Figure 9:
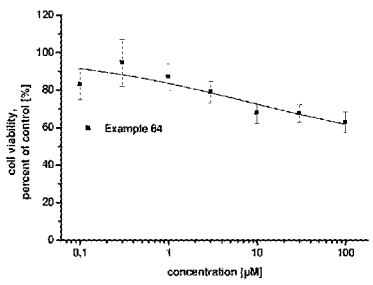
Figure 9:
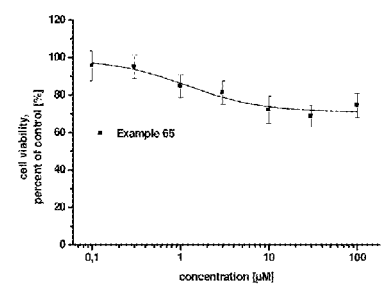
Figure 9:
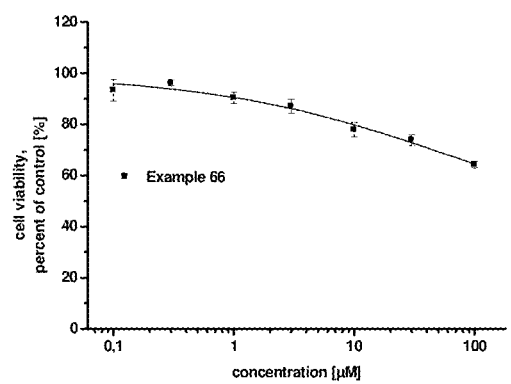
Figure 9:
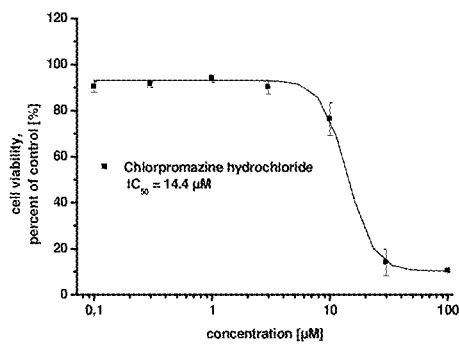

The results are shown in FIGS. 8 and 9.

Method 2

The tubulin polymerization assay (Cytoskeleton, Inc., Denver, Colo., USA, #BK011) was performed in accordance to the instruction manual.

Figure 11:
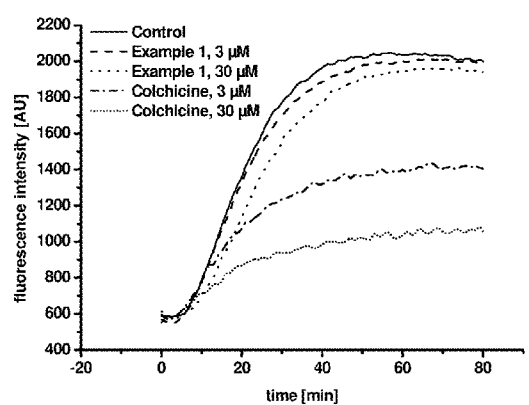
FIG. 11 illustrates that product example 1 shows no effect on tubulin polymerization at various concentrations.

The results are shown in FIG. 11.

---

The invention claimed is:
1. A compound which is selected from
4-((2-(2,6-Dichloro-4-(trifluoromethyl)phenyl)hydrazono)methyl)benzene-1,3-diol,
1-(2,6-Dichloro-4-(trifluoromethyl)phenyl)-2-(2,4-dimethoxybenzylidene)hydrazine,
4-((2-(2,6-Dichloro-4-(trifluoromethyl)phenyl)hydrazono)methyl)benzene-1,2-diol,
4-((2-(4-(Trifluoromethyl)phenyl)hydrazono)methyl)benzene-1,3-diol,
4-((2-(4-(Trifluoromethyl)phenyl)hydrazono)methyl)benzene-1,2-diol,
5-((2-(4-Fluorophenyl)hydrazono)methyl)benzene-1,2,4-triol,
4-((2-(4-Fluorophenyl)hydrazono)methyl)benzene-1,3-diol,
3-((2-(4-Fluorophenyl)hydrazono)methyl)benzene-1,2-diol,
4-((2-(2,4-Difluorophenyl)hydrazono)methyl)benzene-1,3-diol,
5-((2-(2,4-Difluorophenyl)hydrazono)methyl)benzene-1,2,4-triol,
4-((2-(2,4-Difluorophenyl)hydrazono)methyl)benzene-1,2-diol,
4-((2-Phenylhydrazono)methyl)benzene-1,3-diol,
4-((2-(2,5-Dichlorophenyl)hydrazono)methyl)benzene-1,3-diol,
4-((2-(2-Chloro-5-(trifluoromethyl)phenyl)hydrazono)methyl)benzene-1,3-diol,
4-((2-(2-Chloro-phenyl)hydrazono)methyl)benzene-1,3-diol,
4-((2-(2,4-Dichlorophenyl)hydrazono)methyl)benzene-1,3-diol,
4-((2-(2-Chloro-4-(trifluoromethyl)phenyl)hydrazono)methyl)benzene-1,3-diol,
4-((2-(4-Iodophenyl)hydrazono)methyl)benzene-1,3-diol,
5-((2-(4-Iodophenyl)hydrazono)methyl)benzene-1,2,4-triol,
5-((2,2-Diphenylhydrazono)methyl)benzene-1,2,4-triol,
4-((2,2-Diphenyl-hydrazono)methyl)benzene-1,3-diol,
4-((2-(Perfluorophenyl)hydrazono)methyl)benzene-1,3-diol,
4-((2-(Perfluorophenyl)hydrazono)methyl)benzene-1,2-diol,
4-((2-Methyl-2-phenylhydrazono)methyl)benzene-1,2-diol,
4-((2-Methyl-2-phenylhydrazono)methyl)benzene-1,3-diol,
5-((2-Methyl-2-phenylhydrazono)methyl)benzene-1,2,4-triol,
3-Chloro-4-(2-(2,4,5-trihydroxybenzylidene)hydrazinyl)benzonitrile,
3-Chloro-4-(2-(2,4-dihydroxybenzylidene)hydrazinyl)benzonitrile,
3-Chloro-4-(2-(3,4-dihydroxybenzylidene)hydrazinyl)benzonitrile,
4-((2-(4-Nitrophenyl)hydra-zono)methyl)benzene-1,2-diol,
5-((2-(4-Nitrophenyl)hydrazono)methyl)benzene-1,2,4-triol,
4-((2-(4-Nitrophenyl)hydrazono)methyl)benzene-1,3-diol,
4-((Piperidin-1-ylimino)methyl)benzene-1,3-diol,
4-((2-(Benzo[d]-thiazol-2-yl)hydrazono)methyl)benzene-1,3-diol,
3-(2-(2,4-Dihydroxybenzyl-idene)hydrazinyl)propanenitrile,
2-((2-(4-(Trifluoromethyl)phenyl)hydrazono)methyl)benzene-1,3,5-triol,
2-((2-(2,6-Dichloro-4-(trifluoromethyl)phenyl)hydrazono)methyl)benzene-1,3,5-triol,
2-((2-(Benzo[d]thiazol-2-yl)hydrazono)methyl)benzene-1,3,5-triol,
4-((2-Methyl-2-(2-nitro-4-(trifluoromethyl)phenyl)hydrazono)methyl)benzene-1,3-diol,
4-((2-Methyl-2-(2-nitro-4-(trifluoromethyl)phenyl)hydrazono)methyl)benzene-1,2,3-triol,
2-((2-Methyl-2-(2-nitro-4-(trifluoromethyl)phenyl)hydrazono)methyl)benzene-1,3,5-triol,
4-((2-(Quinolin-2-yl)hydrazono)methyl)benzene-1,3-diol,
5-((2-(Quinolin-2-yl)hydrazono)methyl)benzene-1,2,4-triol,
4-((2-(Quinolin-2-yl)hydrazono)methyl)benzene-1,2,3-triol,

5-((3-Mercapto-5-(pyridin-4-yl)-4H-1,2,4-triazol-4-ylimino)methyl)benzene-1,2,4-triol,
5-((2-(5-Chloro-3-iodopyridin-2-yl)hydrazono)methyl)benzene-1,2,4-triol,
4-((Morpholinoimino)methyl)benzene-1,2,3-triol,
4-(2-(3,4-Dihydroxybenzylidene)hydrazinyl)benzoic acid,
5-((4-Methylpiperazin-1-ylimino)methyl)benzene-1,2,4-triol,
5-((2-(6-Chloropyridazin-3-yl)hydrazono)methyl)benzene-1,2,4-triol,
5-((2-(Phthalazin-1-yl)hydrazono)methyl)benzene-1,2,4-triol,
5-((2-(4,5-Dihydro-1H-imidazol-2-yl)hydrazono)methyl)benzene-1,2,4-triol,
4-((2-Benzyl-2-methylhydrazono)methyl)benzene-1,2-diol,
4-((2-(5-(4-Methoxyphenylamino)pyridin-2-yl)hydrazono)methyl)benzene-1,3-diol,
4-((2-(4-(4-Methoxyphenylamino)phenyl)hydrazono)methyl)benzene-1,3-diol,
4-((2-(4-(4-Methoxybenzyl)thiazol-2-yl)hydrazono)methyl)benzene-1,3-diol,
N'-(1-(2,4-Dihydroxyphenyl)ethylidene)-2-hydroxybenzohydrazide,
2-Chloro-N'-(1-(2,4-dihydroxyphenyl)ethylidene)-4-nitrobenzohydrazide,
N'-(1-(2,4-Dihydroxyphenyl)ethylidene)-3-iodobenzohydrazide,
1-(4-Cyanophenyl)-N'-(2,4-dihydroxybenzylidene)piperidine-4-carbohydrazide, and
N'-(2,4-Dihydroxybenzylidene)-2-phenylacetohydrazide or a physiologically acceptable salt, hydrate, solvate, tautomer, or stereoisomer thereof.

2. The compound according to claim 1, wherein at least one hydrogen of a hydrocarbon group of at least one aromatic radical is replaced by deuterium and/or wherein at least one hydrogen of a nitrogen-hydrogen binding is replaced by deuterium.

3. The compound according to claim 1, wherein said compound is present as a metal salt.

4. The compound according to claim 3, wherein the metal salt is selected from an Fe, Mo, Ni, Cu, Zn, V and Co salt.

5. A pharmaceutical composition comprising the compound of claim 1 formulated for human or veterinary administration, wherein the compound inhibits protein misfolding or formation of protein aggregates.

6. The composition according to claim 5, wherein the protein has a polyglutamine stretch within its primary structure, wherein the polyglutamine stretch is more than 15 glutamine residues in length.

7. The composition of claim 6, wherein the protein is mutated htt.

8. The composition of claim 5, formulated for treating Huntington's disease (HD), spinobulbar muscular atrophy (Kennedy disease), dentatorubral-pallidoluysian atrophy (Haw River syndrome), spinocerebellar ataxia type 1, spinocerebellar ataxia type 2, spinocerebellar ataxia type 3 (Machado-Joseph disease), spinocerebellar ataxia type 6, spinocerebellar ataxia type 7, spinocerebellar ataxia type 17, Alzheimer's disease, Parkinson's disease, primary systemic amyloidosis, secondary systemic amyloidosis, senile systemic amyloidosis, familial amyloid polyneuropathy 1, hereditary cerebral amyloid angiopathy, hemodialysis-related amyloidosis, familial amyloid polyneuropathy III, Finnish hereditary systemic amyloidosis, type 2 diabetes, medullary carcinoma of thyroid, atrial amyloidosis, hereditary non-neuropathic systemic amyloidosis, injection-localized amyloidosis, hereditary renal amyloidosis, amyotrophic lateral sclerosis, transmissible spongiform encephalopathies (prion diseases): bovine spongiform encephalopathy, kuru, Gerstmann-Straeussler-Scheinker syndrome, fatal familial insomnia, scrapie, Creutzfeldt-Jakob disease, variant Creutzfeldt-Jakob disease.

9. The composition of claim 5, wherein the protein has a polyglutamine stretch within its primary structure, wherein the polyglutamine stretch is more than 27 glutamine residues in length.

10. The composition of claim 5 formulated for treating Huntington's disease (HD), spinobulbar muscular atrophy (Kennedy disease), dentatorubral-pallidoluysian atrophy (Haw River syndrome), spinocerebellar ataxia type 1, spinocerebellar ataxia type 2, spinocerebellar ataxia type 3 (Machado-Joseph disease), spinocerebellar ataxia type 6, spinocerebellar ataxia type 7, and spinocerebellar ataxia type 17.

11. A kit for modulating protein misfolding comprising a compound of claim 1, and an agent for detecting protein misfolding.

* * * * *